(12) United States Patent
Agrawal et al.

(10) Patent No.: US 10,391,242 B2
(45) Date of Patent: Aug. 27, 2019

(54) DIABETES THERAPY MANAGEMENT SYSTEM FOR RECOMMENDING BOLUS CALCULATOR ADJUSTMENTS

(71) Applicant: MEDTRONIC MINIMED, INC., Northridge, CA (US)

(72) Inventors: Pratik Agrawal, Sherman Oaks, CA (US); Brian T. Kannard, Mountain View, CA (US); Francine R. Kaufman, Los Angeles, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 576 days.

(21) Appl. No.: 13/910,766

(22) Filed: Jun. 5, 2013

(65) Prior Publication Data

US 2013/0345663 A1 Dec. 26, 2013

Related U.S. Application Data

(60) Provisional application No. 61/656,765, filed on Jun. 7, 2012.

(51) Int. Cl.
*A61M 5/172* (2006.01)
*G16H 15/00* (2018.01)
(Continued)

(52) U.S. Cl.
CPC ....... *A61M 5/1723* (2013.01); *A61B 5/14532* (2013.01); *A61B 5/4839* (2013.01);
(Continued)

(58) Field of Classification Search
CPC ..... G06Q 50/22; G06Q 50/24; A61M 5/1723; G16H 15/00; G06F 19/3468;
(Continued)

(56) References Cited

U.S. PATENT DOCUMENTS 3,631,847 A 1/1972 Hobbs, II
4,212,738 A 7/1980 Henne
(Continued)

FOREIGN PATENT DOCUMENTS

CN 101052930 A 10/2007
CN 101290320 A 10/2008
(Continued)

OTHER PUBLICATIONS

PCT Search Report (PCT/US02/03299), dated Oct. 31, 2002, Medtronic Minimed, Inc.
(Continued)

*Primary Examiner* — Eliza A Lam
(74) *Attorney, Agent, or Firm* — Lorenz & Kopf, LLP

(57) ABSTRACT

A method of managing use of an insulin infusion device is presented here. The method identifies bolus calculator event data from glucose data for a user of the infusion device. The bolus calculator event data corresponds to use of a bolus calculator that calculates bolus dosage recommendations based on a user entered carbohydrate consumption value, a user entered current blood glucose value, a user specific carbohydrate ratio value, and a user specific insulin sensitivity value. The method filters the bolus calculator event data to remove glucose data associated with certain conditions, and analyzes the filtered data to detect an event occurrence that is indicative of potential maladjustment of the carbohydrate ratio value or the insulin sensitivity value. The method outputs a recommendation to adjust the carbohydrate ratio value or the insulin sensitivity value, based on characteristics of the detected event occurrence.

34 Claims, 48 Drawing Sheets

(51) Int. Cl.
*G06F 19/00* (2018.01)
*A61B 5/00* (2006.01)
*A61B 5/145* (2006.01)

(52) U.S. Cl.
CPC ............ *A61B 5/7275* (2013.01); *A61B 5/743* (2013.01); *G06F 19/3468* (2013.01); *G16H 15/00* (2018.01)

(58) Field of Classification Search
CPC ..... A61B 5/7275; A61B 5/743; A61B 5/4839; A61B 5/14532
USPC ........................................................ 705/2–3
See application file for complete search history.

(56) References Cited

U.S. PATENT DOCUMENTS

| | | |
|---|---|---|
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | Decant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,505,709 A | 4/1996 | Funderburk et al. |
| 5,497,772 A | 5/1996 | Schulman et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Illiff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,259,937 B1 | 7/2001 | Schulman et al. |

(56) References Cited

U.S. PATENT DOCUMENTS

| | | |
|---|---|---|
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B1 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,204,823 B2 | 4/2007 | Estes et al. |
| 7,396,330 B2 | 7/2008 | Banet et al. |
| 7,651,845 B2 * | 1/2010 | Doyle et al. .................... 435/14 |
| 8,690,856 B2 * | 4/2014 | Blomquist .................... 604/504 |
| 8,758,245 B2 | 6/2014 | Ray et al. |
| 2001/0044731 A1 | 11/2001 | Coffman et al. |
| 2002/0013518 A1 | 1/2002 | West et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2002/0193679 A1 | 12/2002 | Malave et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0171503 A1 * | 8/2005 | Van Den Berghe .. A61M 5/142 604/504 |
| 2005/0192557 A1 | 9/2005 | Brauker et al. |
| 2006/0031094 A1 | 2/2006 | Cohen et al. |
| 2006/0224109 A1 * | 10/2006 | Steil et al. .................... 604/66 |
| 2006/0229694 A1 | 10/2006 | Schulman et al. |
| 2006/0238333 A1 | 10/2006 | Welch et al. |
| 2006/0272652 A1 | 12/2006 | Stocker et al. |
| 2006/0293571 A1 | 12/2006 | Bao et al. |
| 2007/0033074 A1 | 2/2007 | Nitzan et al. |
| 2007/0088521 A1 | 4/2007 | Shmueli et al. |
| 2007/0112298 A1 | 5/2007 | Mueller, Jr. et al. |
| 2007/0135866 A1 | 6/2007 | Baker et al. |
| 2008/0097289 A1 | 4/2008 | Steil et al. |
| 2008/0125701 A1 | 5/2008 | Moberg et al. |
| 2008/0154503 A1 | 6/2008 | Wittenber et al. |
| 2008/0228056 A1 * | 9/2008 | Blomquist et al. ........... 600/365 |
| 2009/0008306 A1 * | 1/2009 | Cicchello ............ A61M 1/1694 210/85 |
| 2009/0081951 A1 | 3/2009 | Erdmann et al. |
| 2009/0082635 A1 | 3/2009 | Baldus et al. |
| 2010/0161236 A1 * | 6/2010 | Cohen ................ G06F 19/3443 702/19 |
| 2010/0174553 A1 | 7/2010 | Kaufman et al. |
| 2010/0249530 A1 * | 9/2010 | Rankers et al. .............. 600/300 |
| 2011/0021898 A1 * | 1/2011 | Wei et al. .................... 600/365 |

FOREIGN PATENT DOCUMENTS

| | | |
|---|---|---|
| CN | 102000372 A | 4/2011 |
| CN | 102395310 A | 3/2012 |
| DE | 4329229 | 3/1995 |
| EP | 0319268 | 11/1988 |
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |
| WO | WO 2011/011739 A2 | 1/2011 |

OTHER PUBLICATIONS (Animas Corporation, 1999). Animas . . . bringing new life to insulin therapy.

Bode B W, et al. (1996). Reduction in Severe Hypoglycemia with Long-Term Continuous Subcutaneous Insulin Infusion in Type I Diabetes. Diabetes Care, vol. 19, No. 4, 324-327.

(56) References Cited

OTHER PUBLICATIONS

Boland E (1998). Teens Pumping it Up! Insulin Pump Therapy Guide for Adolescents. 2nd Edition.
Brackenridge B P (1992). Carbohydrate Gram Counting a Key to Accurate Mealtime Boluses in Intensive Diabetes Therapy. Practical Diabetology, vol. 11, No. 2, pp. 22-28.
Brackenridge, B P et al. (1995). Counting Carbohydrates How to Zero in on Good Control. MiniMed Technologies Inc.
Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.
Hirsch I B et al. (1990). Intensive Insulin Therapy for Treatment of Type I Diabetes. Diabetes Care, vol. 13, No. 12, pp. 1265-1283.
Kulkarni K et al. (1999). Carbohydrate Counting A Primer for Insulin Pump Users to Zero in on Good Control. MiniMed Inc.
Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed•Technologies.
(Intensive Diabetes Management, 1995). Insulin Infusion Pump Therapy. pp. 66-78.
Disetronic My Choice™ D-TRON™ Insulin Pump Reference Manual. (no date).
Disetronic H-TRON® plus Quick Start Manual. (no date).
Disetronic My Choice H-TRONplus Insulin Pump Reference Manual. (no date).
Disetronic H-Tron® plus Reference Manual. (no date).
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump a Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.

(56) References Cited

OTHER PUBLICATIONS

McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.

Monroe, D., "Novel Implantable Glucose Sensors," ACL, Dec. 1989, pp. 8-16.

Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.

Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.

Nakamoto, S., et al., "A Lift-Off Method for Patterning Enzyme-Immobilized Membranes in Multi-Biosensors," Sensors and Actuators 13, 1988, pp. 165-172.

Nishida, Kenro, et al., "Clinical applications of teh wearable artifical endocrine pancreas with the newly designed needle-type glucose sensor," Elsevier Sciences B.V., 1994, pp. 353-358.

Nishida, Kenro, et al., "Development of a ferrocene-mediated needle-type glucose sensor covereed with newly designed biocompatible membrane, 2-methacryloyloxyethylphosphorylcholine -co-n-butyl nethacrylate," Medical Progress Through Technology, vol. 21, 1995, pp. 91-103.

Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.

Reach, G., "A Method for Evaluating in vivo the Functional Characteristics of Glucose Sensors," Biosensors 2, 1986, pp. 211-220.

Shaw, G. W., et al., "In vitro testing of a simply constructed, highly stable glucose sensor suitable for implantation in diabetic patients," Biosensors & Bioelectronics 6, 1991, pp. 401-406.

Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.

Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series Vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Disaccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

* cited by examiner

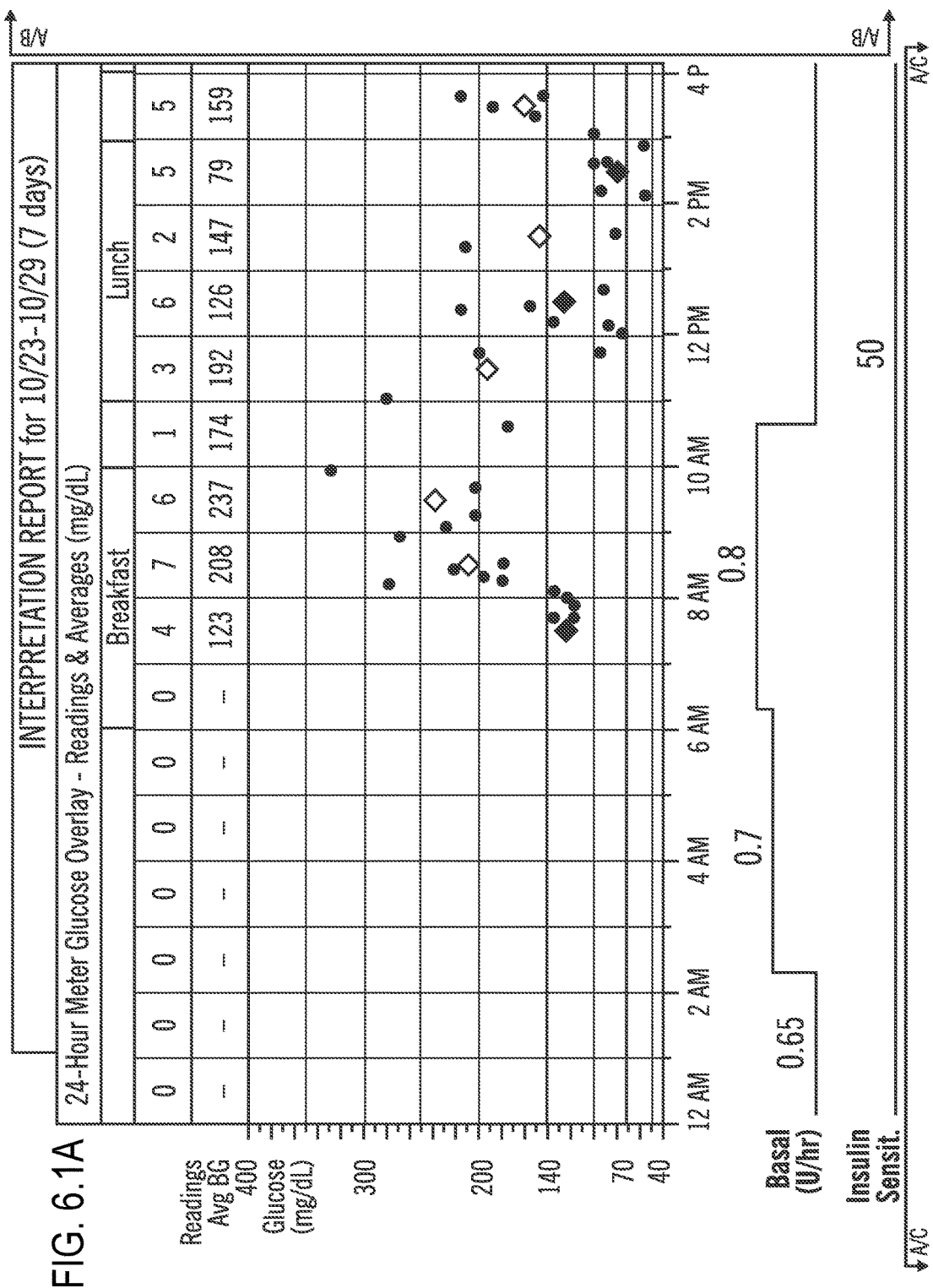
FIG. 6.1A

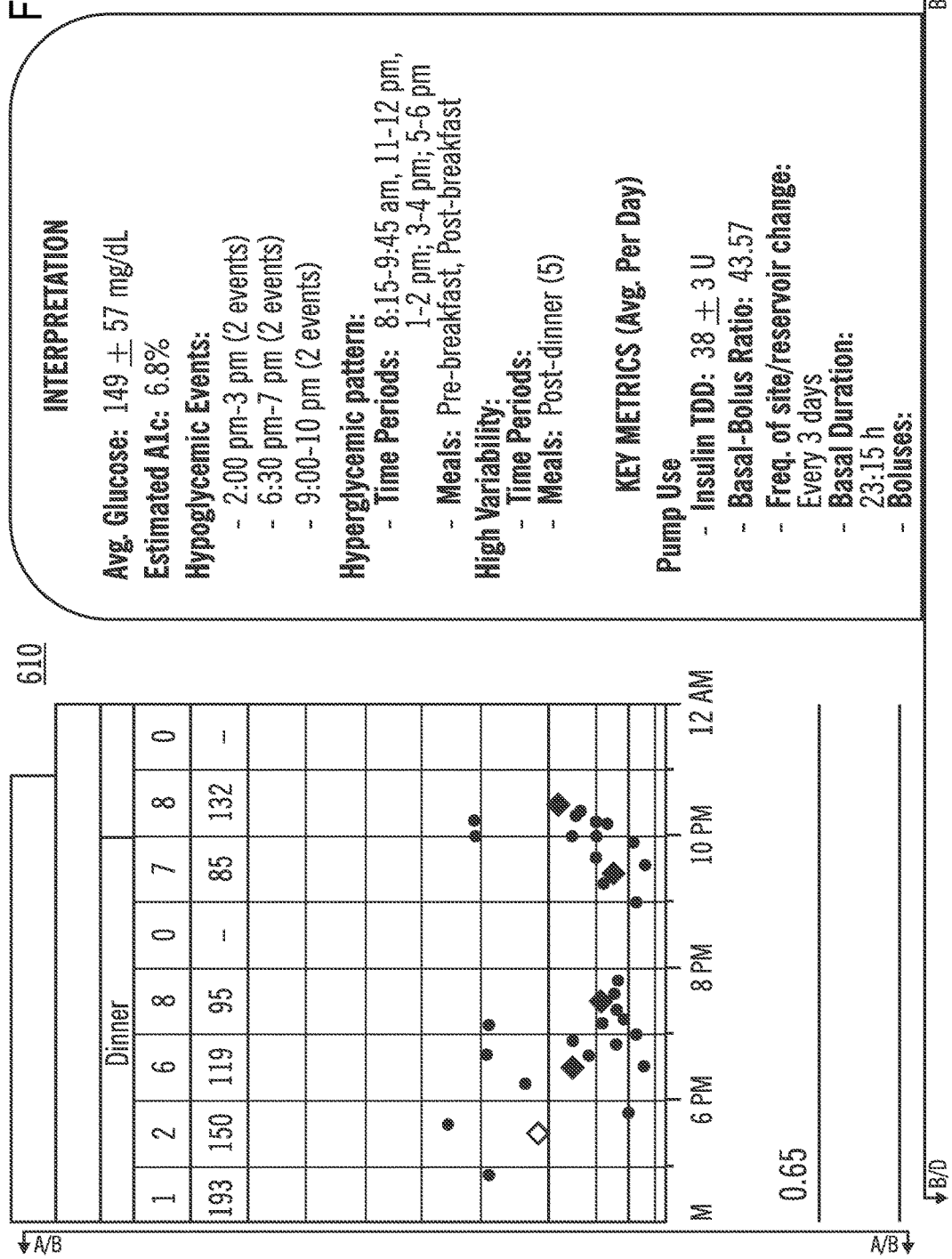
FIG 6.1B

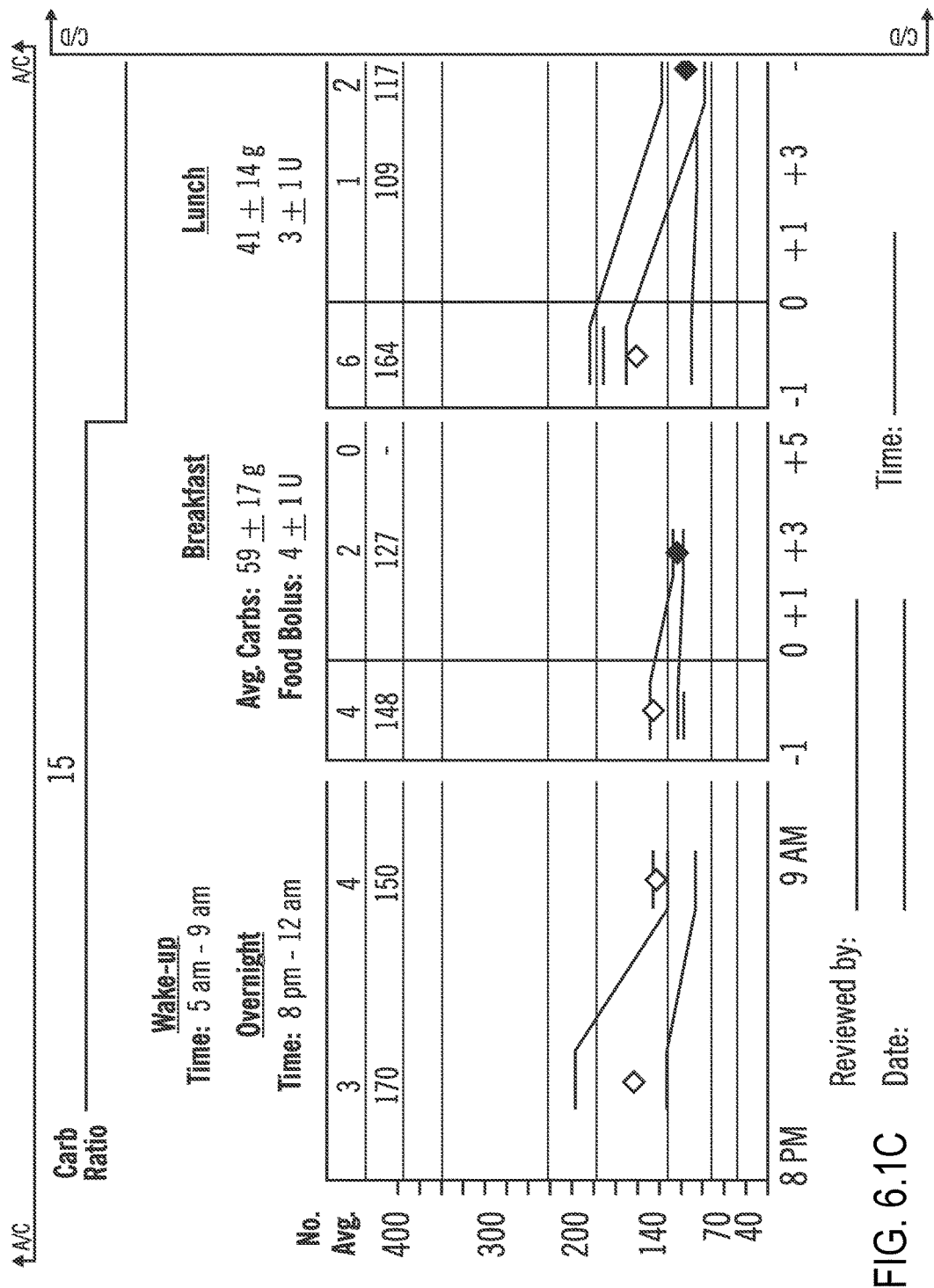
FIG. 6.1C

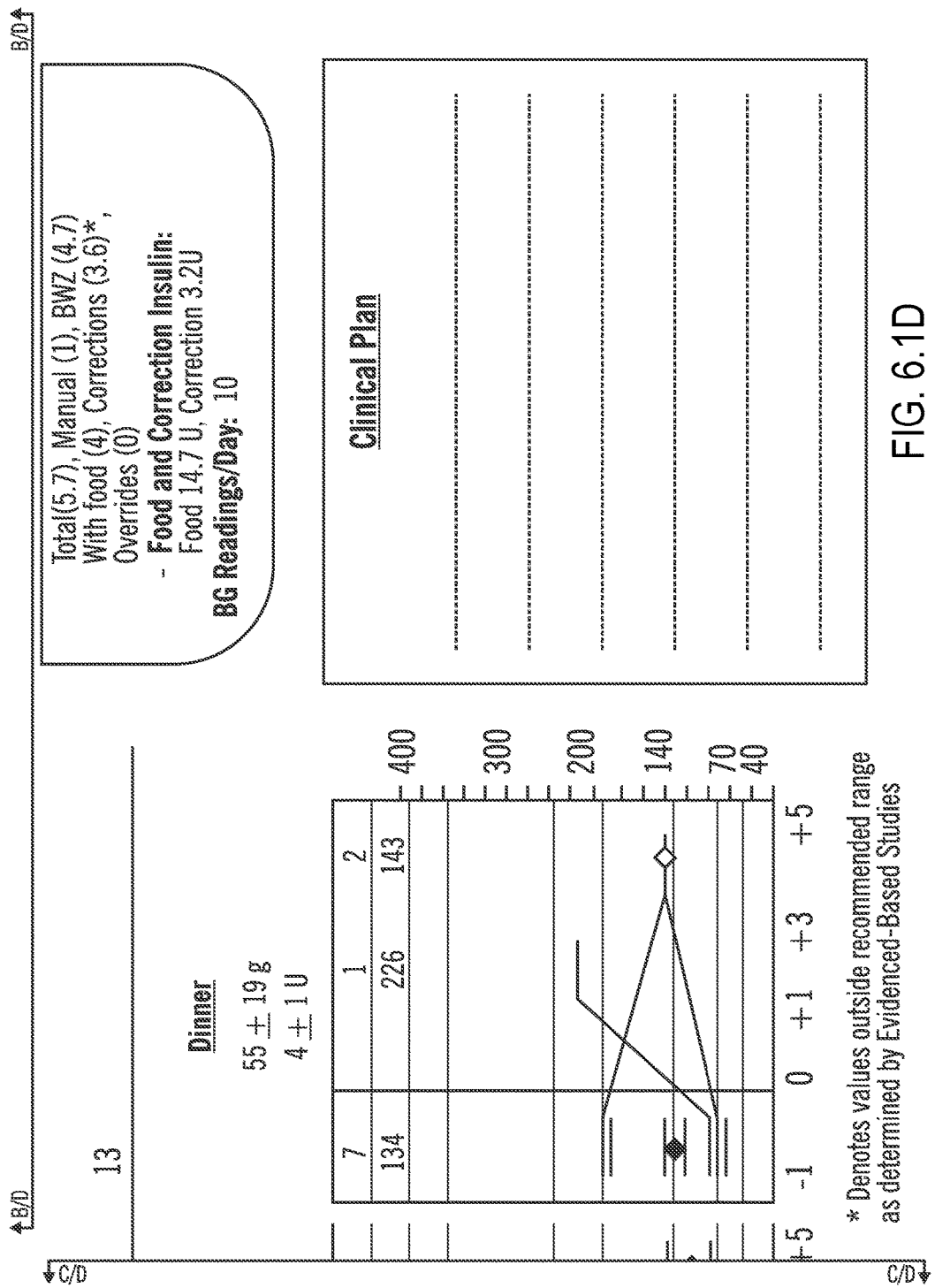
FIG. 6.1D

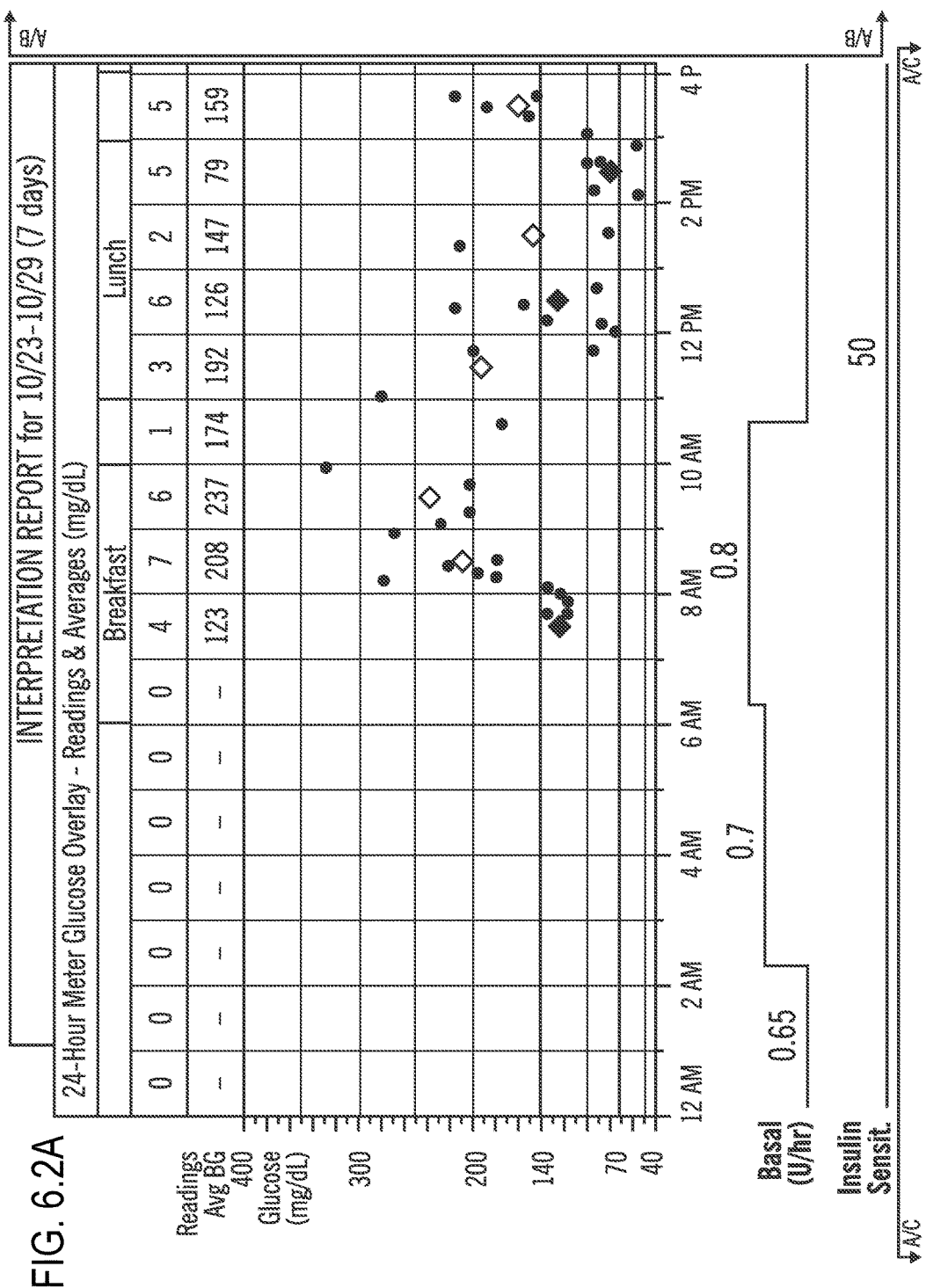
FIG. 6.2A

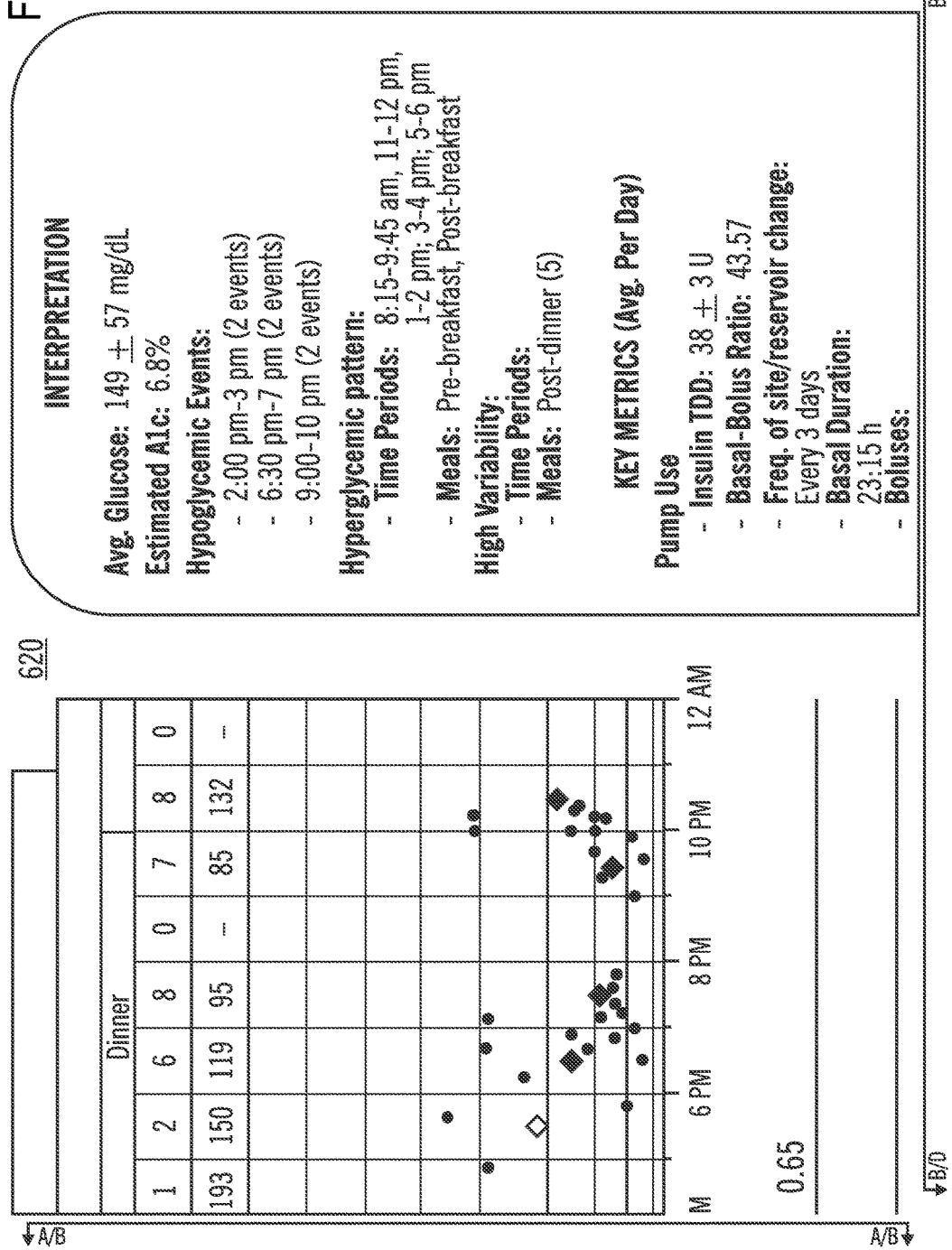
FIG. 6.2B

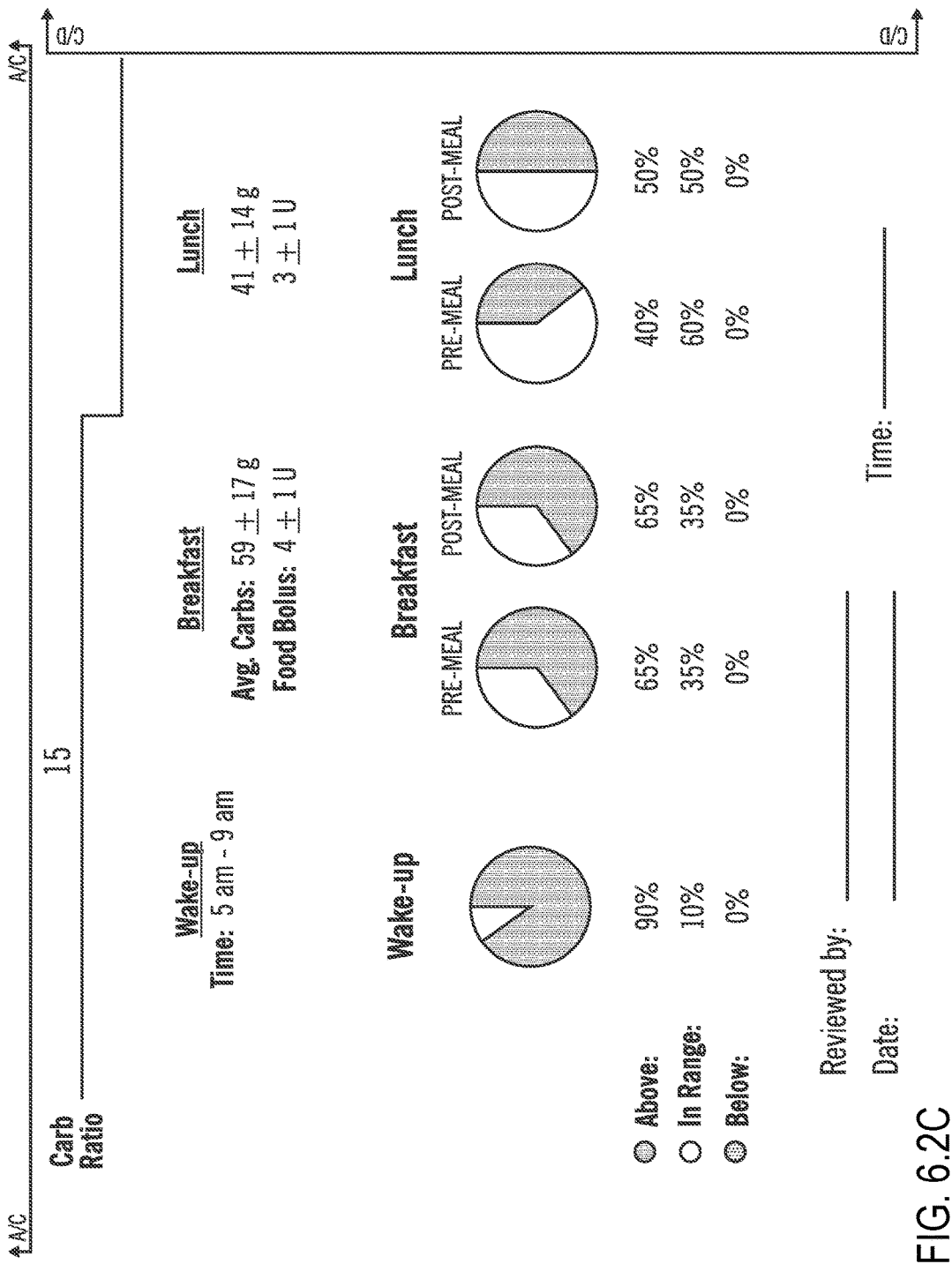
FIG. 6.2C

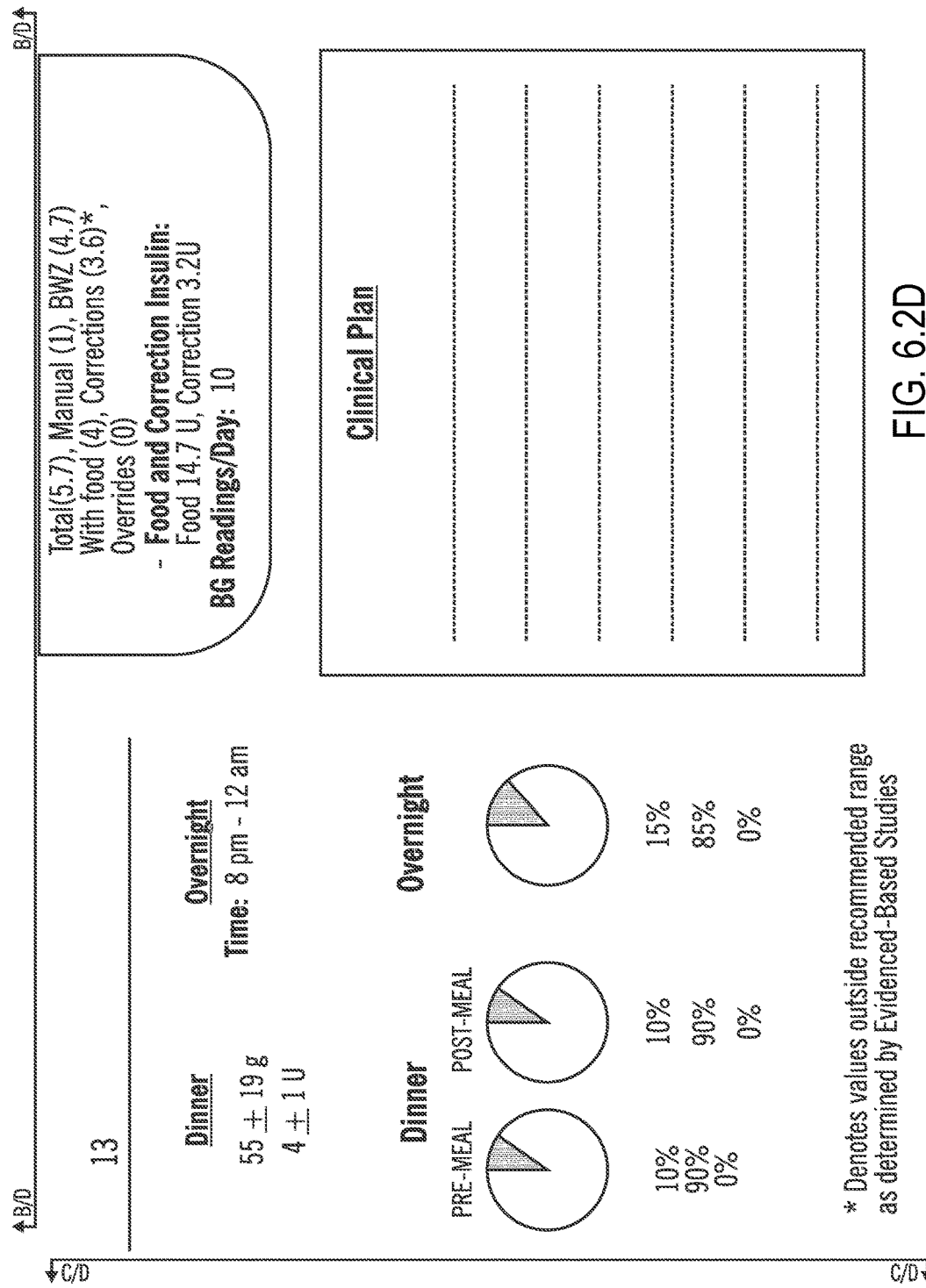
FIG. 6.2D

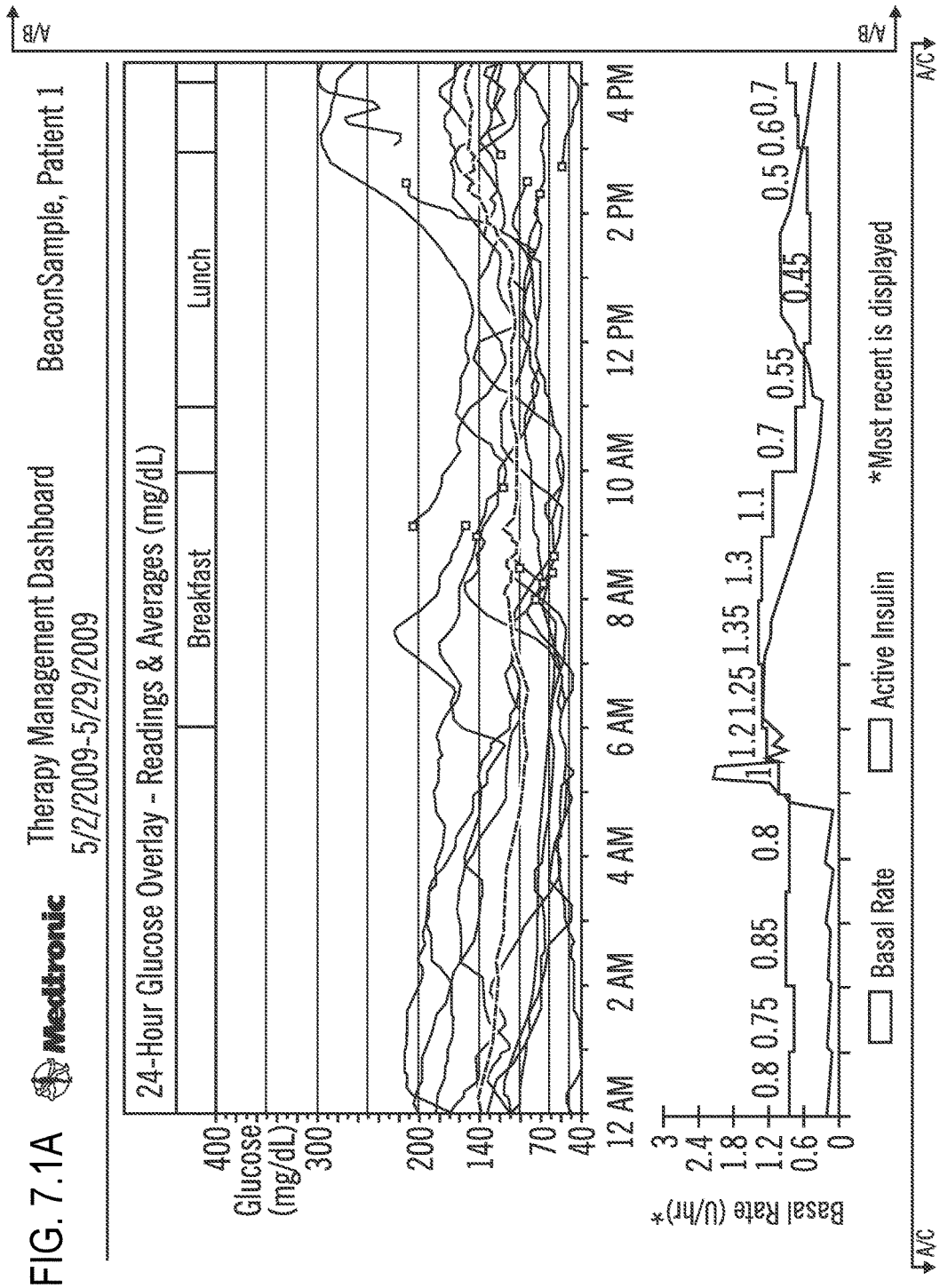
FIG. 7.1A

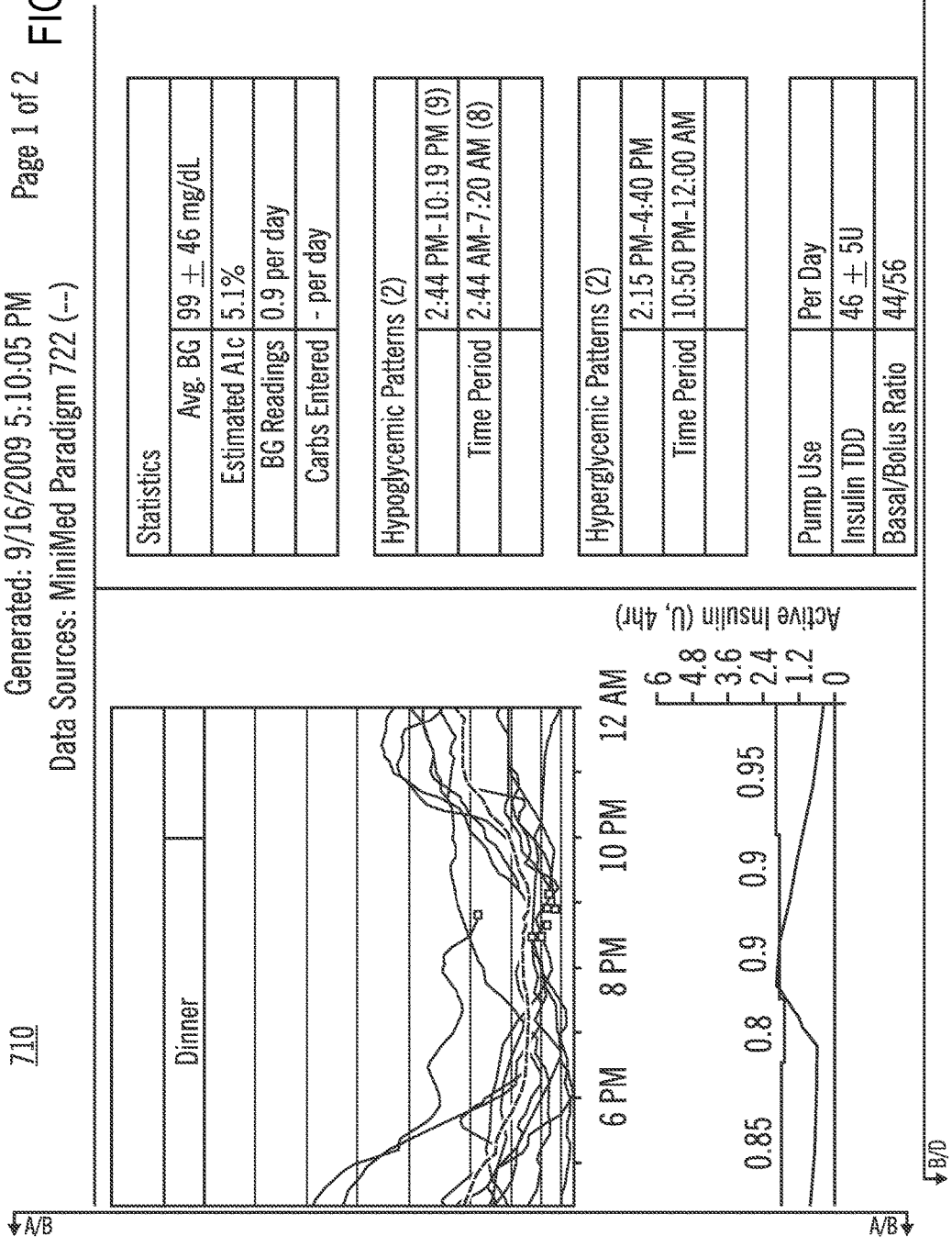
FIG. 7.1B

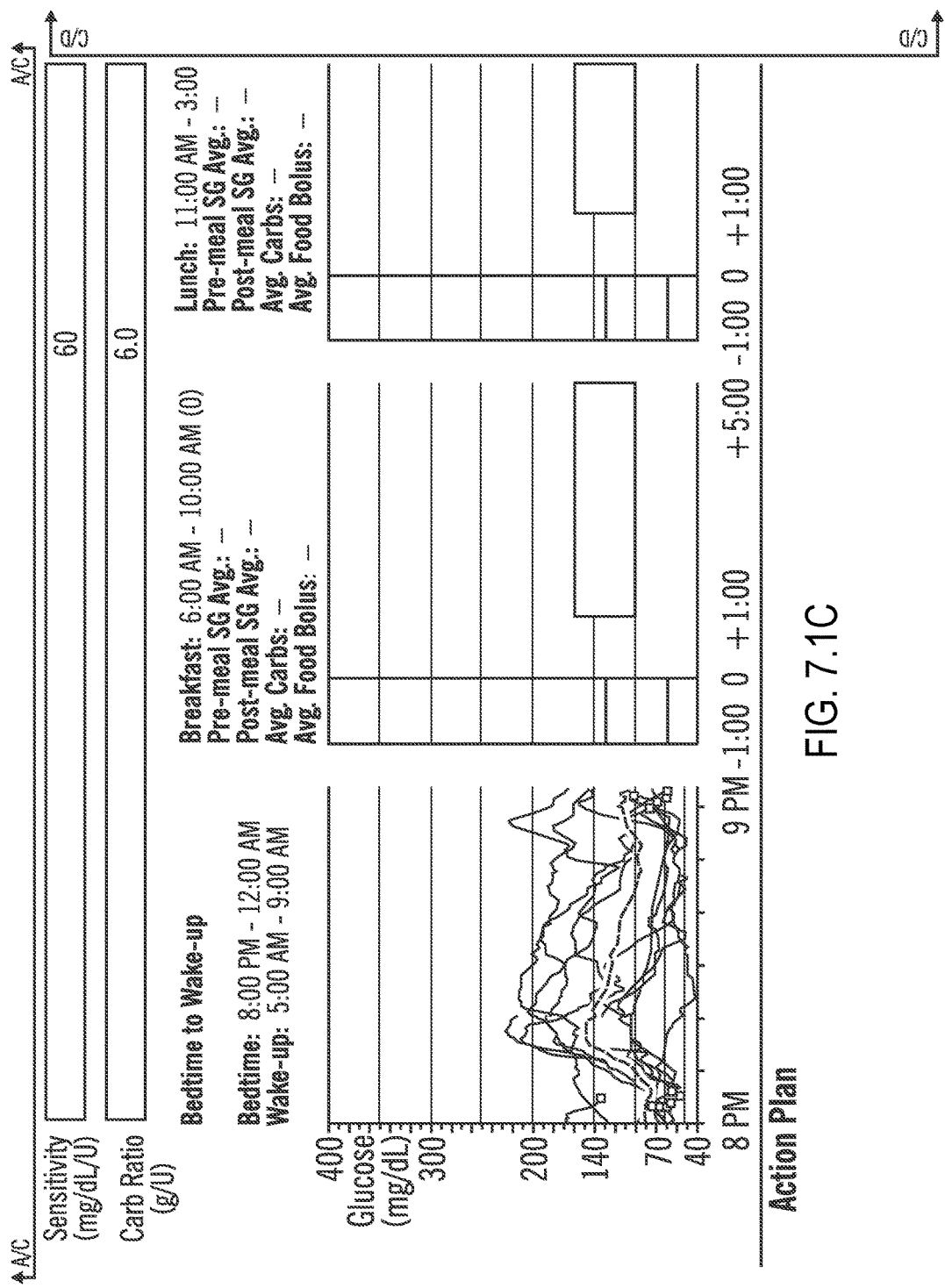
FIG. 7.1C

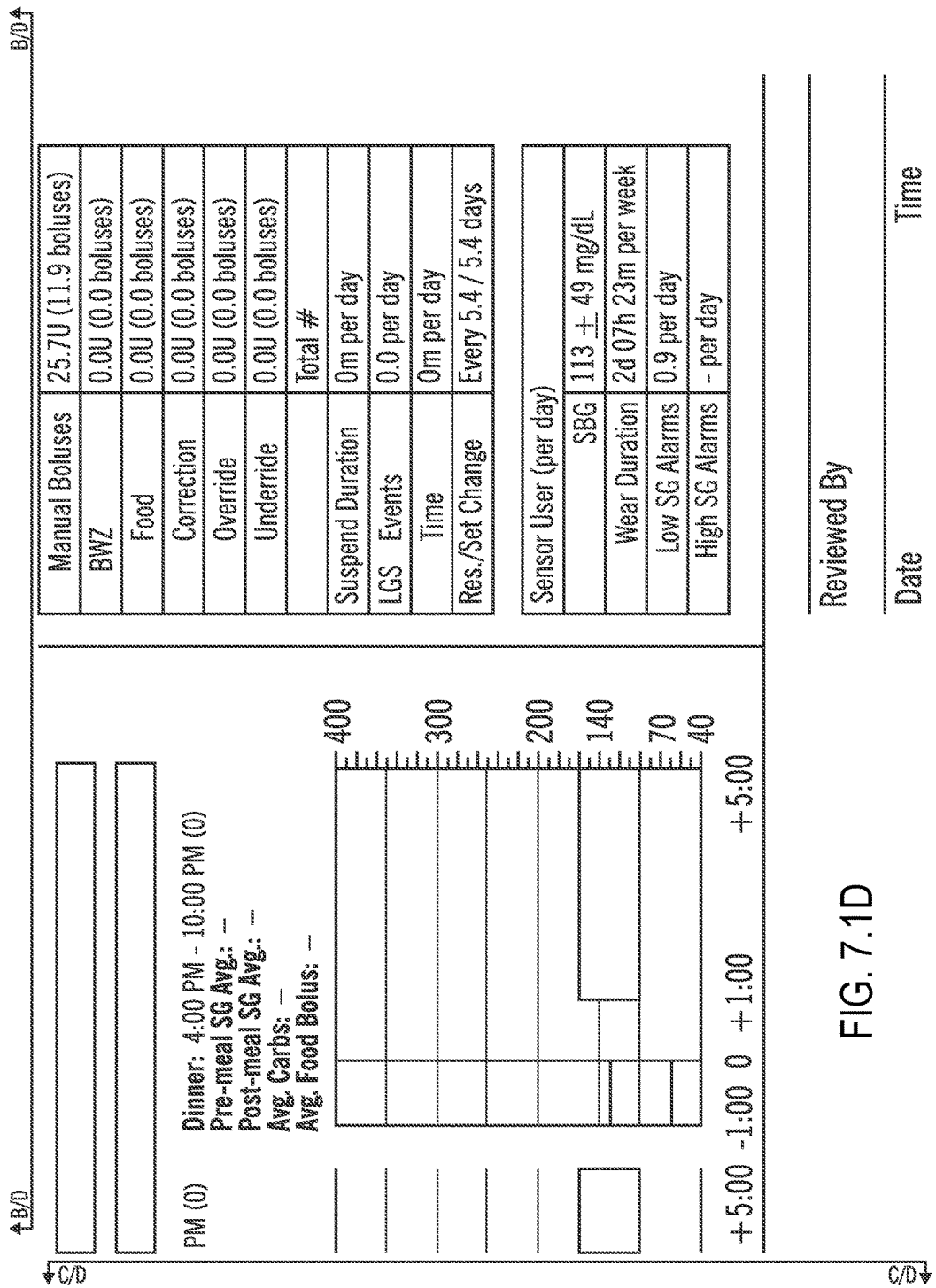
FIG. 7.1D

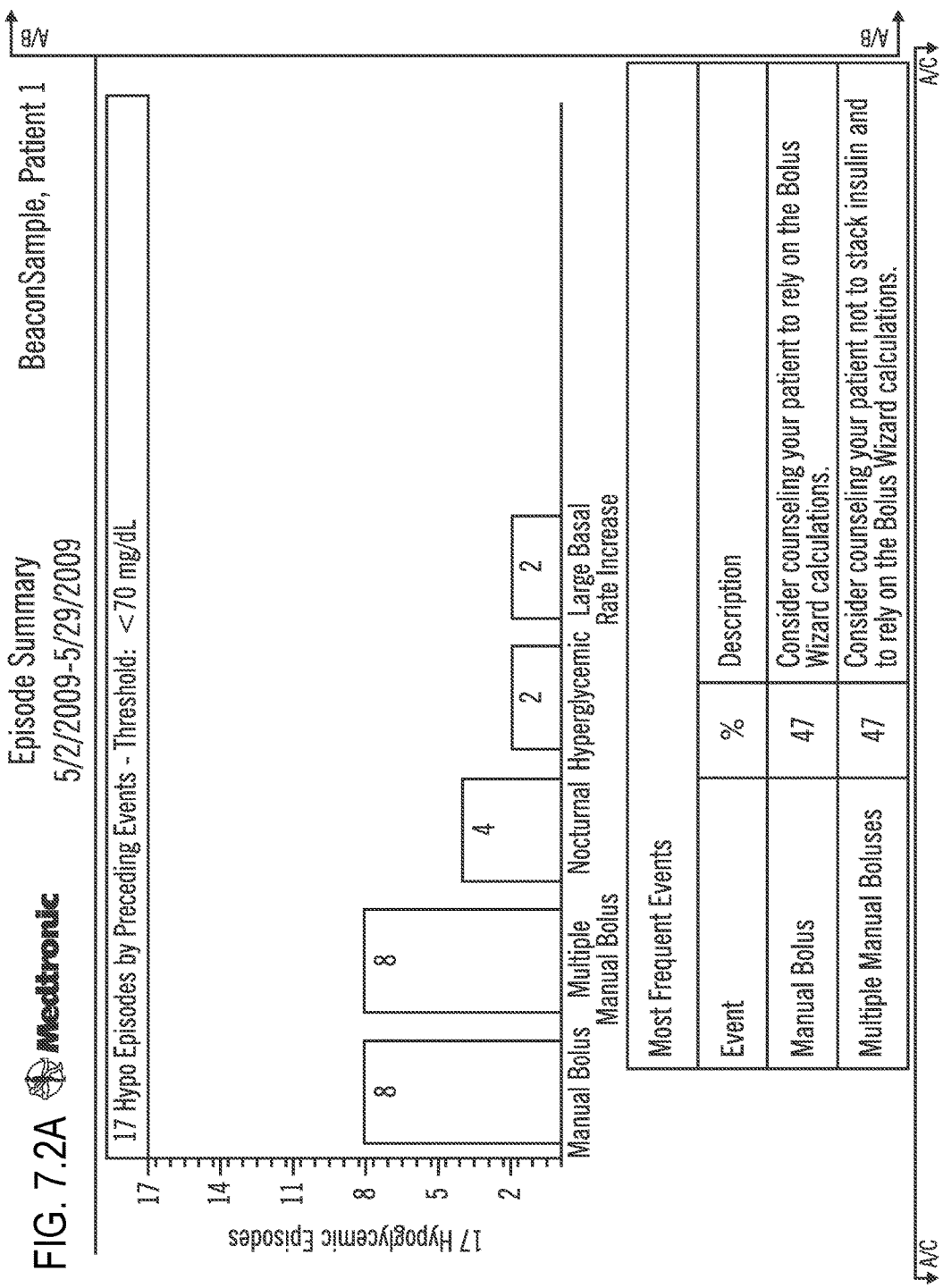

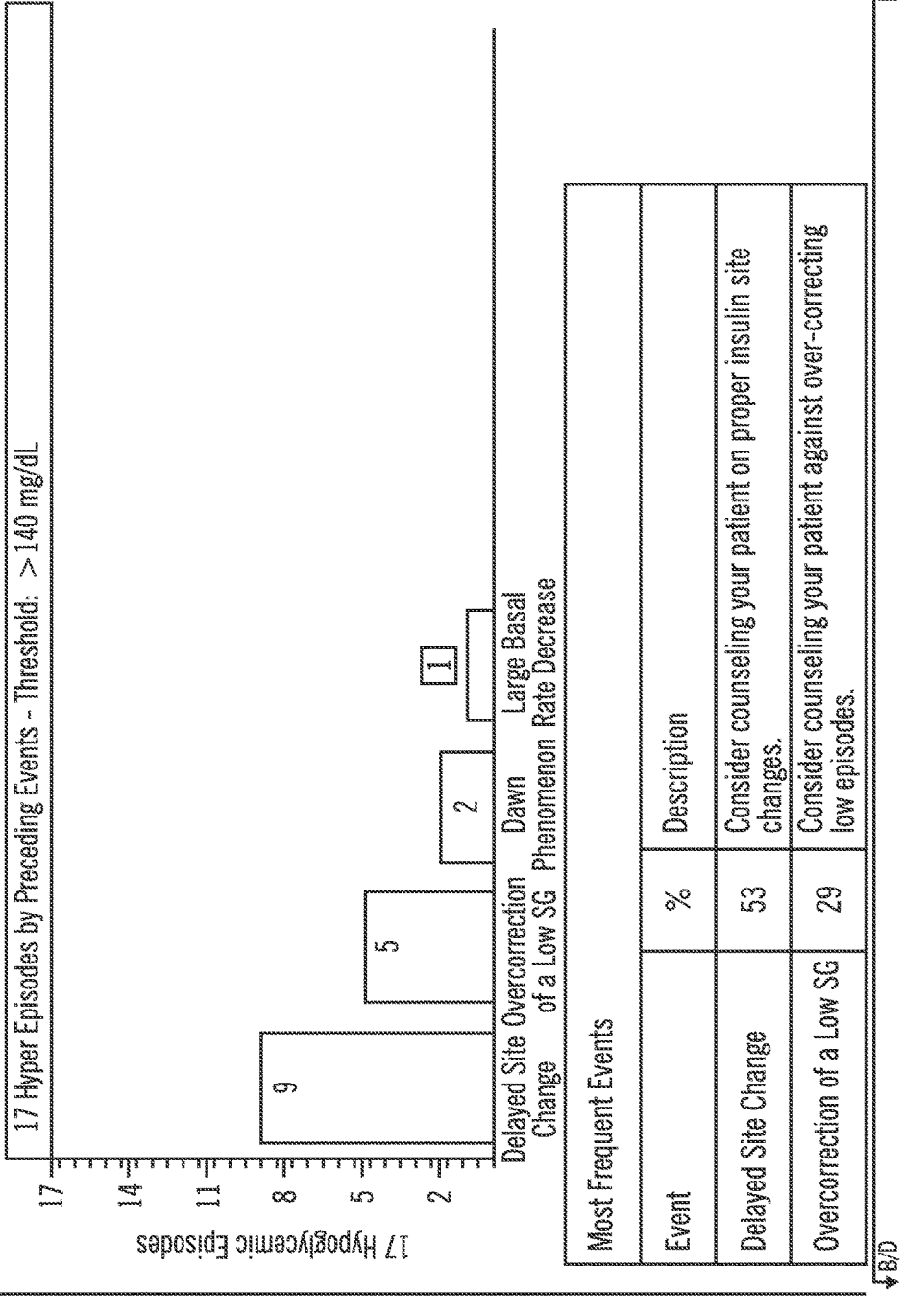
FIG. 7.2B

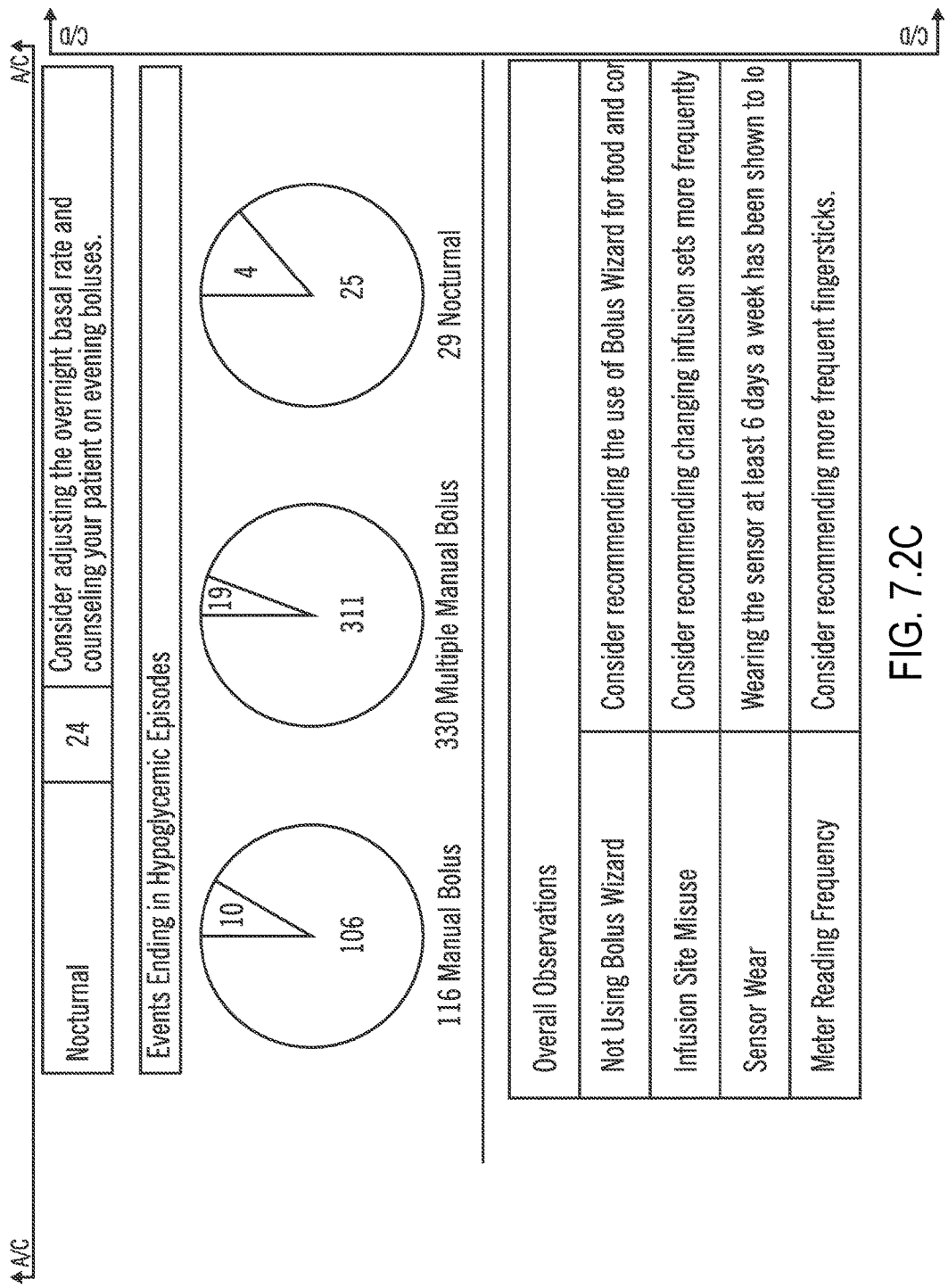
FIG. 7.2C

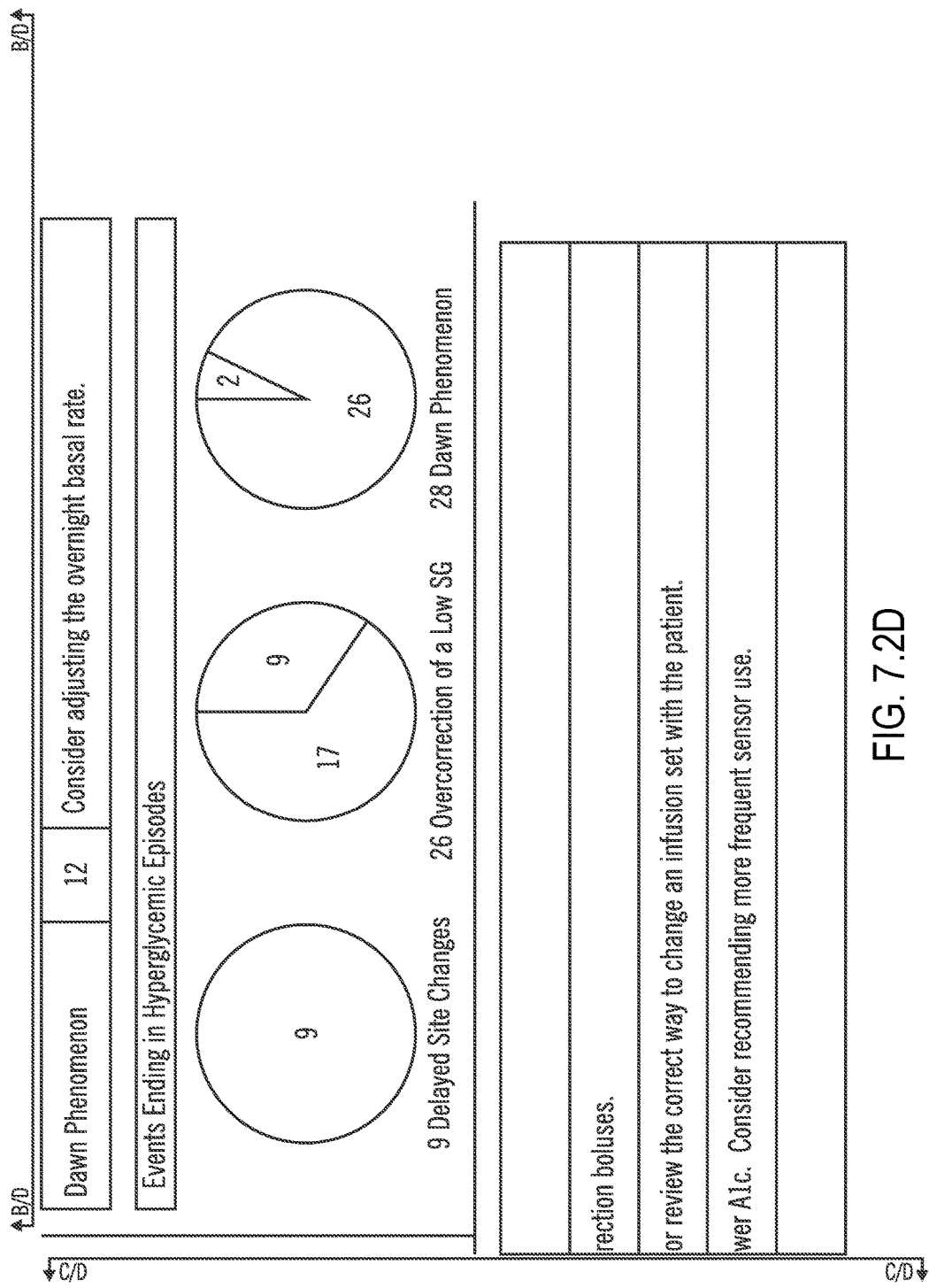
FIG. 7.2D

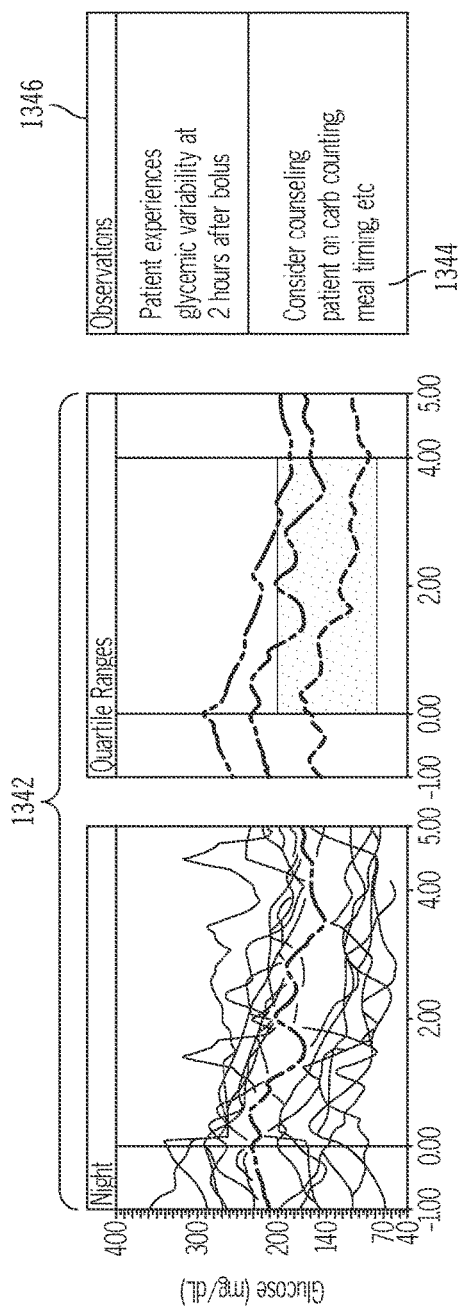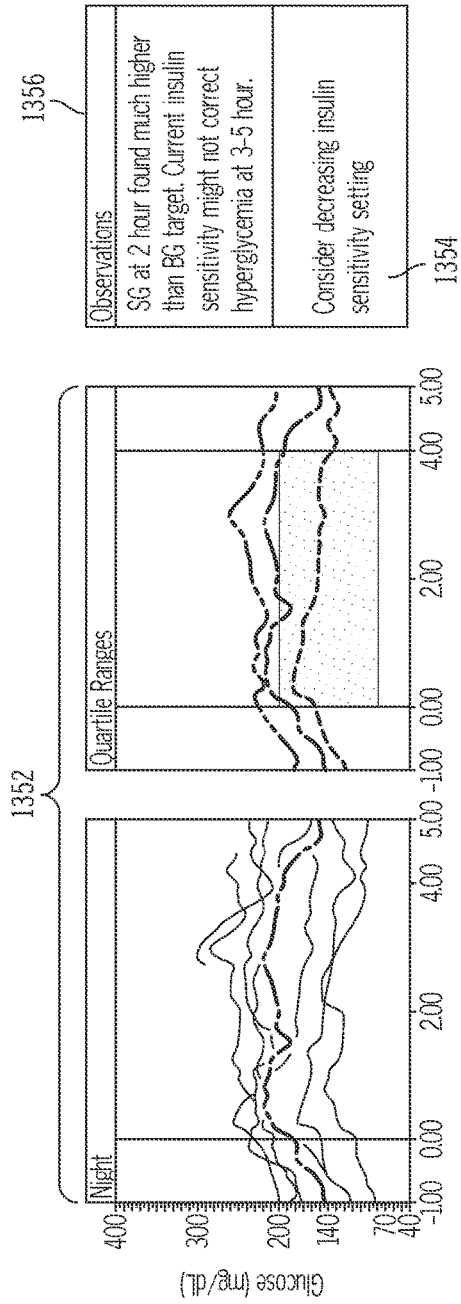

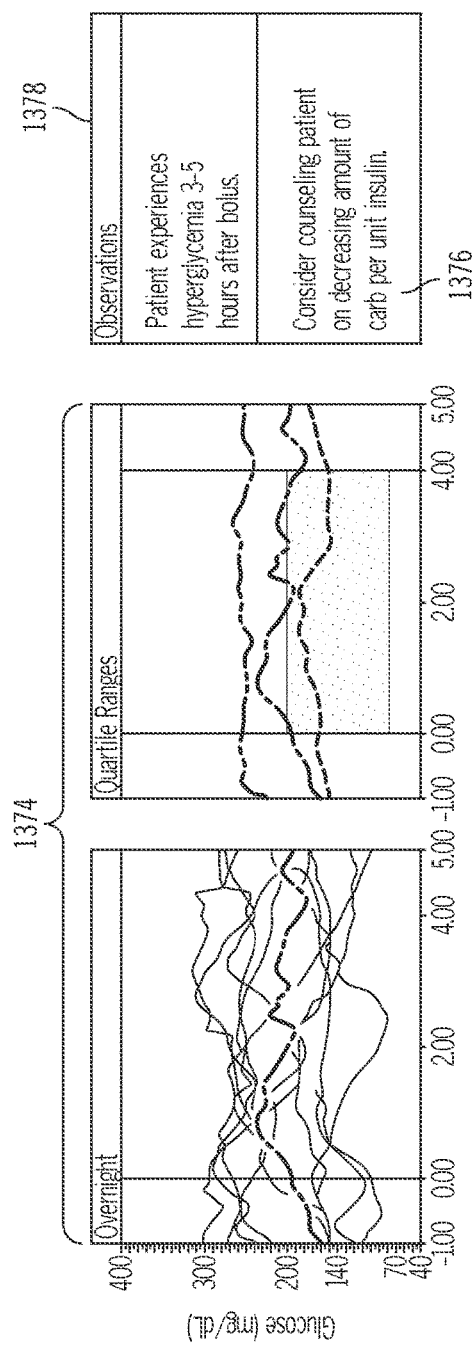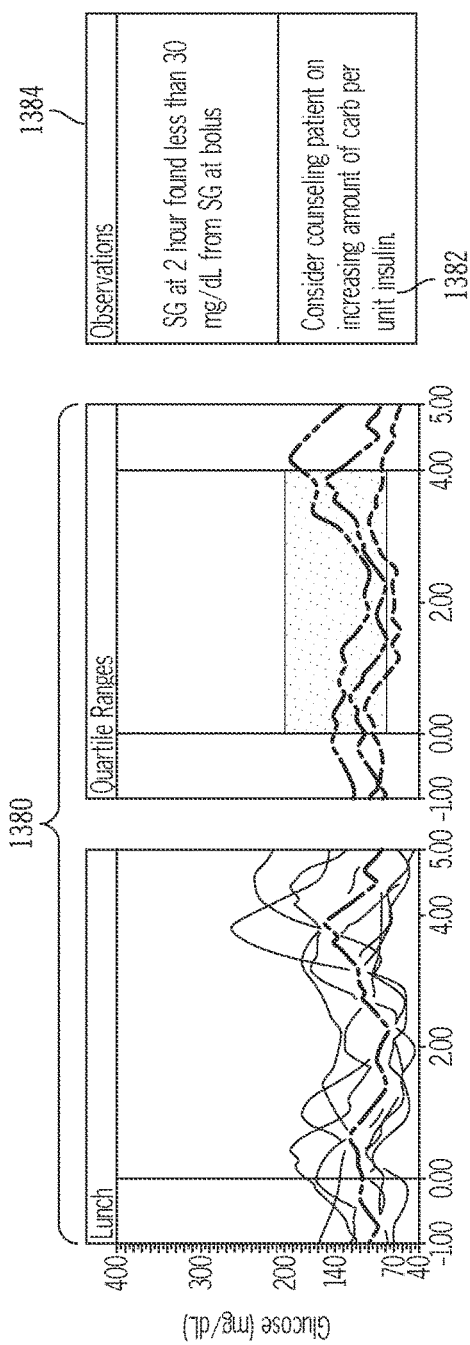
FIG. 26
FIG. 27

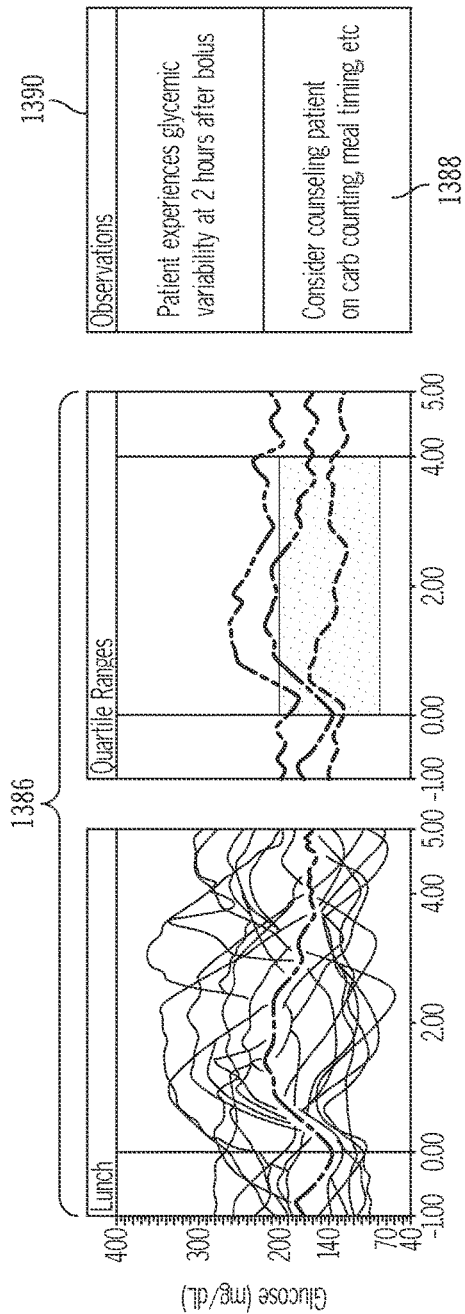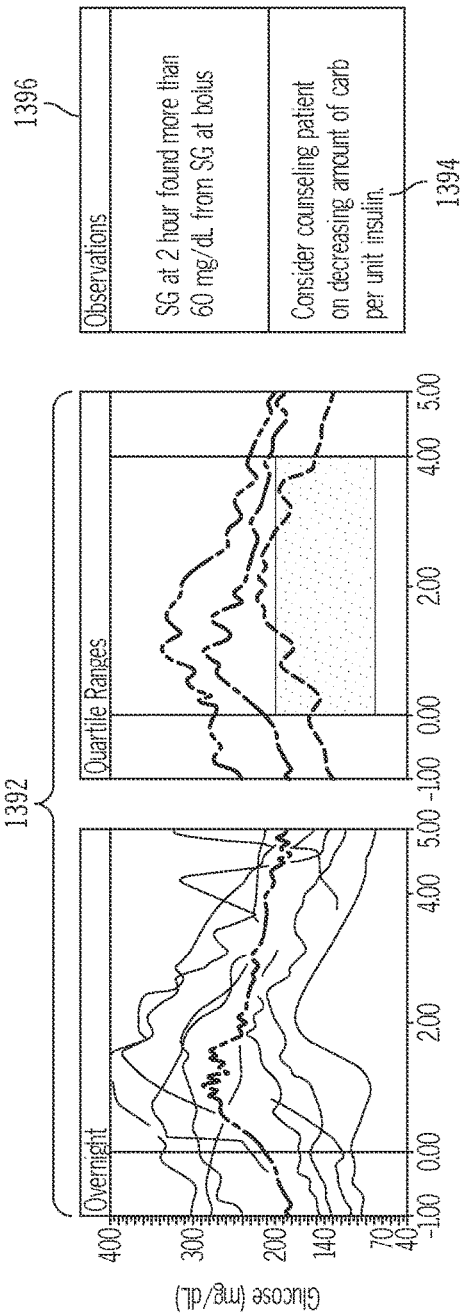

| Weekly Glycemic variability | Overnight 12 AM to 6 AM | | Morning 6 AM to 12 PM | | Afternoon 12 PM to 6 PM | | Evening 6 PM to 12 AM | |
|---|---|---|---|---|---|---|---|---|
| | Hypo (%) | Hyper (%) | Hypo (%) | Hyper (%) | Hypo (%) | Hyper (%) | Hypo (%) | Hyper (%) |
| Monday | 20 | 34 | 20 | 49 | 0 | 38 | 0 | 43 |
| Tuesday | 17 | 25 | 22 | 51 | 11 | 67 | 5 | 69 |
| Wednesday | 8 | 37 | 12 | 28 | 3 | 38 | 0 | 66 |
| Thursday | 0 | 84 | 6 | 71 | 8 | 41 | 0 | 92 |
| Friday | 2 | 48 | 2 | 60 | 5 | 56 | 0 | 50 |
| Saturday | 0 | 50 | 7 | 35 | 7 | 52 | 1 | 78 |
| Sunday | 2 | 60 | 5 | 87 | 5 | 25 | 6 | 53 |

FIG. 34

DIABETES THERAPY MANAGEMENT SYSTEM FOR RECOMMENDING BOLUS CALCULATOR ADJUSTMENTS

CROSS-REFERENCE TO RELATED APPLICATION(S)

This application claims the benefit of U.S. provisional patent application No. 61/656,765, filed Jun. 7, 2012 (the entire content of which is incorporated by reference herein).

TECHNICAL FIELD

Embodiments of the present invention are directed to systems and methods for diabetes therapy management. Specifically, embodiments of the present invention are directed to systems and methods for analyzing patient information to generate reports to assist in the management of diabetes therapy.

BACKGROUND

The pancreas of a normal healthy person produces and releases insulin into the blood stream in response to elevated blood plasma glucose levels. Beta cells (β-cells), which reside in the pancreas, produce and secrete the insulin into the blood stream, as it is needed. If β-cells become incapacitated or die, a condition known as Type I diabetes mellitus (or in some cases if β-cells produce insufficient quantities of insulin, Type II diabetes), then insulin must be provided to the body from another source. Diabetes affects approximately eight percent of the total population in the United States alone.

Traditionally, since insulin cannot be taken orally, insulin has been injected with a syringe. More recently, use of infusion pump therapy has been increasing, especially for delivering insulin for diabetics. For example, external infusion pumps are worn on a belt, in a pocket, or the like, and deliver insulin into the body via an infusion tube with a percutaneous needle or a cannula placed in the subcutaneous tissue.

As of 1995, less than 5% of Type I diabetics in the United States were using infusion pump therapy. Presently, about 10% of the more than 1.5 million Type I diabetics in the U.S. are using infusion pump therapy. And the percentage of Type I diabetics that use an infusion pump is growing at an absolute rate of over 2% each year. Moreover, the number of Type I diabetics is growing at 3% or more per year. In addition, growing numbers of insulin-using Type II diabetics are also using infusion pumps. Physicians have recognized that continuous infusion provides greater control of a diabetic's condition, and are also increasingly prescribing it for patients. Although offering control, pump therapy can suffer from several complications that make use of traditional external infusion pumps less desirable for the user.

BRIEF SUMMARY

Embodiments of the present invention are directed to systems and methods of diabetes analysis. A plurality of glucose level readings for a user is received. A common event occurrence in at least two of the glucose level readings is determined. The at least two glucose level readings from the common event occurrence onwards in time for a time period is analyzed. A glucose level pattern formed by the at least two glucose level readings having a similar shape is determined. At least one anomalous glucose level reading having the similar shape and not conforming to the glucose level pattern is analyzed. The at least one anomalous glucose level reading is adapted to the pattern to form an adapted glucose level pattern. An insulin dosage for the time period beginning at the common event occurrence is calculated based on the adapted glucose level pattern. Embodiments of the present invention may perform these steps on a computer, or any other suitable system.

In particular embodiments, the glucose level readings are at least a portion of a 24-hour period. An average glucose level reading may be calculated from the adapted glucose level pattern, and the insulin dosage may be calculated based on the average glucose level reading. The common event occurrence may be, for example, breakfast, lunch, dinner, a meal bolus, a correction bolus, or a bedtime (to analyze an overnight period). The plurality of glucose level readings may represent glucose levels over time. The insulin dosage may be for a basal insulin dosage. The at least one anomalous glucose level reading having the similar shape may have at least one of: a greater or lesser magnitude, and a higher or lower basal glucose level than the at least two glucose level readings forming the glucose level pattern. The at least one anomalous glucose level reading having the similar shape may be compressed or stretched in time compared to the at least two glucose level readings forming the glucose level pattern. The at least one anomalous glucose level reading having the similar shape may occur differently from the common event occurrence of the at least two glucose level readings forming the glucose level pattern. Moreover, the glucose level readings may exclude those from the most recent days, especially if a user is learning a new behavior. Glucose level readings may be automatically or manually removed from analysis due to transient events in a user's life. Additionally, only those glucose level readings selected from days where the user has a periodic or transient condition (e.g., menstruation, illness, having a cold, being on a particular medication, stress and anxiety, etc.) may be selected for analysis.

Embodiments of the present invention are directed to systems and methods of diabetes analysis. Average glucose level information for a time period over a plurality of days is determined. A current event occurrence is determined. An event occurrence in the average glucose level information within the time period corresponding to the current event occurrence is determined, where the current event occurrence is at a different time of day than the event occurrence. The average glucose level information starting in time from the event occurrence within the time period is analyzed. A notification event in the average glucose level information starting in time from the event occurrence within the time period is determined. A current notification event in time from the current event occurrence based on a time span from the event occurrence to the notification event in the average glucose level information is predicted. An action is initiated in advance of the predicted current notification event. Embodiments of the present invention may perform these steps on a computer, or any other suitable system.

In particular embodiments, the current event occurrence and event occurrence may be, for example, breakfast, lunch, or dinner. The notification event may include, for example, hyperglycemia, hypoglycemia, a sharp glucose level spike, or a sharp glucose level drop. The action may include at least one of notifying a user of the predicted current notification event (which may utilize an auditory, visual, or vibrational alarm), recommending a bolus dosage to the user, automatically delivering a bolus of insulin, and automatically suspending delivery of insulin. The current event occurrence may be earlier or later than the event occurrence in the average glucose level information.

Embodiments of the present invention are directed to a method of providing bolus dosage recommendations for diabetics. A plurality of representative foods is presented to a user. The user's response to estimate a carbohydrate value for each one of the plurality of representative foods is received. An input is received from the user indicating a food to be consumed and an estimated carbohydrate value for the food to be consumed. A bolus dosage recommendation is calculated based on the input from the user and the user's response to estimate the carbohydrate value for at least one of the plurality of representative foods. Embodiments of the present invention may perform these steps on a computer, or any other suitable system.

In particular embodiments, the bolus dosage recommendation is increased if the user's response to estimate the carbohydrate value for the at least one of the plurality of representative foods corresponding to the food to be consumed is lower than a true carbohydrate value for the at least one of the plurality of representative foods corresponding to the food to be consumed, and the bolus dosage recommendation is decreased if the user's response to estimate the carbohydrate value for the at least one of the plurality of representative foods corresponding to the food to be consumed is higher than a true carbohydrate value for the at least one of the plurality of representative foods corresponding to the food to be consumed. The plurality of representative foods may include a plurality of food types, and the plurality of food types may include: grains, vegetables, fruits, dairy products, and meats.

Embodiments of the present invention are directed to a method of diabetes analysis. A plurality of glucose level readings for a user is received. The plurality of blood glucose level readings are analyzed to generate a report. The report includes a first chart along a 24-hour timeline indicating the plurality of glucose level readings, and a second chart having at least one of infusion device settings and active insulin levels corresponding to the 24-hour timeline of the first chart.

In particular embodiments, the plurality of glucose level readings may be blood glucose level readings taken from a blood glucose meter. The plurality of glucose level readings may be continuous blood glucose level readings received from a continuous glucose monitor sensor. The second chart further may include an interpretation report. The infusion device settings may include at least one of basal rate, insulin sensitivity, and carbohydrate ratio. The second chart further may include basal rate information corresponding to the 24-hour timeline of the first chart.

Embodiments of the present invention are directed to an article of manufacture containing code for diabetes analysis, comprising a computer-usable medium including at least one embedded computer program that is capable of causing at least one computer to perform receiving a plurality of glucose level readings for a user, and analyzing the plurality of blood glucose level readings to generate a report. The report includes a first chart along a 24-hour timeline indicating the plurality of glucose level readings, and a second chart having at least one of infusion device settings and active insulin levels corresponding to the 24-hour timeline of the first chart.

In particular embodiments, the plurality of glucose level readings may be blood glucose level readings taken from a blood glucose meter. The plurality of glucose level readings may be continuous blood glucose level readings received from a continuous glucose monitor sensor. The second chart further may include an interpretation report. The infusion device settings may include at least one of basal rate, insulin sensitivity, and carbohydrate ratio. The second chart further may include basal rate information corresponding to the 24-hour timeline of the first chart.

An exemplary embodiment of an electronic computing device is also disclosed. The device includes a processor device and at least one memory element associated with the processor device. The memory element stores processor executable instructions that, when executed by the processor device, perform a method of managing use of an insulin infusion device. The method receives glucose data for a user of the insulin infusion device, the glucose data indicating blood glucose levels of the user for a specified period of time during which the insulin infusion device is regulating delivery of insulin to the user. The method continues by analyzing the received glucose data for presence of any of a plurality of event occurrences indicative of a correctable basal rate setting of the insulin infusion device, and detecting at least one of the plurality of event occurrences. The method continues by outputting a recommendation to adjust the basal rate setting of the insulin infusion device, wherein the recommendation is associated with the one or more detected event occurrences.

Also provided is a tangible and non-transitory electronic storage medium having processor executable instructions that, when executed by a processor device, perform a method of managing use of an insulin infusion device. The method analyzes glucose data for a user of the insulin infusion device for presence of any of a plurality of event occurrences indicative of a correctable basal rate setting of the insulin infusion device. The glucose data indicates blood glucose levels of the user for a specified period of time during which the insulin infusion device is regulating delivery of insulin to the user. The method continues by detecting at least one of the plurality of event occurrences, and outputting a recommendation to adjust the basal rate setting of the insulin infusion device, wherein content of the recommendation is based on the one or more detected event occurrences.

Another embodiment of an electronic computing device is also provided. The device includes a device communications layer that receives sensor data for a user of an insulin infusion device. The sensor data indicates blood glucose levels of the user for a specified period of time, and over a plurality of days. The device also includes a processor device that analyzes the received sensor data to detect an event occurrence indicative of a correctable basal rate setting of the insulin infusion device. The device also includes a reporting layer that generates a report comprising a graphical representation of the received sensor data and a recommendation to adjust a basal rate setting of the insulin infusion device. The recommendation is intended to address the detected event occurrence.

Another embodiment of an electronic computing device is also provided. The device includes a processor device and at least one memory element associated with the processor device. The memory element stores processor executable instructions that, when executed by the processor device, perform a method of managing use of an insulin infusion device. The method begins by receiving glucose data for a user of the insulin infusion device, the glucose data indicating blood glucose levels of the user for a period of time during which the insulin infusion device is regulating delivery of insulin to the user. The method continues by reviewing the received glucose data to identify bolus calculator event data corresponding to use of a bolus calculator of the insulin infusion device, wherein the bolus calculator calculates each bolus dosage recommendation based on a respective user entered carbohydrate consumption value, a respective user entered current blood glucose value, and a user specific bolus calculator setting. The method continues by analyzing the identified bolus calculator event data to detect one of a plurality of event occurrences indicative of potential maladjustment of the user specific bolus calculator setting, and outputting a recommendation to adjust the user specific bolus calculator setting of the insulin infusion device, wherein the recommendation is associated with the detected event occurrence.

Also disclosed herein is a tangible and non-transitory electronic storage medium having processor executable instructions that, when executed by a processor device, perform an exemplary embodiment of a method of managing use of an insulin infusion device. The method begins by identifying bolus calculator event data from glucose data for a user of the insulin infusion device, the identified bolus calculator event data corresponding to use of a bolus calculator of the insulin infusion device, wherein the bolus calculator calculates each bolus dosage recommendation based on a respective user entered carbohydrate consumption value, a respective user entered current blood glucose value, and a user specific bolus calculator setting. The method continues by analyzing the identified bolus calculator event data to detect an event occurrence that is indicative of potential maladjustment of the user specific bolus calculator setting, and outputting a recommendation to adjust the user specific bolus calculator setting of the insulin infusion device, wherein the recommendation is associated with the detected event occurrence.

An exemplary embodiment of a method of managing use of an insulin infusion device is also disclosed. The method identifies bolus calculator event data from glucose data for a user of the insulin infusion device, wherein the identified bolus calculator event data corresponds to use of a bolus calculator of the insulin infusion device, and wherein the bolus calculator calculates each bolus dosage recommendation based on a respective user entered carbohydrate consumption value, a respective user entered current blood glucose value, a user specific carbohydrate ratio value, and a user specific insulin sensitivity value. The method continues by filtering the identified bolus calculator event data to remove glucose data associated with an override of a bolus dosage recommendation, an active insulin condition, or a back to back bolus condition. The filtered bolus calculator event data is analyzed to detect an event occurrence that is indicative of potential maladjustment of the user specific carbohydrate ratio value or the user specific insulin sensitivity value. The method continues by outputting a recommendation to adjust the user specific carbohydrate ratio value or the user specific insulin sensitivity value, based on characteristics of the detected event occurrence.

Another embodiment of a method of managing use of an insulin infusion device is also provided. The method receives glucose data for a user of the insulin infusion device, the glucose data indicating blood glucose levels of the user for a specified period of time during which the insulin infusion device is regulating delivery of insulin to the user. The method continues by analyzing the received glucose data for presence of any of a plurality of event occurrences indicative of a correctable basal rate setting of the insulin infusion device, and detecting at least one of the plurality of event occurrences. The method continues by outputting a recommendation to adjust the basal rate setting of the insulin infusion device, wherein the recommendation is associated with the one or more detected event occurrences.

An embodiment of a processor based computer system is also provided. The system includes a device communications layer that receives glucose data for a user of an insulin infusion device. The glucose data indicates blood glucose levels of the user for a specified period of time during which the insulin infusion device is regulating delivery of insulin to the user. The system also includes a processor device that analyzes the received glucose data for presence of any of a plurality of event occurrences indicative of a correctable basal rate setting of the insulin infusion device. The processor device detects, in response to the analyzing, at least one of the plurality of event occurrences, to determine one or more detected event occurrences. The system also includes a reporting layer that outputs a recommendation to adjust the basal rate setting of the insulin infusion device, wherein the recommendation is associated with the one or more detected event occurrences.

An exemplary embodiment of a method of managing use of an insulin infusion device is also disclosed. The method involves receiving glucose data for a user of the insulin infusion device, the glucose data indicating blood glucose levels of the user for a period of time during which the insulin infusion device is regulating delivery of insulin to the user. The method proceeds by reviewing the received glucose data to identify bolus calculator event data corresponding to use of a bolus calculator of the insulin infusion device, wherein the bolus calculator calculates each bolus dosage recommendation based on a respective user entered carbohydrate consumption value, a respective user entered current blood glucose value, and a user specific bolus calculator setting. The method continues by analyzing the identified bolus calculator event data to detect one of a plurality of event occurrences indicative of potential maladjustment of the user specific bolus calculator setting, and outputting a recommendation to adjust the user specific bolus calculator setting of the insulin infusion device, wherein the recommendation is associated with the detected event occurrence.

Another embodiment of a processor based computer system is also provided. The system includes a device communications layer configured to receive glucose data for a user of an insulin infusion device, the glucose data indicating blood glucose levels of the user for a period of time during which the insulin infusion device is regulating delivery of insulin to the user. The system also includes a processor device that reviews the received glucose data to identify bolus calculator event data corresponding to use of a bolus calculator of the insulin infusion device, wherein the bolus calculator calculates each bolus dosage recommendation based on a respective user entered carbohydrate consumption value, a respective user entered current blood glucose value, and a user specific bolus calculator setting. The processor device analyzes the identified bolus calculator event data to detect one of a plurality of event occurrences indicative of potential maladjustment of the user specific bolus calculator setting. The system also includes a reporting layer that outputs a recommendation to adjust the user specific bolus calculator setting of the insulin infusion device, wherein the recommendation is associated with the detected event occurrence.

BRIEF DESCRIPTION OF THE DRAWINGS

FIGS. 6.1 (which is split into FIGS. 6.1A, 6.1B, 6.1C, and 6.1D) and 6.2 (which is split into FIGS. 6.2A, 6.2B, 6.2C, and 6.2D) illustrate Interpretation Reports according to embodiments of the present invention;

FIG. 7.1 (which is split into FIGS. 7.1A, 7.1B, 7.1C, and 7.1D) illustrates a Therapy Management Dashboard according to embodiments of the present invention;

FIG. 7.2 (which is split into FIGS. 7.2A, 7.2B, 7.2C, and 7.2D) illustrates an Episode Summary according to embodiments of the present invention;

FIG. 22 depicts glucose data for a correction bolus event and a corresponding recommendation related to a glycemic variability condition;

FIG. 23 depicts glucose data for a correction bolus event and a corresponding recommendation related to an increasing glucose condition;

FIG. 26 depicts glucose data for a food bolus event and a corresponding recommendation related to a hyperglycemic condition;

FIG. 27 depicts glucose data for a food bolus event and a corresponding recommendation related to a limited glucose increase condition;

FIG. 28 depicts glucose data for a food bolus event and a corresponding recommendation related to an early glycemic variability condition;

FIG. 29 depicts glucose data for a food bolus event and a corresponding recommendation related to a large glucose increase condition;

FIG. 34 illustrates a weekly glycemic variability report of the type that may be found in the glucose trend summary report.

DETAILED DESCRIPTION

Embodiments of the invention are described below with reference to flowchart and menu illustrations of methods, apparatus, and computer program products. It will be understood that each block of the flowchart illustrations, and combinations of blocks in the flowchart illustrations, can be implemented by computer program instructions (as can any menu screens described in the Figures). These computer program instructions may be loaded onto a computer or other programmable data processing apparatus to produce a machine, such that the instructions which execute on the computer (or other programmable data processing apparatus) create instructions for implementing the functions specified in the flowchart block or blocks. These computer program instructions may also be stored in a computer-readable memory that can direct a computer (or other programmable data processing apparatus) to function in a particular manner, such that the instructions stored in the computer-readable memory produce an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks, and/or menus presented herein.

Figure 1:
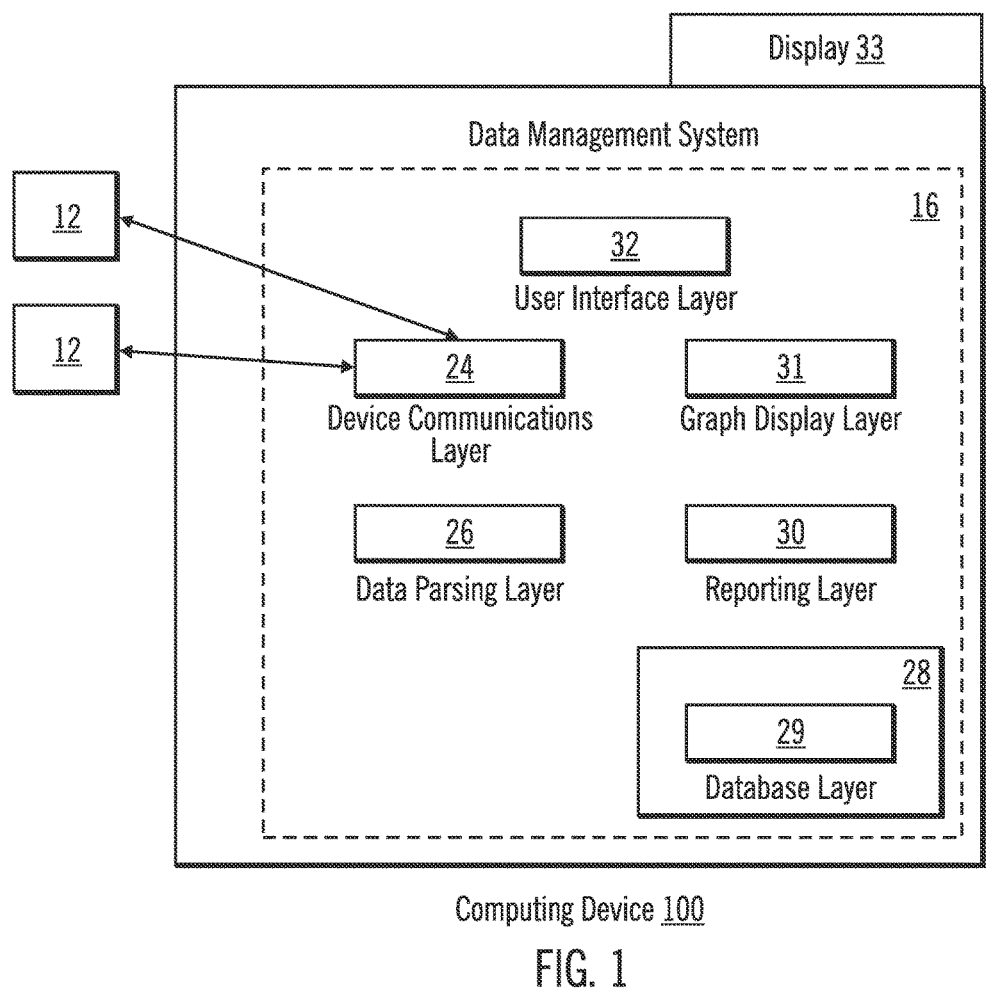
FIG. 1 illustrates a computing device including a display housing a diabetes data management system according to embodiments of the present invention.

FIG. 1 illustrates a computing device including a display housing a diabetes data management system according to embodiments of the present invention. The diabetes data management system (DDMS) may be referred to as the Medtronic MiniMed CARELINK™ system or as a medical data management system (MDMS) in some embodiments of the invention. The DDMS may be housed on a server or a plurality of servers which a user or a health care professional may access via a communications network via the Internet or the World Wide Web. This model of the DDMS, which is described as an MDMS is described in U.S. Pat. App. Pub. No. 2006/0031094, published Feb. 9, 2006, to Cohen et al., and is entitled, "Medical Data Management System and Process", which is herein incorporated by reference in its entirety.

While description of embodiments of the invention below are made in regard to monitoring medical or biological conditions for subjects having diabetes, the systems and processes below are applicable to monitoring medical or biological conditions for cardiac subjects, cancer subjects, HIV subjects, subjects with other disease, infection, or controllable conditions, or various combinations thereof.

In embodiments of the invention, the DDMS may be installed in a computing device in a health care provider's office, such as a doctor's office, a nurse's office, a clinic, an emergency room, an urgent care office. Health care providers may be reluctant to utilize a system where their confidential patient data is to be stored in a computing device such as a server on the Internet.

The DDMS may be installed on a computing device 100. The computing device 100 may be coupled to a display 33. In embodiments of the invention, the computing device 100 may be in a physical device separate from the display (such as in a personal computer, a mini-computer, etc.) In embodiments of the invention, the computing device 100 may be in a single physical enclosure or device with the display 33 such as a laptop where the display 33 is integrated into the computing device. In embodiments of the invention, the computing device 100 hosting the DDMS may be, but is not limited to, a desktop computer, a laptop computer, a server, a network computer, a personal digital assistant (PDA), a portable telephone including computer functions, a pager with a large visible display, an insulin pump including a display, a glucose sensor including a display, a glucose meter including a display, and/or a combination insulin pump/ glucose sensor having a display. The computing device may also be an insulin pump coupled to a display, a glucose meter coupled to a display, or a glucose sensor coupled to a display. The computing device 100 may also be a server located on the Internet that is accessible via a browser installed on a laptop computer, desktop computer, a network computer, or a PDA. The computing device 100 may also be a server located in a doctor's office that is accessible via a browser installed on a portable computing device, e.g., laptop, PDA, network computer, portable phone, which has wireless capabilities and can communicate via one of the wireless communication protocols such as Bluetooth and IEEE 802.11 protocols.

In the embodiment shown in FIG. 1, the data management system 16 comprises a group of interrelated software modules or layers that specialize in different tasks. The system software includes a device communication layer 24, a data parsing layer 26, a database layer 28, database storage devices 29, a reporting layer 30, a graph display layer 31, and a user interface layer 32. The diabetes data management system may communicate with a plurality of subject support devices 12, two of which are illustrated in FIG. 1. Although the different reference numerals refer to a number of layers, (e.g., a device communication layer, a data parsing layer, a database layer), each layer may include a single software module or a plurality of software modules. For example, the device communications layer 24 may include a number of interacting software modules, libraries, etc. In embodiments of the invention, the data management system 16 may be installed onto a non-volatile storage area (memory such as flash memory, hard disk, removable hard, DVD-RW, CD-RW) of the computing device 100. If the data management system 16 is selected or initiated, the system 16 may be loaded into a volatile storage (memory such as DRAM, SRAM, RAM, DDRAM) for execution.

The device communication layer 24 is responsible for interfacing with at least one, and, in further embodiments, to a plurality of different types of subject support devices 12, such as, for example, blood glucose meters, glucose sensors/ monitors, or an infusion pump. In one embodiment, the device communication layer 24 may be configured to communicate with a single type of subject support device 12. However, in more comprehensive embodiments, the device communication layer 24 is configured to communicate with multiple different types of subject support devices 12, such as devices made from multiple different manufacturers, multiple different models from a particular manufacturer and/or multiple different devices that provide different functions (such as infusion functions, sensing functions, metering functions, communication functions, user interface functions, or combinations thereof). As described in more detail below, by providing an ability to interface with multiple different types of subject support devices 12, the diabetes data management system 16 may collect data from a significantly greater number of discrete sources. Such embodiments may provide expanded and improved data analysis capabilities by including a greater number of subjects and groups of subjects in statistical or other forms of analysis that can benefit from larger amounts of sample data and/or greater diversity in sample data, and, thereby, improve capabilities of determining appropriate treatment parameters, diagnostics, or the like.

The device communication layer 24 allows the DDMS 16 to receive information from and transmit information to or from each subject support device 12 in the system 16. Depending upon the embodiment and context of use, the type of information that may be communicated between the system 16 and device 12 may include, but is not limited to, data, programs, updated software, education materials, warning messages, notifications, device settings, therapy parameters, or the like. The device communication layer 24 may include suitable routines for detecting the type of subject support device 12 in communication with the system 16 and implementing appropriate communication protocols for that type of device 12. Alternatively or in addition, the subject support device 12 may communicate information in packets or other data arrangements, where the communication includes a preamble or other portion that includes device identification information for identifying the type of the subject support device. Alternatively, or in addition, the subject support device 12 may include suitable user-operable interfaces for allowing a user to enter information, such as by selecting an optional icon or text or other device identifier, that corresponds to the type of subject support device used by that user. Such information may be communicated to the system 16, through a network connection. In yet further embodiments, the system 16 may detect the type of subject support device 12 it is communicating with in the manner described above and then may send a message requiring the user to verify that the system 16 properly detected the type of subject support device being used by the user. For systems 16 that are capable of communicating with multiple different types of subject support devices 12, the device communication layer 24 may be capable of implementing multiple different communication protocols and selects a protocol that is appropriate for the detected type of subject support device.

The data-parsing layer 26 is responsible for validating the integrity of device data received and for inputting it correctly into a database 29. A cyclic redundancy check CRC process for checking the integrity of the received data may be employed. Alternatively, or in addition, data may be received in packets or other data arrangements, where preambles or other portions of the data include device type identification information. Such preambles or other portions of the received data may further include device serial numbers or other identification information that may be used for validating the authenticity of the received information. In such embodiments, the system 16 may compare received identification information with pre-stored information to evaluate whether the received information is from a valid source.

The database layer 28 may include a centralized database repository that is responsible for warehousing and archiving stored data in an organized format for later access, and retrieval. The database layer 28 operates with one or more data storage device(s) 29 suitable for storing and providing access to data in the manner described herein. Such data storage device(s) 29 may comprise, for example, one or more hard discs, optical discs, tapes, digital libraries or other suitable digital or analog storage media and associated drive devices, drive arrays or the like.

Data may be stored and archived for various purposes, depending upon the embodiment and environment of use. As described below, information regarding specific subjects and patient support devices may be stored and archived and made available to those specific subjects, their authorized healthcare providers and/or authorized healthcare payor entities for analyzing the subject's condition. Also, certain information regarding groups of subjects or groups of subject support devices may be made available more generally for healthcare providers, subjects, personnel of the entity administering the system 16 or other entities, for analyzing group data or other forms of conglomerate data.

Embodiments of the database layer 28 and other components of the system 16 may employ suitable data security measures for securing personal medical information of subjects, while also allowing non-personal medical information to be more generally available for analysis. Embodiments may be configured for compliance with suitable government regulations, industry standards, policies or the like, including, but not limited to the Health Insurance Portability and Accountability Act of 1996 (HIPAA).

The database layer 28 may be configured to limit access of each user to types of information pre-authorized for that user. For example, a subject may be allowed access to his or her individual medical information (with individual identifiers) stored by the database layer 28, but not allowed access to other subject's individual medical information (with individual identifiers). Similarly, a subject's authorized healthcare provider or payor entity may be provided access to some or all of the subject's individual medical information (with individual identifiers) stored by the database layer 28, but not allowed access to another individual's personal information. Also, an operator or administrator-user (on a separate computer communicating with the computing device 100) may be provided access to some or all subject information, depending upon the role of the operator or administrator. On the other hand, a subject, healthcare provider, operator, administrator or other entity, may be authorized to access general information of unidentified individuals, groups or conglomerates (without individual identifiers) stored by the database layer 28 in the data storage devices 29.

In embodiments of the invention, the database layer 28 may store preference profiles. In the database layer 28, for example, each user may store information regarding specific parameters that correspond to the user. Illustratively, these parameters could include target blood glucose or sensor glucose levels, what type of equipment the users utilize (insulin pump, glucose sensor, blood glucose meter, etc.) and could be stored in a record, a file, or a memory location in the data storage device(s) 29 in the database layer. Illustratively, these parameters could also include analysis times for each of the meal events.

The DDMS 16 may measure, analyze, and track either blood glucose (BG) or sensor glucose (SG) readings for a user. In embodiments of the invention, the medical data management system may measure, track, or analyze both BG and SG readings for the user. Accordingly, although certain reports may mention or illustrate BG or SG only, the reports may monitor and display results for the other one of the glucose readings or for both of the glucose readings.

The reporting layer 30 may include a report wizard program that pulls data from selected locations in the database 28 and generates report information from the desired parameters of interest. The reporting layer 30 may be configured to generate multiple different types of reports, each having different information and/or showing information in different formats (arrangements or styles), where the type of report may be selectable by the user. A plurality of pre-set types of report (with pre-defined types of content and format) may be available and selectable by a user. At least some of the pre-set types of reports may be common, industry standard report types with which many healthcare providers should be familiar.

In embodiments of the invention, the database layer 28 may calculate values for various medical information that is to be displayed on the reports generated by the report or reporting layer 30. For example, the database layer 28, may calculate average blood glucose or sensor glucose readings for specified timeframes. In embodiments of the invention, the reporting layer 30 may calculate values for medical or physical information that is to be displayed on the reports. For example, a user may select parameters which are then utilized by the reporting layer 30 to generate medical information values corresponding to the selected parameters. In other embodiments of the invention, the user may select a parameter profile that previously existed in the database layer 28.

Alternatively, or in addition, the report wizard may allow a user to design a custom type of report. For example, the report wizard may allow a user to define and input parameters (such as parameters specifying the type of content data, the time period of such data, the format of the report, or the like) and may select data from the database and arrange the data in a printable or displayable arrangement, based on the user-defined parameters. In further embodiments, the report wizard may interface with or provide data for use by other programs that may be available to users, such as common report generating, formatting or statistical analysis programs such as, but not limited to, EXCEL™ or the like. In this manner, users may import data from the system 16 into further reporting tools familiar to the user. The reporting layer 30 may generate reports in displayable form to allow a user to view reports on a standard display device, printable form to allow a user to print reports on standard printers, or other suitable forms for access by a user. Embodiments may operate with conventional file format schemes for simplifying storing, printing and transmitting functions, including, but not limited to PDF, JPEG, or the like. Illustratively, a user may select a type of report and parameters for the report and the reporting layer 30 may create the report in a PDF format. A PDF plug-in may be initiated to help create the report and also to allow the user to view the report. Under these operating conditions, the user may print the report utilizing the PDF plug-in. In certain embodiments in which security measures are implemented, for example, to meet government regulations, industry standards or policies that restrict communication of subject's personal information, some or all reports may be generated in a form (or with suitable software controls) to inhibit printing, or electronic transfer (such as a non-printable and/or non-capable format). In yet further embodiments, the system 16 may allow a user generating a report to designate the report as non-printable and/or non-transferable, whereby the system 16 will provide the report in a form that inhibits printing and/or electronic transfer.

The reporting layer 30 may transfer selected reports to the graph display layer 31. The graph display layer 31 receives information regarding the selected reports and converts the data into a format that can be displayed or shown on a display 33.

In embodiments of the invention, the reporting layer 30 may store a number of the user's parameters. Illustratively, the reporting layer 30 may store the type of carbohydrate units, a blood glucose movement or sensor glucose reading, a carbohydrate conversion factor, and timeframes for specific types of reports. These examples are meant to be illustrative and not limiting.

Data analysis and presentations of the reported information may be employed to develop and support diagnostic and therapeutic parameters. Where information on the report relates to an individual subject, the diagnostic and therapeutic parameters may be used to assess the health status and relative well-being of that subject, assess the subject's compliance to a therapy, as well as to develop or modify treatment for the subject and assess the subject's behaviors that affect his/her therapy. Where information on the report relates to groups of subjects or conglomerates of data, the diagnostic and therapeutic parameters may be used to assess the health status and relative well-being of groups of subjects with similar medical conditions, such as, but not limited to, diabetic subjects, cardiac subjects, diabetic subjects having a particular type of diabetes or cardiac condition, subjects of a particular age, sex or other demographic group, subjects with conditions that influence therapeutic decisions such as but not limited to pregnancy, obesity, hypoglycemic unawareness, learning disorders, limited ability to care for self, various levels of insulin resistance, combinations thereof, or the like.

The user interface layer 32 supports interactions with the end user, for example, for user login and data access, software navigation, data input, user selection of desired report types and the display of selected information. Users may also input parameters to be utilized in the selected reports via the user interface layer 32. Examples of users include but are not limited to: healthcare providers, healthcare payer entities, system operators or administrators, researchers, business entities, healthcare institutions and organizations, or the like, depending upon the service being provided by the system and depending upon the invention embodiment. More comprehensive embodiments are capable of interacting with some or all of the above-noted types of users, wherein different types of users have access to different services or data or different levels of services or data.

In an example embodiment, the user interface layer 32 provides one or more websites accessible by users on the Internet. The user interface layer may include or operate with at least one (or multiple) suitable network server(s) to provide the website(s) over the Internet and to allow access, world-wide, from Internet-connected computers using standard Internet browser software. The website(s) may be accessed by various types of users, including but not limited to subjects, healthcare providers, researchers, business entities, healthcare institutions and organizations, payor entities, pharmaceutical partners or other sources of pharmaceuticals or medical equipment, and/or support personnel or other personnel running the system 16, depending upon the embodiment of use.

In another example embodiment, where the DDMS 16 is located on one computing device 100, the user interface layer 32 provides a number of menus to the user to navigate through the DDMS. These menus may be created utilizing any menu format, including but not limited to HTML, XML, or Active Server pages. A user may access the DDMS 16 to perform one or more of a variety of tasks, such as accessing general information made available on a website to all subjects or groups of subjects. The user interface layer 32 of the DDMS 16 may allow a user to access specific information or to generate reports regarding that subject's medical condition or that subject's medical device(s) 12, to transfer data or other information from that subject's support device(s) 12 to the system 16, to transfer data, programs, program updates or other information from the system 16 to the subject's support device(s) 12, to manually enter information into the system 16, to engage in a remote consultation exchange with a healthcare provider, or to modify the custom settings in a subject's supported device and/or in a subject's DDMS/MDMS data file.

The system 16 may provide access to different optional resources or activities (including accessing different information items and services) to different users and to different types or groups of users, such that each user may have a customized experience and/or each type or group of user (e.g., all users, diabetic users, cardio users, healthcare provider-user or payor-user, or the like) may have a different set of information items or services available on the system. The system 16 may include or employ one or more suitable resource provisioning program or system for allocating appropriate resources to each user or type of user, based on a pre-defined authorization plan. Resource provisioning systems are well known in connection with provisioning of electronic office resources (email, software programs under license, sensitive data, etc.) in an office environment, for example, in a local area network LAN for an office, company or firm. In one example embodiment, such resource provisioning systems is adapted to control access to medical information and services on the DDMS 16, based on the type of user and/or the identity of the user.

Upon entering successful verification of the user's identification information and password, the user may be provided access to secure, personalized information stored on the DDMS 16. For example, the user may be provided access to a secure, personalized location in the DDMS 16 which has been assigned to the subject. This personalized location may be referred to as a personalized screen, a home screen, a home menu, a personalized page, etc. The personalized location may provide a personalized home screen to the subject, including selectable icons or menu items for selecting optional activities, including, for example, an option to transfer device data from a subject's supported device 12 to the system 16, manually enter additional data into the system 16, modify the subject's custom settings, and/or view and print reports. Reports may include data specific to the subject's condition, including but not limited to, data obtained from the subject's subject support device(s) 12, data manually entered, data from medical libraries or other networked therapy management systems, data from the subjects or groups of subjects, or the like. Where the reports include subject-specific information and subject identification information, the reports may be generated from some or all subject data stored in a secure storage area (e.g., storage devices 29) employed by the database layer 28.

The user may select an option to transfer (send) device data to the medical data management system 16. If the system 16 receives a user's request to transfer device data to the system, the system 16 may provide the user with step-by-step instructions on how to transfer data from the subject's supported device(s) 12. For example, the DDMS 16 may have a plurality of different stored instruction sets for instructing users how to download data from different types of subject support devices, where each instruction set relates to a particular type of subject supported device (e.g., pump, sensor, meter, or the like), a particular manufacturer's version of a type of subject support device, or the like. Registration information received from the user during registration may include information regarding the type of subject support device(s) 12 used by the subject. The system 16 employs that information to select the stored instruction set(s) associated with the particular subject's support device(s) 12 for display to the user.

Other activities or resources available to the user on the system 16 may include an option for manually entering information to the DDMS/MDMS 16. For example, from the user's personalized menu or location, the user may select an option to manually enter additional information into the system 16.

Further optional activities or resources may be available to the user on the DDMS 16. For example, from the user's personalized menu, the user may select an option to receive data, software, software updates, treatment recommendations or other information from the system 16 on the subject's support device(s) 12. If the system 16 receives a request from a user to receive data, software, software updates, treatment recommendations or other information, the system 16 may provide the user with a list or other arrangement of multiple selectable icons or other indicia representing available data, software, software updates or other information available to the user.

Yet further optional activities or resources may be available to the user on the medical data management system 16 including, for example, an option for the user to customize or otherwise further personalize the user's personalized location or menu. In particular, from the user's personalized location, the user may select an option to customize parameters for the user. In addition, the user may create profiles of customizable parameters. When the system 16 receives such a request from a user, the system 16 may provide the user with a list or other arrangement of multiple selectable icons or other indicia representing parameters that may be modified to accommodate the user's preferences. When a user selects one or more of the icons or other indicia, the system 16 may receive the user's request and makes the requested modification.

Further descriptions of the DDMS/MDMS may be found in U.S. Pat. App. Pub. No. 2007/0033074, published Feb. 8, 2007, to Nitzan et al. and is entitled, "Therapy Management System", which is herein incorporated by reference in its entirety.

Figure 2A:
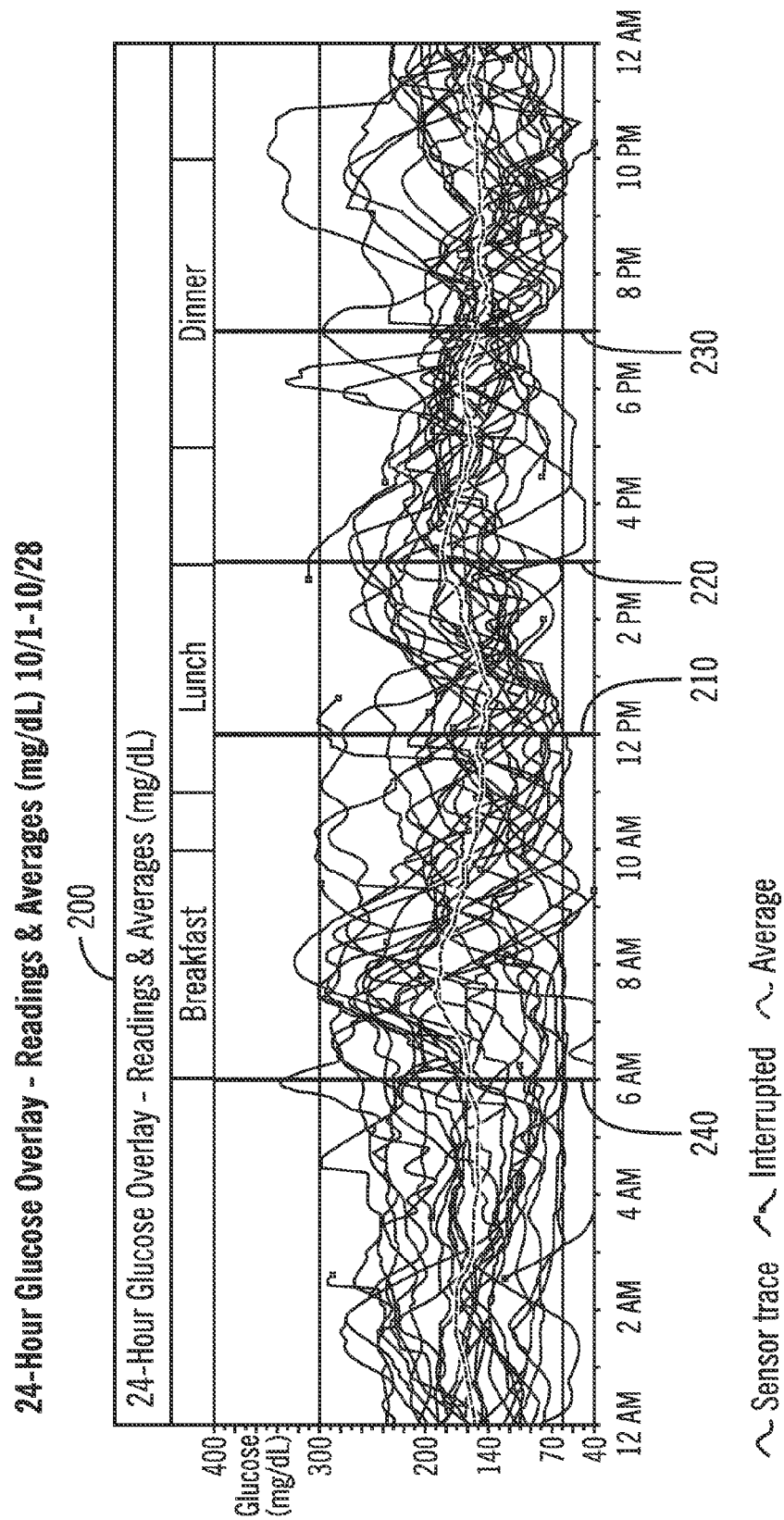
FIG. 2A illustrates a sample report displaying sensor readings according to embodiments of the present invention.

FIG. 2A illustrates a report displaying sensor readings according to embodiments of the present invention. The report illustrated in FIG. 2A is a 24-Hour Glucose Overlay report 200, which may be generated by, for example, the DDMS/MDMS 16 of FIG. 1, or any other suitable system. One particular example of a suitable system is a computer executing Medtronic MiniMed's CARELINK™ Therapy Management Software, available at carelink.minimed.com. The sample overlay report 200 illustrates the overlaying of readings and averages of glucose values from a user for a 28-day period. In alternative embodiments, longer or shorter periods may be used, such as, but not limited to three days, one week, two weeks, three weeks, one month, two months, one quarter, six months, one year, or the life of a patient, with the choice being made to select a data set that provides a useful period of interest. The report 200 may also show the readings and averages for less than 24-hours at a time, too.

Because many people have regular schedules where event occurrences such as breakfast, lunch, dinner, afternoon naps, tea times, coffee breaks, watching the morning or evening TV news, going to bed for the night (bedtime), etc., occur each day and generally occur around the same time of day (or each day during the work week, work days only, weekends only, Sundays only, workout days only, etc.), patterns may develop based on this regular schedule. Additionally, patterns also may be analyzed based on only periodic events/conditions such as but not limited to, menstruation, non-work/school days, when administering periodic therapy, exercise, and the like; and transient events/conditions such as but not limited to, a temporary illness, having a cold, being on a particular medication, stress and anxiety, physical exertion, vacation days, holidays, etc.

By analyzing the average glucose level patterns, trends may be spotted that occur for a user relative to specific events in that user's life (e.g., breakfast, lunch, dinner, watching the evening news, etc.). For example, referring to the report 200 of FIG. 2A, we note that for this representative 28-day period, when the user has lunch at Noon shown at line 210, this user tends to experience on average a rise in glucose levels peaking around 3 PM shown at line 220, three hours after the start of lunch. Although average glucose level values are used in connection with FIG. 2A, according to embodiments of the present invention, other calculations and data sets such as standard deviations, high values, low values, etc. for a period (days, weeks, months, quarters, years, etc.), or periodic blocks of time (e.g., every fourth week, four weeks of work days, five weekends, non-working days, etc.) may be utilized as well. It is noted that glucose patterns often change during menstruation, and patterns for work days tend to be different from patterns on non-working days.

Based on this average pattern and trend, this information may be passed along to a doctor or a user, and/or to a DDMS/MDMS, an infusion pump, a controller/programmer, or any other suitable device, for example, which may take proactive measures in recommending and/or automatically delivering a bolus of insulin in advance of this predicted rise and peak shown at line 220 (e.g., a notification event that the user should be made aware of, and/or to take appropriate action) if a rise in glucose levels begins to occur, e.g., an hour after lunch. If the user normally takes lunch at Noon but one day is caught in a meeting that runs longer, and the user takes lunch at 1 PM instead, the infusion pump (or any other suitable device), for example, may make a prediction as to the upcoming rise and peak shown at line 220 based on the average glucose level pattern derived from the report 200 of FIG. 2A and time-shift the pattern one-hour later, such that it will predict a rise and peak at 4 PM instead of 3 PM, and take proactive measures in recommending and/or delivering a bolus in advance of this predicted rise and peak if it starts to notice a rise in glucose levels an hour after taking lunch at 1 PM. Alternatively, the basal rate of insulin delivery may be temporarily increased to match this rise and peak following lunch taken at 1 PM, an hour later than usual (e.g., a "lunch time" basal rate pattern, a "dinner time" basal rate pattern, etc.). Further description of an insulin infusion device having the capability to deliver time-shifted basal insulin may be found in U.S. Pat. App. Pub. No. 2007/0112298, published May 17, 2007, to Mueller et al. and entitled "External Infusion Device with Programmable Capabilities to Time-Shift Basal Insulin and Method of Using the Same", which is herein incorporated by reference in its entirety.

By predicting the occurrence of a notification event (e.g., a rise and/or peak), more accurate treatment and delivery of insulin may be accomplished to better keep a user within a preferred glucose level range, but additionally, occurrences of severe adverse events (SAEs) may be minimized. Typically, a particular pattern occurs just before an SAE occurs, and if the DDMS/MDMS, infusion pump, or other suitable device, recognizes the pre-SAE pattern developing, the user may be alerted of a potential SAE occurring and preventive measures may be taken to minimize or eliminate the occurrence of the SAE, even automatically without user input, if necessary according to embodiments of the present invention.

Although an average glucose level pattern for a 24-hour period may be used, the 24-hour pattern may be partitioned into multiple patterns anchored around triggering events (event occurrences) as reference points, e.g., a pattern for breakfast to lunch (morning pattern), a pattern from lunch to dinner (afternoon pattern), and a pattern from dinner to breakfast (evening pattern), for time shifting. Meal times and meal boluses (including correction boluses) serve as good triggering events, but any other suitable event occurrence (especially those events that occur regularly in a user's life around the same time each day) may be utilized as well for the purposes of establishing common points of reference for the time-shifting of a pattern. Alarms, for example, are often followed by a bolus event, and high glucose level alarms may serve as a triggering event occurrence, too. According to embodiments of the present invention, the patterns also may be sorted by weekdays only, weekends only, a particular day only (e.g., Wednesdays only), sick days only, exercise/workout days only, etc.

According to embodiments of the present invention, the user may inform the DDMS/MDMS, infusion pump, controller/programmer, or any other suitable device, that he/she is about to have lunch, and the infusion pump, for example, may acknowledge and record the occurrence of this triggering event to perform any time-shifting of a pattern as necessary. Alternatively, the DDMS/MDMS, infusion pump, controller/programmer, or any other suitable device may deduce when a meal is about to be taken based on a user initiated bolus delivery and the time it occurred (e.g., around 7 AM for breakfast, or around Noon for lunch, etc.). Knowing how much insulin was delivered for a meal may be as relevant as knowing the type of meal, for example, breakfast, lunch, or dinner, consumed. Moreover, the type of bolus selected and administered by the user (e.g., a normal, square wave, dual wave, a correction bolus, etc.) along with the type of food ingested at that time may also permit the DDMS/MDMS, infusion pump, controller/programmer, or any other suitable device to deduce that the user may have certain issues with particular foods (e.g., fatty foods).

By identifying and performing time-shifting of patterns, we may make better predictions as to the glucose levels of a diabetic and allow a doctor to take proactive measures to provide more accurate treatment to keep more stable glucose levels within the desired range. Severe adverse events (SAEs) may be minimized or eliminated by recognizing the pre-SAE pattern leading up to SAEs in the past. The use of A1c testing may further assist in determining whether glucose levels have been within desirable ranges for a longer period of time (e.g., about three months). According to embodiments of the present invention, alarms may be set up on an infusion pump to match a typical user SAE pattern, and the alarm may sound when such a SAE pattern is observed.

To make a pattern more accurate, anomalous data may be removed or filtered from the data points making up the pattern ("clipping"), as the anomalous data may not be representative of a person's typical day. For example, referring to the report 200 of FIG. 2A, if the user had a few days where his/her schedule was completely atypical of a regular work day (perhaps flying cross-country on a business trip), we may exclude the glucose level readings for these non-routine days as they are not typical of a "regular" work day (it is likely that the user had a meal or two during the business trip, but, these meals may not have occurred at the same usual times the user typically has these meals, and/or the meals may be of different types, portions, etc. that the user typically has). That is, rare events and anomalous data generally should not dictate the direction of therapy based on patterns. According to embodiments of the present invention, the data also may be filtered by a particular day of the week (e.g., remove all Wednesday data), a day each month (e.g., remove all data on the 15th), a type of day (e.g., remove all data on exercise/workout days), by particular time of day (e.g., remove all data from 12 AM to 3 AM), by a particular week, month, etc., or any combination thereof.

Conversely, there are situations where investigating outlying/anomalous events may assist in determining behavioral issues that may have an impact on the course of therapy, and determining causes of an outlying event may be helpful in reducing these anomalous occurrences that may be detrimental to therapy. According to embodiments of the present invention, the data set may also be filtered such that all glucose level readings falling into one or more patterns is removed, leaving only the anomalous data for analysis.

The reports/charts illustrated in FIGS. 2B-2K may be representative of snapshot screens displayed on a DDMS/MDMS executing, for example, Medtronic MiniMed's CARELINK™ Therapy Management Software, or any other suitable software, as described in connection with FIG. 1 above, to assist a doctor in planning a course of treatment (and in some instances, accessible to a user, too). Although the charts illustrated in FIGS. 2B-2I and 2K show the glucose readings from 11 AM to 9 PM, longer or shorter periods may be displayed according to embodiments of the present invention. The charts in FIGS. 2B-2I and 2K, as illustrated, may be portions of the 24-hour report illustrated in FIG. 2A. For instance, in other embodiments, a 1-hour, 2-hour, 3-hour, 4-hour, 5-hour, 6-hour, 7-hour, 8-hour, 9-hour, 10-hour, 11-hour, or 12-hour portions of a 24-hour day report may be used, and 2 days, 3 days, 4 days, 5 days, 6 days, a week, 2 weeks, 3 weeks, 4 weeks, a month, a quarter, or the like reports may be used as well.

Although only four representative glucose reading lines are illustrated in each of FIGS. 2B-2J, an actual chart viewed by a doctor often displays many more lines (20 to 30, or more), and while only four lines are represented in FIGS. 2B-2J to simplify and make the charts easier to read for illustrative purposes, according to embodiments of the present invention, any number of lines may be overlaid on the charts. Lines 252, 254, 256, and 258 in FIG. 2B (and similarly for the corresponding lines in FIGS. 2C-2J) may each represent raw glucose level readings for a day, filtered, smoothed, etc. readings for a day, several days, weeks, months, etc., or any combination thereof. A chart including the average value of the raw glucose level readings, standard deviation (once the average has been determined), high-low lines, etc., for example, as illustrated in FIG. 2K and discussed in further detail below, also may be generated.

According to embodiments of the present invention, additional data may be further shown in the charts of FIGS. 2B-2K as well, for example, a basal insulin profile and a bolus delivery graph. Moreover, a doctor or user may select any one of the readings (e.g., lines 252, 254, 256, 258 in FIG. 2B) displayed on the charts by the DDMS/MDMS to obtain further data associated with the selected reading (e.g., high/low values, averages, standard deviation, number of meter reads, total insulin, number of boluses, prime volume, time in temporary basal, time in suspension, etc.), which may be displayed on a separate screen. Further description of data that may be displayed on a screen by the DDMS/MDMS may be found in U.S. Pat. App. Pub. No. 2002/0193679, published Dec. 19, 2002, to Malave et al. and entitled "Communication Station and Software for Interfacing with an Infusion Pump, Analyte Monitor, Analyte Meter, or the Like", which is herein incorporated by reference in its entirety.

Generally speaking, the more data that is available to a doctor, the more accurate and better the treatment may be planned for a user. However, the more data that is displayed on a screen at once (e.g., daily 24-hour glucose sensor readings for a three-month period will have over 90 lines moving up and down the chart), the more difficult it is for a doctor or other viewer to read and comprehend, especially if the data does not readily appear to convey any trends or patterns on which a doctor may base a course of treatment.

Having more data available also increases the chances that more "noise" data will be introduced into the overall data set. In particular, a doctor using a DDMS/MDMS displaying a glucose readings overlay report (e.g., as in FIG. 2A) may have data spanning a period of days, weeks, months, and/or years for a single patient. This amount of data displayed on a screen all at once is overwhelming, confusing, and difficult to read and understand without some filtering and organization. This raw data becomes not particularly useful on its face without further analysis. No meaningful treatment plan may be formulated based on a chart of numerous glucose readings, such as shown in FIG. 2A, that seemingly has no relation to each other. If the numerous glucose level readings displayed may be sorted, for example, by similar like patterns, and/or around particular event occurrences (e.g., breakfast, lunch, or dinner), the doctor will have a more meaningful chart where certain glucose level patterns may be perceived on which he/she may develop a course of treatment.

As discussed above, many people have regular schedules where event occurrences such as breakfast, lunch, dinner, afternoon naps, tea times, coffee breaks, watching the morning or evening TV news, going to sleeping/bedtime, waking up, etc., that tend to occur each day and generally around the same time of day (or each day during the work week, work days only, weekends only, Sundays only, workout days only, etc.). Knowing when these events occur is particularly helpful in analyzing the raw data. Using these events (e.g., breakfast, lunch, dinner, watching the evening news, etc.) as markers and reference/anchoring points in time (e.g., starting points, mid-points, end points) to adjust or filter the glucose level readings amongst all of the readings relative to each common event occurrence will allow an analysis where trends and patterns may be perceived. In one representative example according to embodiments of the present invention, the glucose level readings may be lined up starting from when the user initiates a lunch time meal bolus, a correction bolus, a particular bolus type (e.g., normal, square wave, dual wave), etc., and the DDMS/MDMS may analyze the glucose level readings from the start of the meal bolus (e.g., up to the start of the next common event occurrence of, e.g., a dinner time meal bolus) to determine whether patterns exist, take an average reading, etc. The glucose level readings also may be lined up based on any suitable event occurrence, including but not limited to meal boluses, correction boluses, meal times, bedtimes, exercise, intake of medications, etc. The readings may be shifted and lined up on an existing time scale, for example, as illustrated in FIG. 2C, or according to embodiments of the present invention, using a relative time scale zeroed to the start of a particular event occurrence, for example, as illustrated in FIG. 2J and discussed in further detail below.

The DDMS/MDMS may generate a variety of patterns from the glucose level readings anchored around particular event occurrence(s). Glucose level readings that seem to fall outside of any particular pattern (e.g., anomalous readings) may be further analyzed, or filtered out and discarded. Alternatively, only the anomalous readings may be shown. Suitable pattern recognition algorithms (e.g., utilized in defense/weapon systems, astronomy, computer science, etc.) may be modified to be used to analyze the plurality of glucose level readings for a user, and according to embodiments of the present invention, to analyze the readings after each common event occurrence amongst all or most of the readings to determine whether any patterns or trends exist.

The pattern recognition algorithm may recognize a seemingly "anomalous" glucose level reading that fits a particular pattern or shape formed by a plurality of other glucose level readings around a particular event occurrence (e.g., a pattern formed by the readings starting when the user takes lunch each day). This anomalous reading may appear to be, for example: (1) skewed a couple hours ahead of or behind the particular pattern, (2) having a greater positive and/or negative magnitude than the particular pattern, (3) compressed or stretched in time than the particular pattern, (4) skewed upwards or downwards from the basal glucose level of the particular pattern, or any combination thereof. By recognizing a potential glucose level reading falling "out-of-pattern" from a particular pattern formed by the other glucose level readings, this out-of-pattern reading may be adapted to fit with the rest of the glucose level readings forming the pattern by making adjustments to the out-of-pattern glucose level reading, thus preserving that glucose level reading for analysis.

Alternatively, the out-of-pattern glucose level reading may be analyzed on its own merits to determine potential causes of such an out-of-pattern reading and any other potential issues associated therewith, which may be helpful in learning the behavior of a user and in making any adjustments to his/her therapy as necessary to minimize further out-of-pattern readings. Moreover, the patterns may be in themselves further sorted and filtered by the types of readings forming the patterns, for example, a "weekday only" pattern (formed from weekday only readings), a "weekend only" pattern (formed from weekend only readings), "Wednesdays" pattern (formed from Wednesdays only readings), etc.

Although the existence of an event occurrence as a marker for a glucose level reading is helpful in establishing a reference point for the pattern recognition software to analyze for patterns, an event occurrence is not always necessary for the pattern recognition software and may not always be available for each glucose level reading. It is possible that a meal/correction bolus event occurrence was not recorded by, for example, the infusion device or controller/programmer, because the user self-administered a bolus with a manual shot via a needle and syringe. Secondly, the user may have forgotten to enter an exercise event occurrence marker when the user exercised. Thirdly, the user may have just missed administering a bolus, leaving no event occurrence marker of one, or the bolus may have been administered but was not recorded. The administered bolus may have been the wrong type, too much, too little, etc., such that it makes the event occurrence marker corresponding to that administered bolus unhelpful for purposes of analysis.

Even absent an event occurrence marker in the glucose level readings, the pattern recognition software may still analyze a glucose level reading, for example, by determining whether there is a match in the rising/falling slope of the reading, in the overall shape of the reading, the overall size/magnitude of the reading, etc., with other glucose level readings, with or without event occurrence markers, forming a particular pattern.

Figure 2B:
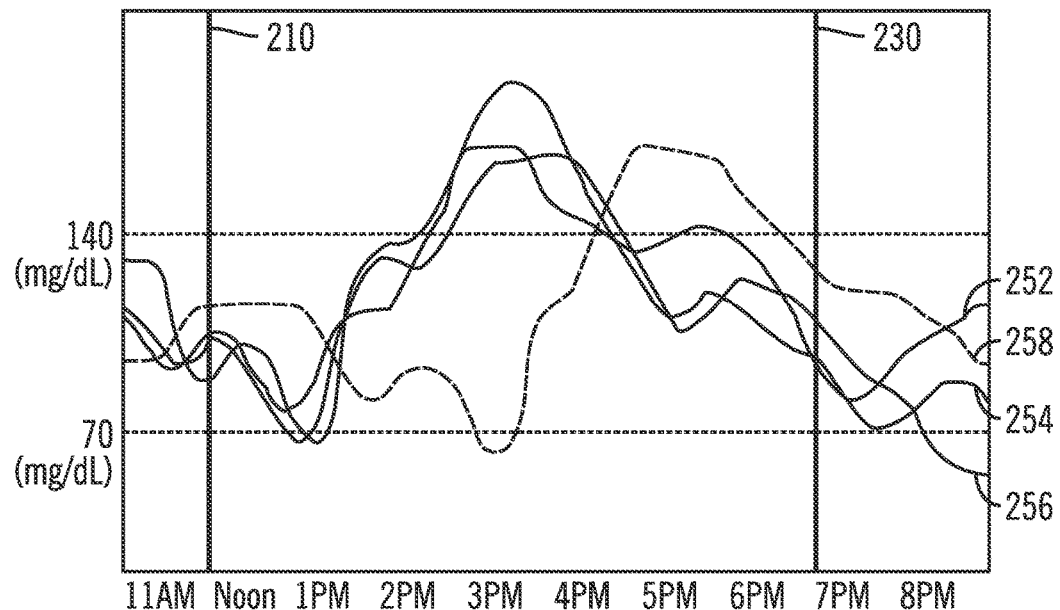
FIG. 2B illustrates a sample report displaying sensor readings according to embodiments of the present invention.
Figure 2C:
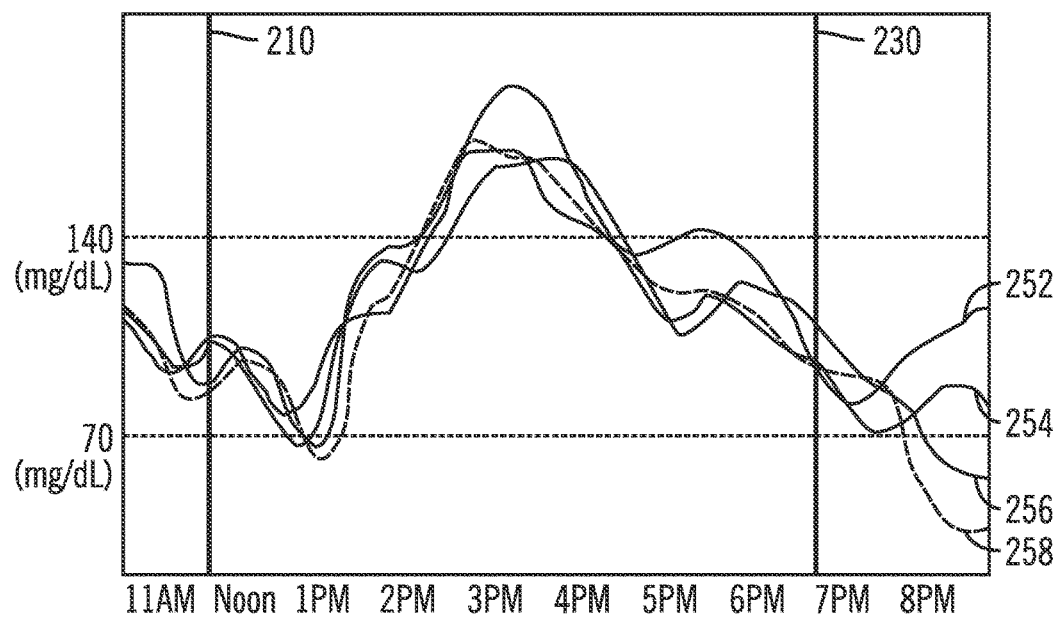
FIG. 2C illustrates an adapted time-shifted sample report displaying sensor readings from FIG. 2B according to embodiments of the present invention.

As illustrated in the simplified representative glucose overlay chart of FIG. 2B, four representative glucose level reading lines 252, 254, 256, 258 are shown. By analyzing the data in the chart of FIG. 2B, the DDMS/MDMS may determine that a pattern of two small successive dips followed by a large rise in glucose levels exist for lines 252, 254, 256, and 258. This particular pattern of dips and rises is merely an illustrative example, and according to embodiments of the present invention, any other patterns and types of patterns may be analyzed. Line 258 appears to be an anomaly such that its two small successive dips followed by a rise occur a couple hours later than at lines 252, 254, 256, but otherwise follows a similar shape as the pattern formed by lines 252, 254, 256.

To use as much of the available data as possible, the DDMS/MDMS may try to adapt or "fit" the anomalous data to an existing pattern(s). By recognizing the general pattern formed by lines 252, 254, 256 and that of anomalous line 258, the DDMS/MDMS may determine that by shifting the anomalous line 258 back two hours in time (to match the data obtained when the user typically takes lunch), as illustrated in FIG. 2C, the reading of line 258 generally conforms with the pattern established by lines 252, 254, 256, especially from the period of Noon to 7 PM. The time-shifting may be performed, for example, if we knew that the user took lunch two hours later at 2 PM than his/her usual time at Noon when the reading for line 258 was taken (discussed in further detail below). By time-shifting line 258, an additional set of data may be utilized for analysis. The doctor may see that the user tends to rise and peak around 3 PM, and a course of treatment may be tailored towards this trend and attempt to reduce this spike and keep the glucose levels more stable and within the desired range.

The DDMS/MDMS may automatically attempt to conform data sets (e.g., each glucose level reading) to an entire 24-hour period, or any portion thereof, e.g., to generate a "morning" pattern, "afternoon" pattern, "evening" pattern, or the like. The patterns are more robust if more data is available, and by conforming anomalous data to existing data sets for a pattern, the therapy may be more accurate. In a perfect situation (but not likely), every glucose level reading falls into at least one pattern, with or without adjustment of the glucose level readings by the DDMS/MDMS. Having a chart of organized patterns for all or most of the data greatly assists the doctor in observing trends and preparing the best course of treatment for the user. However, if anomalous data cannot be properly conformed, that is, it does not appear to fit any of the patterns, the anomalous data may be filtered out and not utilized in the analysis. For example, the adapted time-shifted pattern in the chart of FIG. 2C may be utilized to generate an average "afternoon" pattern for analysis by a doctor to help the user in keeping stable glucose levels and within the desired range. Additionally, general trends or ideal patterns may be overlaid onto an existing report to show how close the user is to such ideal or population average levels, and to highlight areas where the user may want to make changes affecting his/her glucose levels.

Moreover, according to embodiments of the present invention, a doctor or user may select the criteria and parameters to filter and analyze the glucose level readings. A doctor or user may also select whether a particular pattern should be included or excluded from analysis. According to embodiments of the present invention and as discussed above, a doctor or user may click on any one of the glucose level readings (e.g., lines 252, 254, 256, 258 in FIG. 2B) and obtain further data relating to this selected reading, and enter notes or comments regarding this selected reading that may be stored by the DDMS/MDMS (e.g., indicating an unmarked event, explanation of a particular behavior, etc.). Alternatively, a doctor or user may select/click one or more of the displayed lines and delete them for the purposes of not including the selected lines in the analysis (e.g., to generate the average, standard deviations, etc.). For example, the clinician may realize that some days have very unusual data due to unusual circumstances in the patient's life, such as, e.g., stress due to a car accident, an emotional event, unusual physical exertion, unusual meals due to a celebration or travel, and the like. By eliminating these unusual data sets, the usual data sets remain, which the clinician may use to analyze and plan a course of therapy.

The glucose level analysis may be further enhanced if we know, by direct user input (e.g., setting a "lunch" event occurrence marker) or inferred from a user action (e.g., administering a meal bolus in the afternoon to have lunch), that the user took lunch at Noon on the days (weeks, months, etc.) that lines 252, 254, 256 were read; and that for line 258, the user took lunch a couple hours later around 2 PM versus at Noon. Additionally, the DDMS/MDMS may recognize that line 258 follows a particular pattern and/or shape that falls within a "lunch time" pattern, and a start time of when the user took lunch for that particular line 258 may also be inferred and calculated based on pattern recognition algorithms according to embodiments of the present invention. This type of information would further strengthen the pattern recognition and filtering scheme performed by the DDMS/MDMS in generating an "afternoon" pattern anchored around when the user takes lunch. For example, an understanding or analysis may be developed to reduce the rise and peak that occurs about two hours after the user eats in the afternoon, whether it is always at Noon, or at another time, for example, by setting a temporary basal rate to be utilized when taking lunch to reduce the observed rise and peak.

FIG. 2J illustrates an adapted time-shifted sample report displaying sensor readings from FIG. 2C utilizing a relative time line according to embodiments of the present invention. A relative time line chart, fixed at, for example, an event occurrence such as a meal bolus, start of lunch (line 210), etc., may be generated by the DDMS/MDMS for analysis by a doctor. A notification event occurring after a time span from an event occurrence, and anomalies, are more readily discernible using a relative time line chart as in FIG. 2J. Any time increments other than one hour (e.g., 2-hours, minute(s), day(s), week(s), month(s), quarter(s), year(s), etc.) and for any period in time may be utilized, too. According to embodiments of the present invention, the relative time line chart of FIG. 2J may be equally applicable to any of the charts illustrated in FIGS. 2A-2I and 2K.

FIG. 2K illustrates a report showing an average glucose level reading, standard deviation, and high-low lines for the adapted time-shifted report of FIG. 2C according to embodiments of the present invention. The DDMS/MDMS may generate a chart displaying an average glucose reading 292 based on the adapted glucose level readings 252, 254, 256, 258 of FIG. 2C. Once an average is determined, the DDMS/MDMS may also present the standard deviation lines 294, 296 as illustrated in FIG. 2K according to embodiments of the present invention. Furthermore, high-low lines 298 of the adapted glucose level readings of lines 252, 254, 256, 258 of FIG. 2C also may be generated. Any other types of data calculations other than those discussed above also may be performed by the DDMS/MDMS and displayed for review by a doctor or user. According to embodiments of the present invention, the display of average glucose level readings, standard deviation, and high-low lines, as in the chart of FIG. 2K, independently, combined, or with other data calculations may be equally applicable to any of the charts illustrated in FIGS. 2A-2J. For example, an average of a group of lines may be calculated, and then the error for each line compared to the average may be calculated. One method of calculation involves calculating the average line using all but one of the lines, and then calculate the error between the average and the line that was ignored; this process is repeated for all the groups of lines, and then the lines with the greatest errors may be determined. If a particular line or group of lines have significantly greater errors compared to the average, then the average may be recalculated by omitting these lines that have greater errors compared to the average. These lines having greater errors may be automatically removed from analysis, or they may be highlighted such that a clinician may elect to keep or remove them from analysis. Analysis on only the lines having greater errors may be also performed, too.

Figure 2D:
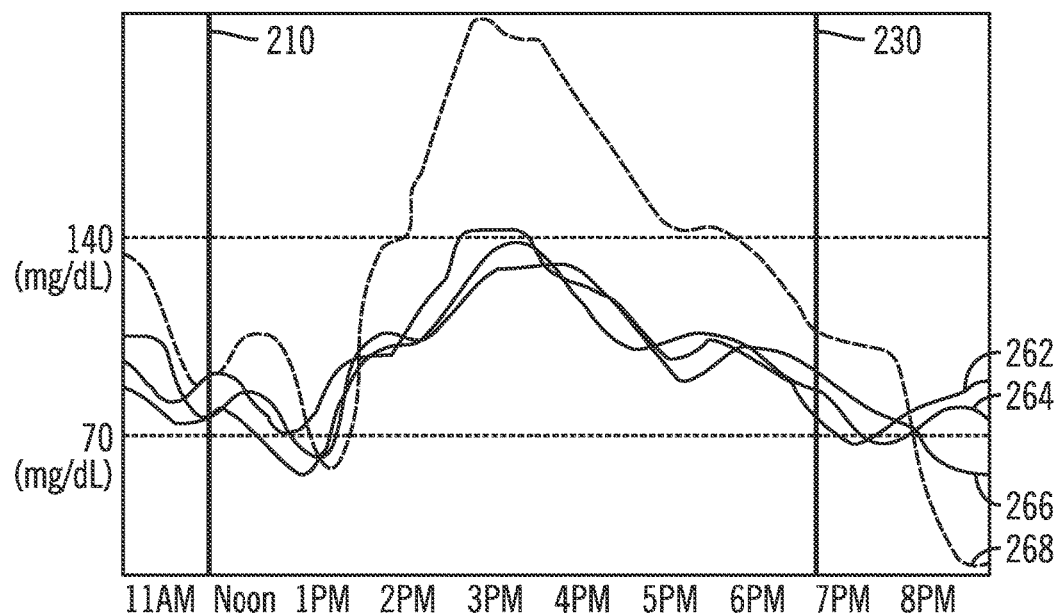
FIG. 2D illustrates a sample report displaying sensor readings according to embodiments of the present invention.

FIG. 2D illustrates a sample report displaying sensor readings according to embodiments of the present invention. Similar to the chart of FIG. 2B above, the chart of FIG. 2D shows three representative lines 262, 264, 266 forming a general pattern, with anomalous line 268 showing an extremely high rise and peak at around 3 PM and a long downward crash towards 8 PM. By analyzing the data in the chart of FIG. 2D, the DDMS/MDMS may determine that anomalous line 268 exhibits a similar pattern as formed by lines 262, 264, 266, except that the glucose level readings of line 268 are more acute and severe in the magnitude of the rise and fall of the glucose levels. Due to any set of events for the particular day (week, month, etc.) that the reading for line 268 was taken, the user may have been particularly sensitive to foods ingested, the user administered a different meal bolus dosage, etc., and caused the anomalous reading of line 268. Alternatively, the anomalous reading of line 268 may have been caused by a hardware issue, for example, by a bias or an overly-sensitive sensor, or by improper operation by the user that exaggerated the readings, or the sensor was mis-calibrated by the user. A hardware issue may be identified, for example, if a set of readings obtained from when the sensor was placed on the user all exhibited similar increased magnitudes, or if there is a known sensitivity with a particular sensor lot number.

One way of determining whether a sensor may be overly sensitive or whether there might have been a calibration issue is to analyze the raw electrical current signal values (Isig) received from the sensor (typically, the higher the Isig value, the higher levels of glucose detected). These values may be stored by, for example, the DDMS/MDMS or any other suitable system. For example, if the Isig values from which the anomalous reading of line 268 was derived was consistent with and matches the range of the Isig values for lines 262, 264, 266, a mis-calibrated sensor may be at issue. But if the Isig values for anomalous line 268 are not consistent with the Isig values for lines 262, 264, 266, for example, if the Isig values for line 268 also share the increased magnitudes like line 268 relative to the Isig values for lines 262, 264, 266, then it is possible that the sensor hardware has a bias or is overly sensitive.

Figure 2E:
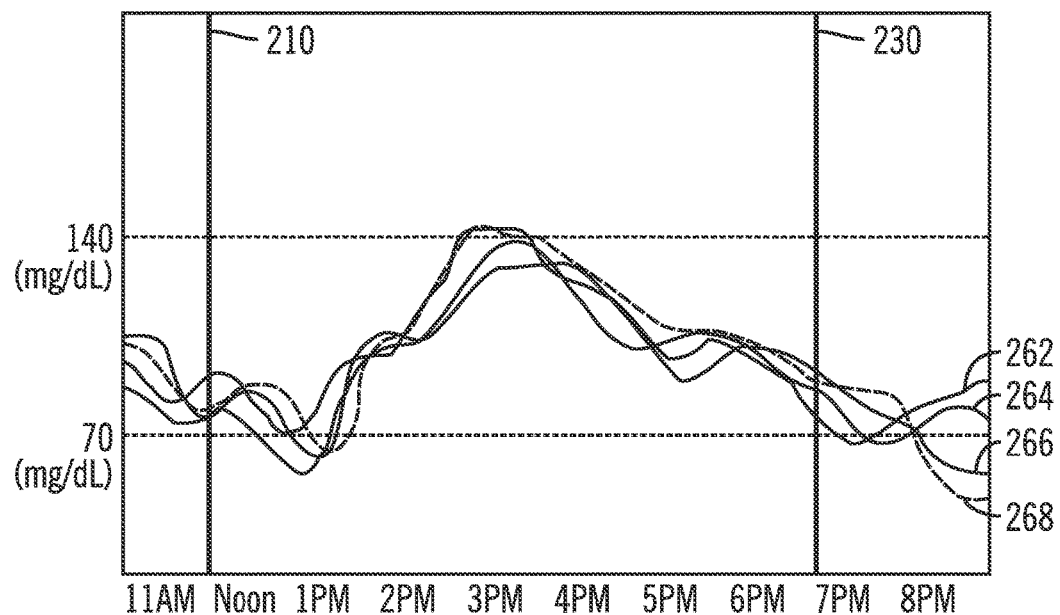
FIG. 2E illustrates an adapted glucose-level-compressed sample report displaying sensor readings from FIG. 2D according to embodiments of the present invention.

By recognizing the general pattern formed by lines 262, 264, 266 and that of anomalous line 268, the DDMS/MDMS may determine that by compressing the anomalous line 268 towards the center target range of desired glucose levels (70 mg/dL to 140 mg/dL), as illustrated in FIG. 2E, the reading of line 268 generally conforms to the pattern formed by lines 262, 264, 266, especially from the period of Noon to 7 PM. For example, if it is determined that the sensor used to obtain the anomalous reading of line 268 was overly sensitive and was providing exaggerated readings in magnitude, compressing anomalous line 268 would normalize this reading to one that would have been obtained had a normally sensitive sensor been used. By compressing line 268 in both directions inwards towards the desired glucose level range, an additional set of data, which was previously considered anomalous and potentially filtered out and excluded, may be included for analysis.

As discussed above with respect to FIGS. 2B and 2C, the analysis may be further enhanced if we know, by direct user input (e.g., setting a "lunch" event occurrence marker) or inferred from a user action (e.g., administering a meal bolus in the afternoon to have lunch), that the user took lunch at Noon on the days (weeks, months, etc.) that lines 262, 264, 266, 268 were read. This type of information would further strengthen the pattern recognition and filtering scheme performed by the DDMS/MDMS in knowing that the reading of line 268 was consistent in time with when the user typically took lunch and that time-shifting in this instance may be unnecessary in the present example (see, e.g., FIG. 2D, that the user may have been just particularly sensitive to foods ingested when the reading of line 268 was taken, underestimated the insulin bolus required for a meal, delayed a bolus of insulin until the glucose level was already increasing, or that an overly sensitive, improperly operated, or mis-calibrated sensor was used), in generating the adapted glucose-level-compressed chart of FIG. 2D.

Figure 2F:
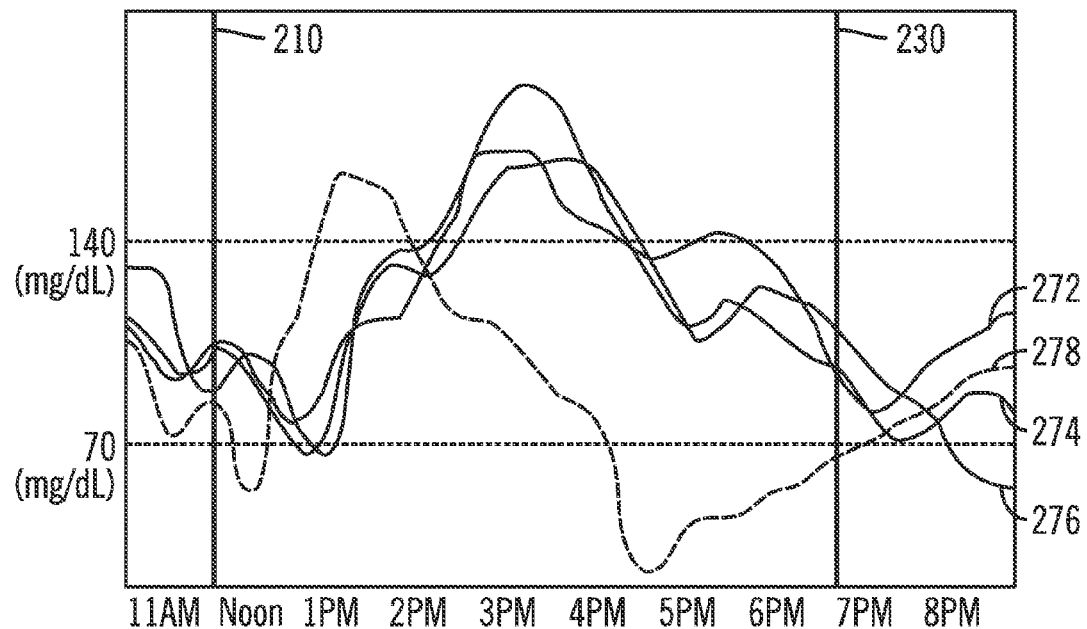
FIG. 2F illustrates a sample report displaying sensor readings according to embodiments of the present invention.

FIG. 2F illustrates a sample report displaying sensor readings according to embodiments of the present invention. Similar to the charts of FIGS. 2B and 2D above, the chart of FIG. 2F shows three representative lines 272, 274, 276 forming a general pattern, with anomalous line 278 showing a rise and peak within about an hour's time, as opposed to about two hours for lines 272, 274, 276. By analyzing the data in the chart of FIG. 2F, the DDMS/MDMS may determine that anomalous line 278 exhibits a similar pattern as formed by lines 272, 274, 276, except that the readings of line 278 appear to have the glucose levels rise and fall at a more rapid rate. Due to any set of events for the particular day (week, month, etc.) that the reading for line 278 was taken, the user experienced a more rapid rise and fall of glucose levels (e.g., eaten lunch in a quarter of the time as usual, ate a different portion and/or type of food, etc.) in the afternoon that caused the anomalous reading of line 278.

Figure 2G:
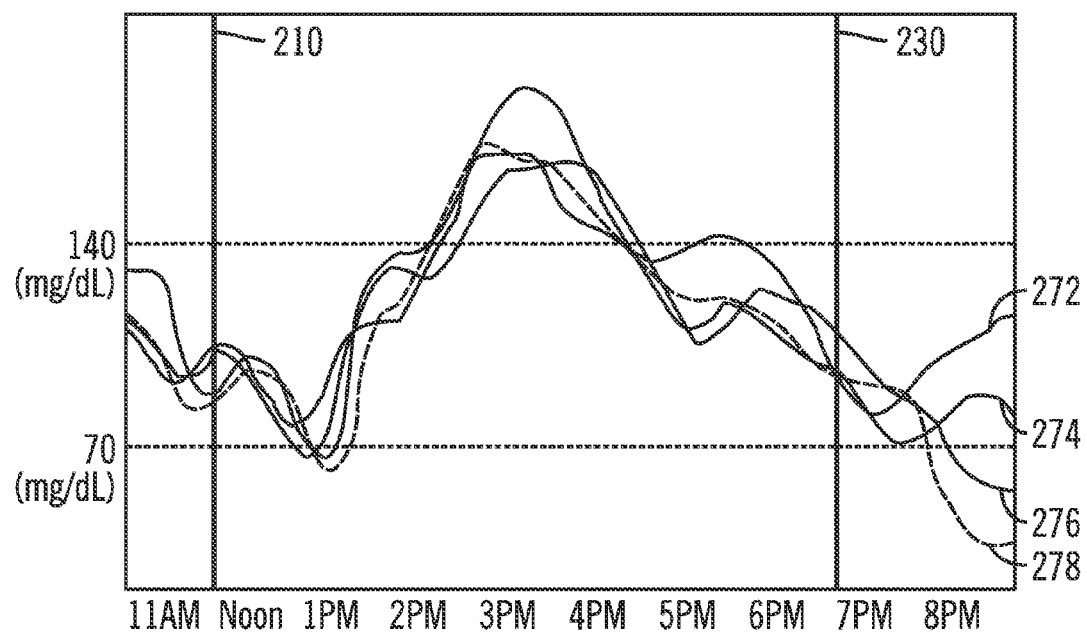
FIG. 2G illustrates an adapted time-stretched sample report displaying sensor readings from FIG. 2F according to embodiments of the present invention.

By recognizing the general pattern formed by lines 272, 274, 276 and that of anomalous line 278, the DDMS/MDMS may determine that by stretching the anomalous line 278 in time, as illustrated in FIG. 2G, the reading of line 278 generally conforms to the pattern formed by lines 272, 274, 276, especially from the period of Noon to 7 PM. According to embodiments of the present invention, we are interested analyzing a "typical" lunch pattern in the present example, and the time-stretching of line 278 would normalize this reading to one that would have been obtained had a typical lunch been taken. Alternatively, a separate analysis may be performed on the anomalous line 278 itself, or in combination with other readings. By time-stretching line 278, an additional data set, which was previously considered anomalous and potentially filtered out and excluded, may be included for analysis.

Figure 2H:
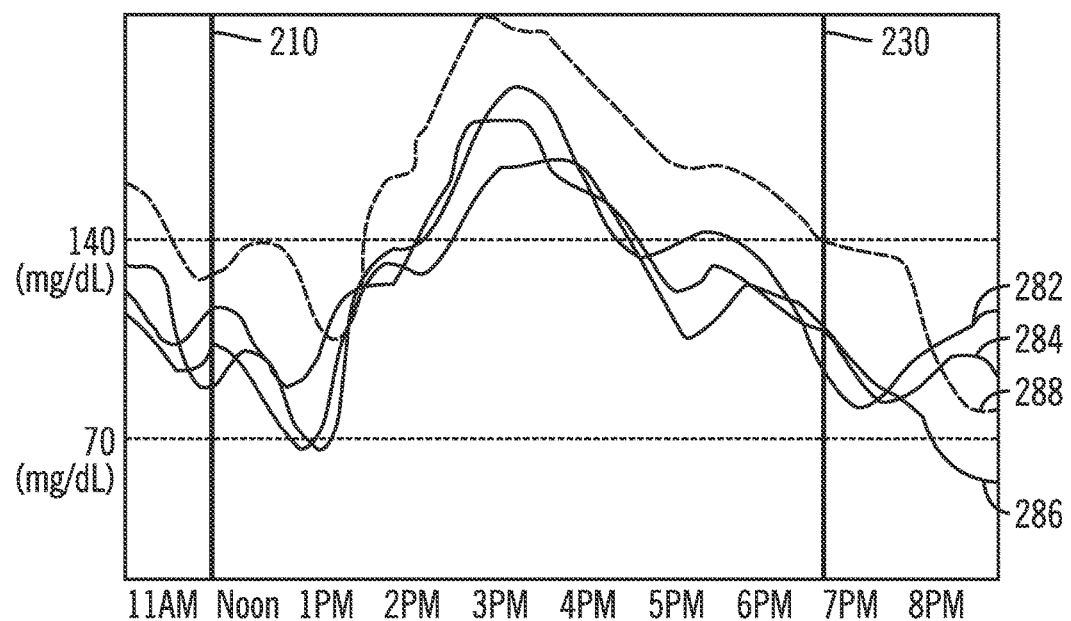
FIG. 2H illustrates a sample report displaying sensor readings according to embodiments of the present invention.

FIG. 2H illustrates a sample report displaying sensor readings according to embodiments of the present invention. Similar to the charts of FIGS. 2B, 2D, and 2F, the chart of FIG. 2H shows three representative lines 282, 284, 286 forming a general pattern, with anomalous line 288 having generally skewed high glucose levels. By analyzing the data in the chart of FIG. 2H, the DDMS/MDMS may determine that anomalous line 288 exhibits a similar pattern as formed by lines 282, 284, 286, except that the readings of line 288 are mostly above the desired glucose levels for the entire period illustrated in the chart of FIG. 2H. Due to any set of events for the particular day (week, month, etc.) that the reading for line 288 was taken, the user was having high glucose baseline levels that caused the anomalous reading of line 288. For example, the user may have set a lower basal insulin rate/pattern, which caused all of the glucose level readings to skew upwards on the higher end since the user made the basal insulin rate/pattern change.

Alternatively, according to embodiments of the present invention, the DDMS/MDMS may detect that the glucose level readings for the past few days have been skewed on the high side, which may infer that there may be a problem with the sensor (e.g., the sensor may be overly sensitive, improperly operated, mis-calibrated, etc.), and the user may be alerted to check the sensor to make sure that it is functioning properly. Any suitable techniques to diagnose a potentially overly sensitive or improperly operated sensor, or identify a mis-calibration, including analyzing the Isig values as discussed above with respect to FIGS. 2D and 2E, may be utilized.

Figure 2I:
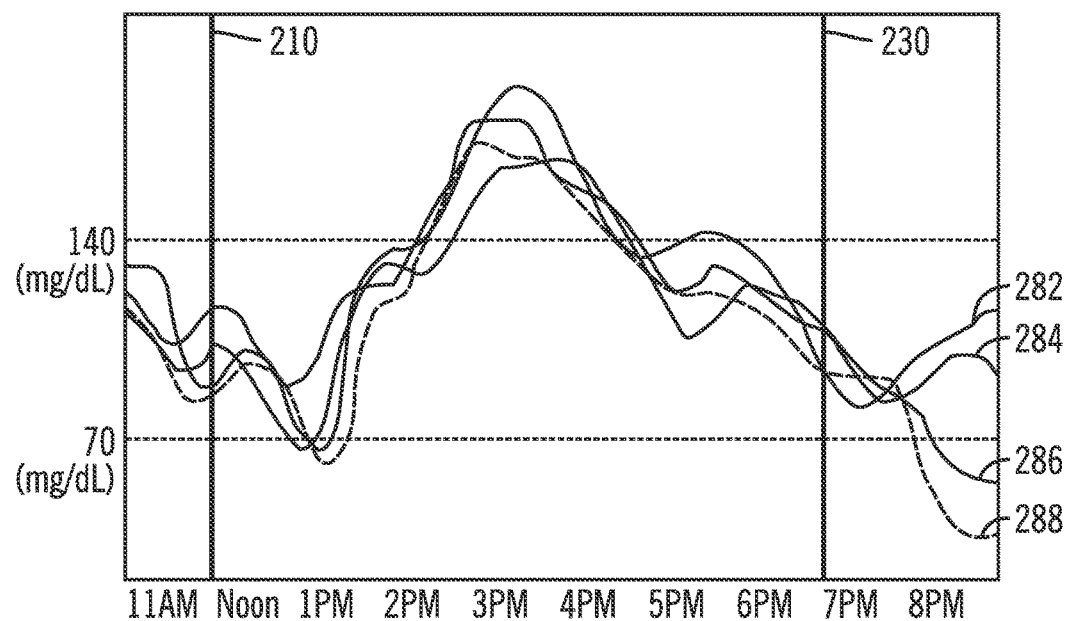
FIG. 2I illustrates an adapted glucose-level-shifted sample report displaying sensor readings from FIG. 2H according to embodiments of the present invention.
Figure 2J:
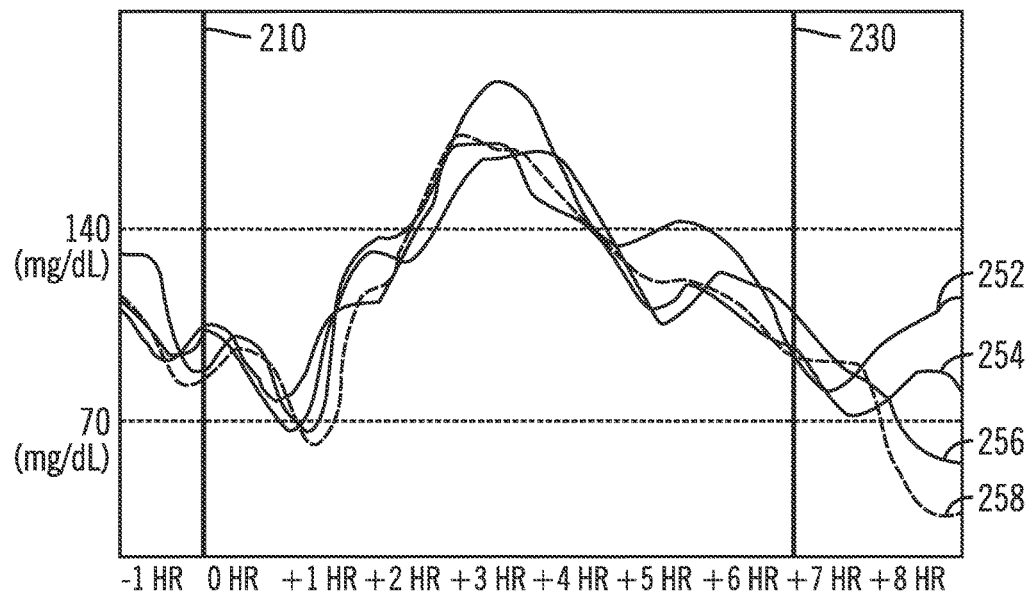
FIG. 2J illustrates an adapted time-shifted sample report displaying sensor readings from FIG. 2C utilizing a relative time line according to embodiments of the present invention.
Figure 2K:
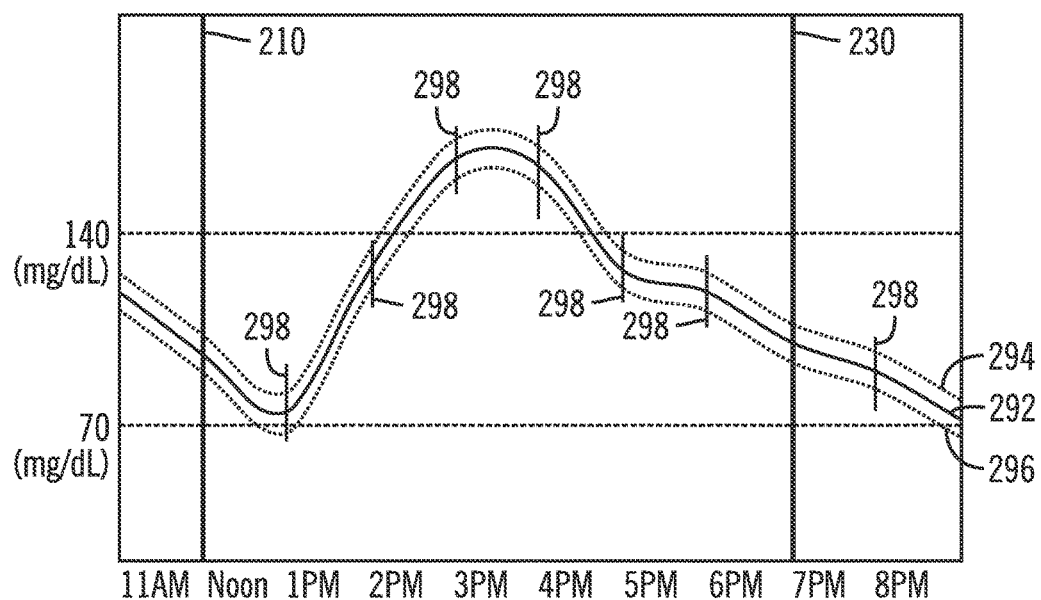
FIG. 2K illustrates a report showing an average glucose level reading, standard deviation, and high-low lines of the adapted time-shifted sample report of FIG. 2C according to embodiments of the present invention.

By utilizing pattern recognition algorithms to determine the general pattern formed by lines 282, 284, 286 and that of anomalous line 288, the DDMS/MDMS may determine that by shifting downwards the anomalous line 288 towards the center target range of desired glucose levels (as the user was "running high" due to being ill or under stress, or perhaps due to an overly sensitive, improperly operated, or mis-calibrated sensor, or a lowered basal insulin rate, etc.), as illustrated in FIG. 2I, the reading of line 288 generally conforms to the pattern formed by lines 282, 284, 286, especially from the period of Noon to 7 PM. By shifting downwards line 288, an additional data set, which was previously considered anomalous and potentially filtered out and excluded, may be included in the analysis.

Although the anomalous lines 258, 268, 278, 288 in FIGS. 2B and 2C, 2D and 2E, 2F and 2G, and 2H and 2I, respectively, were adapted by the DDMS/MDMS by making a single adjustment (i.e., time-shift, compress by glucose level, stretch by time, shift by glucose level) to the anomalous lines 258, 268, 278, 288, according to embodiments of the present invention, the DDMS/MDMS may make more than a single adjustment (e.g., time-shift and compress by glucose level, stretch by time and shift by glucose level, etc., or any combination thereof), and/or make other types of adjustments than those discussed above, to one or more of the lines as appropriate. Moreover, these adjustments may be made for glucose level readings in any other time period other than from 11 AM to 9 PM, as illustrated in FIGS. 2B-2I and 2K, too. An anomalous reading not adapted to a pattern by the DDMS/MDMS may be filtered out and excluded from analysis, or analyzed separately, independently or with other readings.

Figure 3:
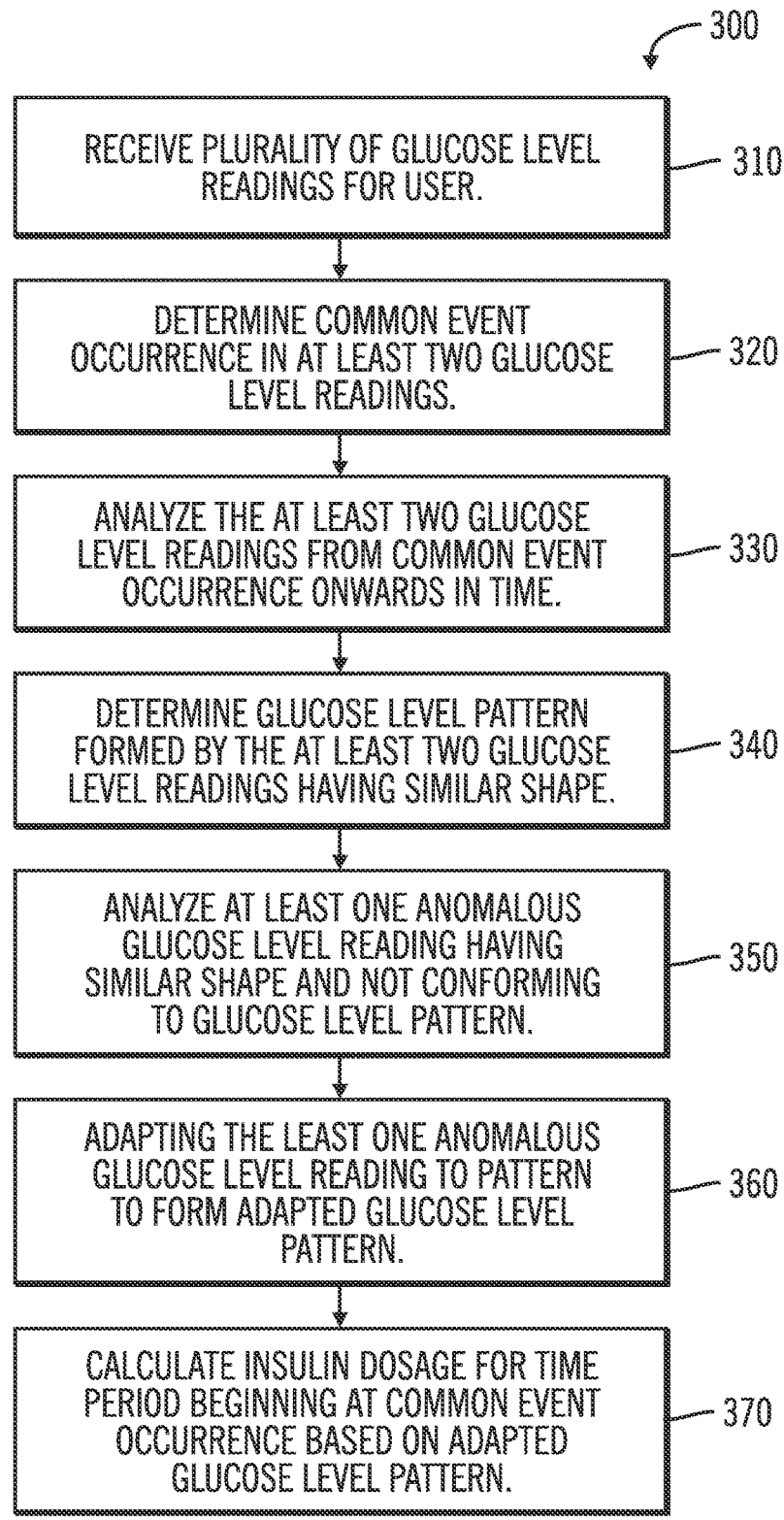
FIG. 3 illustrates a flowchart for applying pattern recognition and filtering algorithms for diabetes analysis according to embodiments of the present invention.

FIG. 3 illustrates a flowchart for applying pattern recognition and filtering algorithms for diabetes analysis according to embodiments of the present invention. According to embodiments of the present invention, a method of diabetes analysis includes, at step 310, receiving a plurality of glucose level readings for a user. The glucose level readings (e.g., daily 24-hour glucose level readings for a plurality of days as in FIG. 2A) may be obtained via a DDMS/MDMS system as discussed with respect to FIG. 1 above, or by any other suitable methods and means. According to embodiments of the present invention, the data used for analysis may exclude data from the most recent days. For example, if a user is learning a new behavior, then the most recent days may not generate the same patterns as previously, and data from a more consistent time in a user's life may generate more useful patterns for analysis and treatment planning. At step 320, a common event occurrence in at least two of the glucose level readings is determined. These common event occurrences may be used as reference/anchoring points in time (e.g., starting points, mid-points, end points) to analyze the glucose level readings amongst all of the readings relative to each common event occurrence, and trends and patterns may be perceived as to certain tendencies that may occur for a user relative to these specific event occurrences in that user's life (e.g., breakfast, lunch, dinner, watching the evening news, delivering a meal or correction bolus, etc.).

At step 330, the at least two glucose level readings from the common event occurrence onwards in time for a time period is analyzed to determine, at step 340, whether there is at least one glucose level pattern formed by the at least two glucose level readings having a similar shape. By analyzing the data, for example, in the representative charts illustrated in FIGS. 2B-2K, the DDMS/MDMS may determine that a pattern having a similar shape of two small successive dips followed by a large rise in glucose levels exist for several of the glucose level readings. This particular pattern of dips and rises is merely an illustrative example, and according to embodiments of the present invention, any other patterns and types of patterns may be analyzed.

At step 350, at least one anomalous glucose level reading having the similar shape and not conforming to the glucose level pattern is analyzed. For example, referring to FIGS. 2B-2J, glucose level reading lines 258, 268, 278, 288 appear to be anomalies such that they generally share the similar shape and slopes as with the remaining glucose level readings in their respective charts, but these anomalous lines do not conform to the pattern formed by the other glucose level readings in their respective charts. The at least one anomalous glucose level reading may be adapted to the pattern, at step 360, by the DDMS/MDMS to form an adapted glucose level pattern, for example, as illustrated in FIGS. 2C, 2E, 2G, 2I. According to embodiments of the present invention, at step 370, an insulin dosage for the time period beginning at the common event occurrence may be calculated based on the adapted glucose level pattern.

Figure 4:
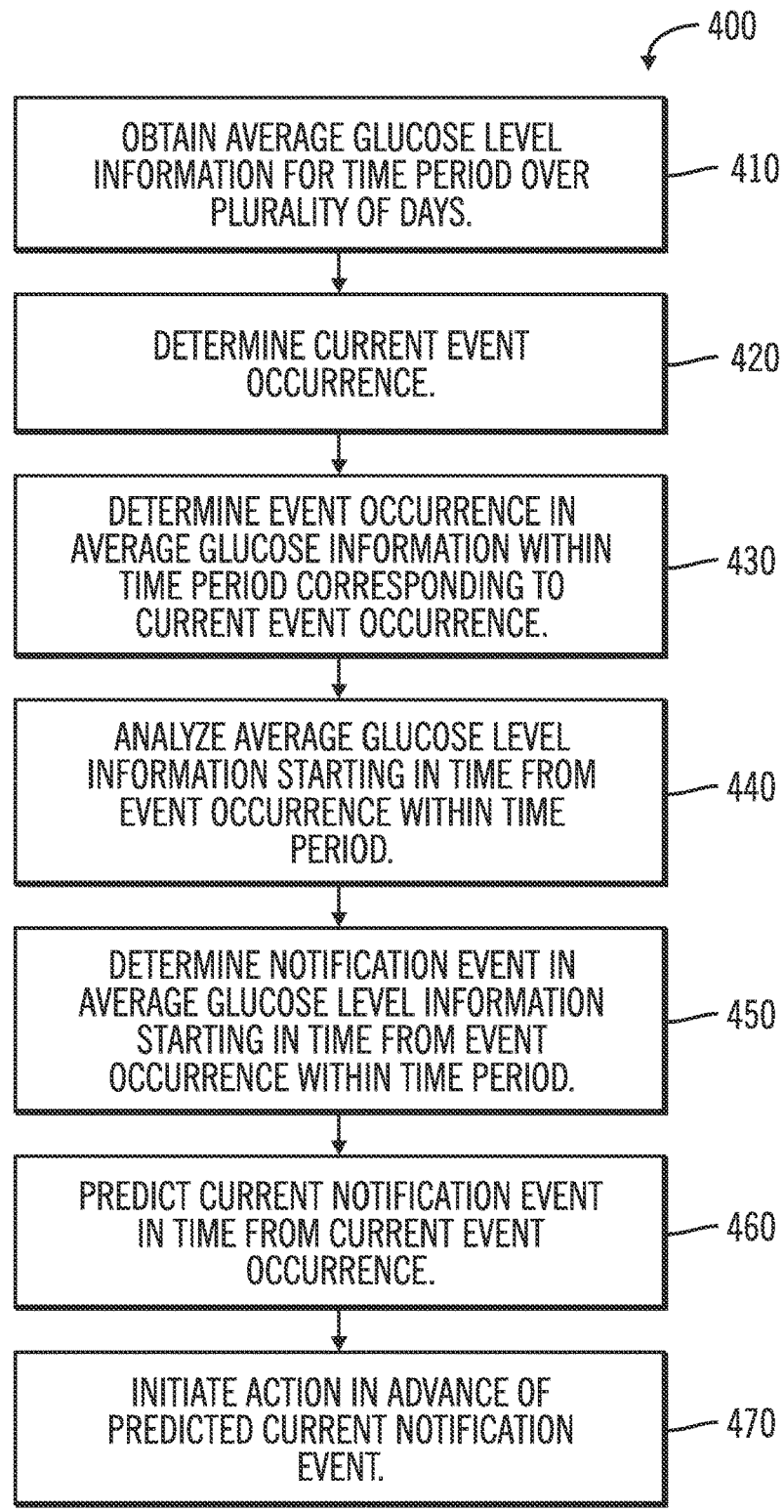
FIG. 4 illustrates a flowchart for diabetes analysis according to embodiments of the present invention.

FIG. 4 illustrates a flowchart for analysis of diabetes information according to embodiments of the present invention. According to one embodiment of the present invention, a method of analysis using time-shifted patterns of average glucose level information includes, at step 410, obtaining average glucose level information for a time period over a plurality of days. A chart, for example, like in FIG. 2A, of overlapping glucose level information for a period of days (e.g., 28-days in FIG. 2A) to obtain average glucose level information for a 24-hour time period may be utilized. Next, at step 420, a current event occurrence is determined (e.g., breakfast, lunch, or dinner, watching the morning/evening TV news, having afternoon tea, etc.).

Assuming that the user is about to have lunch (the current event occurrence), at step 430, an event occurrence (i.e., lunch at Noon shown at line 210 in FIG. 2A) in the average glucose level information within the time period corresponding to the selected current event occurrence (i.e., lunch now) is determined. The current event occurrence (lunch now) is at a different time of day than the event occurrence. For example, the user took lunch at Noon every day in the 28-day report of FIG. 2A, and the average glucose level information in FIG. 2A reflects that the user took lunch at Noon each day during this 28-day period. However, in the present example, the user was caught in a business meeting that ran long and the user is now taking lunch an hour later than usual, at 1 PM. Embodiments of the present invention are also applicable if the current event occurrence occurs earlier than the event occurrence in the average glucose level information (e.g., the user took lunch at 11:30 AM instead of Noon).

At step 440, the average glucose level information starting in time from the event occurrence (i.e., lunch at Noon shown at line 210 in FIG. 2A) within the time period is analyzed. That is, the average glucose level information pattern from the event occurrence onwards is analyzed to determine whether there is, at step 450, a notification event in the average glucose level information starting in time from the event occurrence within the time period. For example, the average glucose level information in FIG. 2A is analyzed to see whether there is a notification event (i.e., a significant, alarm, or any other event that may be of interest to the user, a medical professional, researcher, etc.). In the example illustrated in FIG. 2A, we note that there is a pattern in which the user's average glucose level tends to rise and peak shown at line 220 about three hours after the start of lunch at Noon shown at line 210, constituting a notification event in the present example.

Based on the time-shifted pattern according to embodiments of the present invention, at step 460, a current notification event in time from the current event occurrence (i.e., lunch now at 1 PM) is predicted based on a time span from the event occurrence (lunch at Noon shown at line 210 from report 200 in FIG. 2A) and the notification event (rise and peak shown at line 220 in FIG. 2A) from the average glucose level information in FIG. 2A. In the present example, the user took lunch at 1 PM instead of the usual Noon lunch time, and given that the 28-day average glucose level pattern in FIG. 2A shows a rise and peak at line 220 occurring three hours after the start of lunch at Noon shown at line 210, according to embodiments of the present invention, this pattern starting at lunch at Noon shown at line 210 onwards may be time-shifted an hour later to predict that a similar current notification event of a rise and peak three hours following the start of lunch would be approximately 4 PM. From this prediction, at step 470, an action may be initiated in advance of the predicted current notification event that is forecasted to occur around 4 PM, three hours after starting lunch at 1 PM.

Accordingly, in the present example as illustrated in FIG. 2A, the average glucose level pattern shows that a rise starts at 1 PM, an hour after the start of lunch at Noon shown at line 210. Therefore, if the user in this instance started lunch at 1 PM, an hour later than usual, an action may be taken to alert the user of a predicted rise that will start at approximately 2 PM, an hour after taking lunch. The user may be instructed to temporarily increase the basal rate for the next few hours or to deliver a bolus to minimize the rise and peak as predicted from the time-shifted average glucose level pattern (e.g., the "afternoon" pattern), or if so configured, to automatically increase the insulin delivery rate (basal or temporary) or administer a bolus, during this predicted rise and peak period so as to keep the user's glucose levels as stable as possible and within the desired glucose level range.

A pattern that may be time-shifted may constitute the entire 24-hour period of the average glucose levels, as illustrated in FIG. 2A, or any portion thereof. For example, the 24-hour period may be partitioned into three patterns for time shifting purposes, corresponding to three main meals per day (breakfast, lunch, and dinner), each pattern beginning at the start of an event occurrence (breakfast, lunch, or dinner) and ending right before the start of the next event occurrence. Referring to FIG. 2A, if we know that the user usually has breakfast at 6 AM shown at line 240, then one pattern may constitute the average glucose levels from 6 AM to Noon (the breakfast/morning pattern), and then a second pattern may constitute the average glucose levels from Noon (lunch time shown at line 210) to 7 PM (the lunch/afternoon pattern), and lastly a third pattern may constitute the average glucose levels from 7 PM (dinner time shown at line 230) to 6 AM the next day (the dinner/evening pattern). Each of these three patterns may be used for time-shifting purposes to predict potential notification events; a single 24-hour pattern or any portion thereof, divided into any number of patterns, corresponding to any suitable event occurrence, may be utilized according to embodiments of the present invention. Insulin dosage/delivery patterns may be programmed, e.g., in an insulin pump or any other suitable device, to match the representative patterns generated above, such that the user may be able to select, for example, a "breakfast", "lunch", or "dinner" insulin delivery pattern at the appropriate time or event to deliver insulin to keep the user's glucose levels as stable as possible and within the desired range.

Patterns and time lines are often helpful in linking causes to effects. Rates of change (e.g., what is the highest point we can reach before we need to make a correction) are often helpful in determining a significant or triggering event. Inappropriate alarm settings, for example, may lead to behaviors that may be detrimental to therapy. Inappropriate alarm settings may be ignored by the user, and then when a real critical alarm event occurs, the user may ignore this important alarm event as well (i.e., "crying wolf"). Therefore, making sure that the data is accurate is important in reducing the occurrence of inappropriate false alarms that may train "bad" behaviors in the user.

Factors that may influence the data quality used to develop a treatment plan may include: use of finger sticks to determine glucose levels, use of glucose sensors, use of accurate carbohydrate estimate counts, use of properly placed markers such as meal, activity, medication, stress, etc., and accurate insulin delivery. Most of these factors provide enough data in themselves that treatment plans based on these factors are generally reliable. Other factors that may influence the data quality and a user's adherence to the treatment plan may include: how often an infusion set is changed, how often calibration of the various medical devices are performed, common deceptions (e.g., over-priming an infusion pump), quality of the bolus calculator recommendations and overrides applied by the user. If a user is not following the bolus calculator recommendations, then a doctor may infer that the settings for the bolus calculator are not accurate and/or helpful, and may be prompted to reset them to be more accurate.

Various effects or conditions may result due to different treatment actions or causes, including hyperglycemia and hypoglycemia (both of which may influence pattern strength and pattern severity), and rising and falling glucose levels, including sharp spikes and drops (which may result from "unmarked" meals). Actions or causes for these varies conditions or effects applied in treatment may include: the basal (pattern) vs. bolus (impulse) settings, which in turn are influenced by the bolus impulses administered, use of carbohydrate ratios, a person's insulin sensitivity, the active insulin already administered to a person, as well as the time of day (e.g., late afternoon, evening, etc.), and whether or not a person is active or ill, under stress, etc. Delivery of a bolus resulting from a bolus calculator recommendation, suspension of delivery of insulin, or setting a temporary basal rate may also have effects on a person's glucose levels. Alarms may be tied to the occurrence of varies events, too.

If a database of "Bolus Type=Effect" information is available, some predictions may be made such that when a person encounters a particular event or pattern, based on the database information and recognizing the event or pattern occurring, a particular bolus type that can mitigate the undesired event or pattern may be recommended based on past data from the user or a plurality of users. Additionally, if the user exhibits a particular glucose level pattern following a particular event or activity, e.g., a meal, an 20-minute afternoon nap, a particular type of exercise, etc., we may adjust the user's basal rate (especially if we know the user's current insulin-on-board and glucose level) based on the observed patterns in advance of the user performing the particular activity, e.g., doing three sets of 15 pull-ups, running a mile on the treadmill at a 6.5 MPH pace, etc., to keep the user's glucose levels as stable as possible and within the desired range.

Other methods of managing therapy may include the use of a "virtual patient". A virtual patient is a digital model of an actual human patient on a computer to simulate different ways diabetes, or any other medical condition, affects the body, and how various treatments may potentially affect the virtual patient. Virtual patients may help cut the time and costs of development and testing of new treatment plans. For example, by knowing a patient's insulin sensitivity (everyone has different insulin sensitivities, and for Type I diabetics, e.g., they are often more sensitive in the late afternoons), certain predictions may be made and patterns from the virtual patient may be identified and tested to see if they are close to real life. Further description of a virtual patient software system may be found in U.S. Pat. App. Pub. No. 2006/0272652, published Dec. 7, 2006, to Stocker et al. and entitled "Virtual Patient Software System for Educating and Treating Individuals with Diabetes", which is herein incorporated by reference in its entirety.

Doctors often have access to data of multiple patients. By comparing the data of multiple patients in a doctor's patient pool, group patterns may be developed that may be helpful in treating particular patients. Similar patterns in multiple patients may help a doctor plan a course of treatment that may help another patient having such similar patterns. Data from multiple patients in a doctor's care may be utilized for virtual patient simulations, too, along with developing an "average patient" model as a point of reference.

Group patterns may be filtered by sex, age, pregnancy state, exercise type, body type, type of diabetes (Type I, Type II, gestational), treatment type (pump use, insulin type use, oral medication), etc. Another group may involve "panic" users, those who tend to over-deliver boluses upon a triggering or notification event. Accordingly, the infusion pump, controller/programmer, or any other suitable device may be configured such that when it recognizes a glucose level pattern occurring that has historically lead to a user over-delivering insulin, the infusion pump may warn the user in advance of this triggering event to not over-deliver a bolus. Additionally, the infusion pump, controller/programmer, or DDMS/MDMS, may automatically disable itself for a short period of time after the proper dosage has been delivered to prevent over-delivery by a panicked user. Group patterns also may be useful in assessing and identifying a "type" of patient, particularly helpful in establishing a starting point for a new patient.

"Distracted" users may forget to treat diabetes by skipping boluses, eating high sugar foods, forgetting to turn on the insulin pump after suspending insulin delivery during exercise, or forgetting to calibrate a sensor before bedtime (which may lead to the user being awakened during the night for a calibration). Patterns may be used to quickly identify that a bolus was missed or that a high sugar drink was consumed and warn the user to deliver a bolus before glucose levels reach severe hyperglycemia. Likewise, patterns may be used to identify early that exercise has stopped and the pump's bolus delivery must resume. Similarly, patterns may be used to identify habitual lapses in compliance and remind the user to perform a task when the user is awake and when it is convenient.

A user's exercise regime also should be considered when planning a course of treatment. An infusion pump or controller/programmer, for example, may include an accelerometer, heart rate monitor, respiratory monitor, etc., to deduce when a user may be exercising. Sometimes a user will remove a pump just before undergoing exercise, or set a temporary basal rate just before exercising to prevent a drop in glucose levels. Further descriptions of utilizing accelerometers in diabetes therapy may be found in U.S. Pat. App. Pub. No. 2008/0125701, published May 29, 2008, to Moberg et al. and is entitled, "Methods and Apparatuses for Detecting Medical Device Acceleration, Temperature, and Humidity Conditions", which is herein incorporated by reference in its entirety.

As with patterns of glucose levels, patterns of insulin delivery, e.g., basal patterns, also may be established corresponding to the glucose level patterns to keep the glucose levels within the desirable range throughout the day. Based on a glucose level pattern, an insulin delivery pattern may be established to anticipate and "match" rises and falls and keep the glucose levels within the desired range. Multiple patterns may be established for varies times throughout the day, too. For example, there may be an "after breakfast" pattern, an "after lunch" pattern, an "after dinner"/overnight pattern, etc. One pattern may be more useful to a user than another, and if a doctor sees that a user is using one pattern but not another, the doctor may deduce that the other unused pattern is not configured correctly and may further adjust this pattern to make it more effective to the user.

According to embodiments of the present invention, an after dinner/overnight pattern may be used to evaluate whether a user must take an action before bedtime. For example, if a user exercises earlier in the day, his/her body may demand nutrition to heal while sleeping, and the user's glucose levels may drop during the night to hypoglycemic levels. We may observe patterns of the glucose levels before bedtime and during the night, and if a hypoglycemic pattern is identified before going to bed, the user may take action to prevent low glucose levels, such as eating a snack before bedtime, eating a fatty snack so that digestion is postponed, reducing the basal insulin amount, changing the basal insulin profile, setting an alarm to get a snack later, etc.

The more accurate a user is at making an estimate of his/her carbohydrate intake, the more accurate the delivery of the correct amount of insulin required to keep a user's glucose levels stable and within the desired range. The Medtronic MiniMed BOLUS WIZARD™ calculator, for example, is a bolus estimator/calculator that assists a user in providing a recommended insulin bolus dosage for a meal based on the user's estimate of the amount of carbohydrates in a meal to be consumed. Further descriptions of a bolus calculator may be found in U.S. Pat. No. 6,554,798, issued Apr. 29, 2003, to Mann et al. and is entitled, "External Infusion Device with Remote Programming, Bolus Estimator and/or Vibrational Alarm Capabilities", and U.S. Pat. No. 7,204,823, issued Apr. 17, 2007, To Estes et al. and is entitled, "Medication Delivery System and Monitor", which are herein incorporated by reference in their entirety. Certain people are more accurate at estimating the amount of carbohydrates in a particular food or food type than others. For example, some people are better at estimating the carbohydrate amount in foods with generally high carbohydrate counts (e.g., potatoes) than those with the lower ones (e.g., eggs).

According to embodiments of the present invention, a bolus calculator may be calibrated ahead of time by the user to learn of the user's biases and tendencies to estimate high or low for certain (or all) foods (e.g., an apple, orange juice, pepperoni pizza, baked salmon, steamed rice, etc.) and food types (e.g., grains, vegetables, fruits, dairy products, meats, etc.), and then adjust the recommended insulin bolus dosage based on the user's biases and tendencies (if any). For example, the bolus calculator may be calibrated using a computer, such as the DDMS/MDMS discussed above with respect to FIG. 1, or the like, which may display a variety of different portions of foods with known true carbohydrate counts, and ask the user to provide his/her own estimates of the carbohydrate counts for the foods (and portions/amounts thereof) presented. By comparing the user's estimated carbohydrate count with the known true carbohydrate count for a variety of different foods, food types, food subtypes, etc., a calibration may be made to assist in providing more accurate insulin bolus dosage recommendations.

For example, it can be determined that the user estimates higher than true carbohydrate counts for pizza in general, while the user provides accurate estimates with meats and wheat-based foods in general, but the user underestimates the carbohydrate counts for sushi and fruits in general. Based on this calibration, the bolus calculator may adjust the insulin dosage recommendations to compensate for the user's biases in estimating high or low for particular foods and food types, and make little or no adjustments when the user is known to make accurate estimates for other foods and food types. Therefore, the bolus dosage recommendation is increased if the user's response to estimate the carbohydrate value for a representative food corresponding to a food to be consumed is lower than the true carbohydrate value for the representative food during calibration. Likewise, the bolus dosage recommendation is decreased if the user's response to estimate the carbohydrate value for a representative food corresponding to a food to be consumed is higher than the true carbohydrate value for the representative food during calibration. Any particular foods, food types, and food subtypes (e.g., for grains—wheat foods, rice foods, etc.) are suitable for calibration of the user's ability to estimate accurately carbohydrate counts for the various foods, food types, and food subtypes the user wishes to consume.

According to embodiments of the present invention, the bolus calculator may permit the user to select and calibrate with favorite foods or those foods that are commonly eaten by the user to obtain the most accurate and useable bolus dosage recommendations. For example, if the user hates or has severe allergies to shrimp foods, then, there is no need to calibrate with shrimp foods. The bolus calculator may also permit the user to designate an origin of the foods and calibrate accordingly, e.g., calibrate a pizza from California Pizza Kitchen vs. a pizza from Domino's vs. a frozen pizza from Costco. The bolus calculator may even permit the user to calibrate specific foods, e.g., a pepperoni and green pepper pizza (from Domino's) vs. a sausage and mushroom pizza (from Costco). Any combinations of the foods, food types, food subtypes, specific foods, and their origins, brands, etc. may be incorporated into the bolus calculator for calibration of the bolus calculator based on the user's ability to accurately estimate carbohydrate counts and adjust the bolus dosage recommendations based on those estimates.

Figure 5:
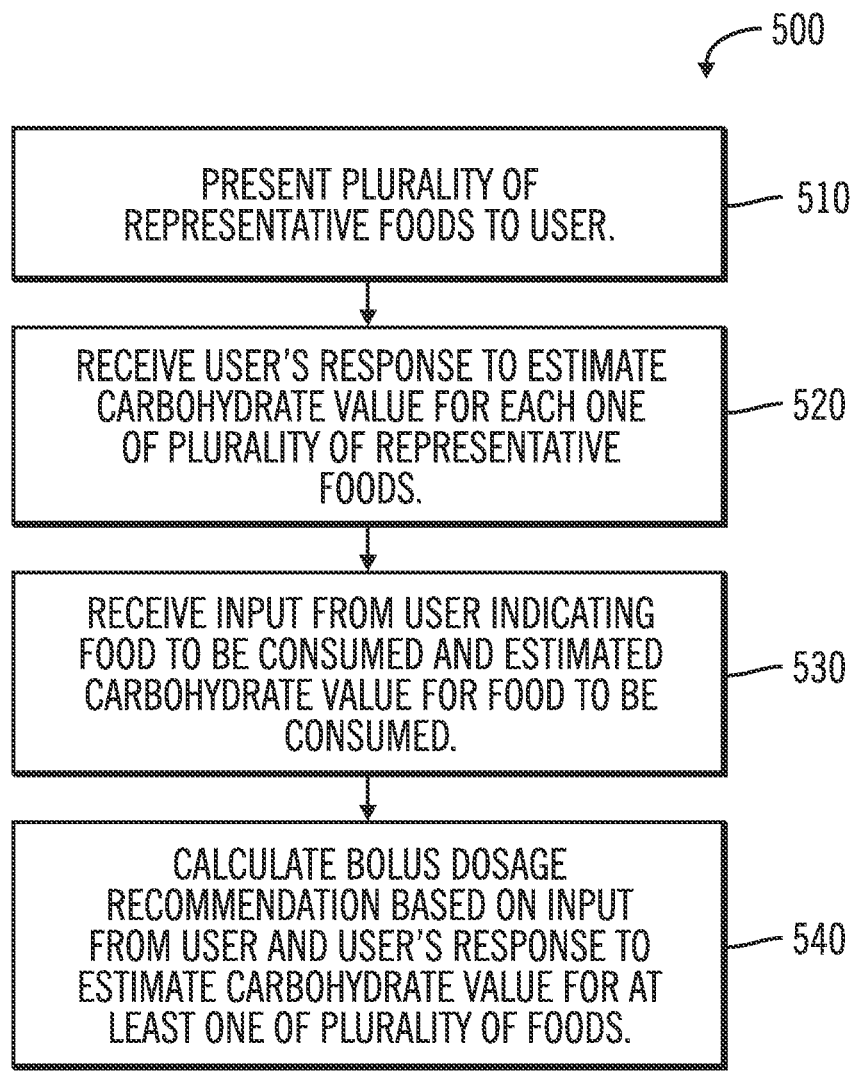
FIG. 5 illustrates a flowchart for providing bolus dosage recommendations for diabetics according to embodiments of the present invention.

FIG. 5 illustrates a flowchart for providing bolus dosage recommendations in diabetes therapy according to embodiments of the present invention. According to embodiments of the present invention, a method of calibrating and providing bolus dosage recommendations in diabetes therapy includes, at step 510, presenting a plurality of representative foods to a user. A spectrum of representative foods (especially those foods that a user is likely to consume) is selected and presented to the user that is reflective of the typical diet of the user. For example, these foods may be presented on a display of a computer or other suitable device, including but not limited to the DDMS/MDMS described above with respect to FIG. 1. The user is then prompted to estimate a carbohydrate value for each one of the plurality of representative foods presented to the user. The user may account for the portion (large, small, two vs. three egg omelet, etc.) of the representative foods presented to the user when estimating the carbohydrate value. Alternatively, the user may respond with "N/A", "SKIP", "REMOVE", or the like for those representative food(s) presented to the user that the user does not commonly eat or enjoy, to which the user has allergies, is not readily available where the user lives, etc.

At step 520, the responses from the user are received and stored by the computer or other suitable device. These responses are then used to calibrate a bolus calculator to determine whether the user has a tendency or bias to estimate high or low for particular foods, food types, food subtypes, etc. from their true carbohydrate value. Based on the estimates received from the user during calibration, the bolus calculator may make any adjustments or corrections in providing bolus dosage recommendations.

When the user is about to consume a food item, the user provides information to the bolus calculator indicating a food to be consumed and the user's estimated carbohydrate value for that food to be consumed. The bolus calculator, receiving the information regarding the food to be consumed at step 530, may be the computer that was used in the calibration, a separate device (e.g., a PDA, portable computer, mobile phone, etc.), or even integrated into the infusion pump or controller/programmer (that may receive calibration information from a computer used to conduct the calibration of the bolus calculator). The bolus calculator at step 540 calculates a bolus dosage recommendation based on the input received from the user regarding the food to be consumed (e.g., food, food type, food subtype, estimated carbohydrate count, portion, origin, brand, etc.) and the user's response to estimate the carbohydrate value for at least one of the plurality of representative foods during calibration in steps 510 and 520.

FIGS. 6.1 and 6.2 illustrate Interpretation Reports according to embodiments of the present invention. Referring to the Interpretation Report 610 in FIG. 6.1, information for seven days (although any number of days may be displayed according to embodiments of the present invention) pertaining to blood glucose readings and averages, for example, taken from a blood glucose meter, is displayed in a 24-hour chart (any suitable time period is acceptable according to embodiments of the present invention), highlighting meal events (e.g., breakfast, lunch, dinner). The corresponding infusion device settings for basal rate, insulin sensitivity, and the carbohydrate ratio information (more or less settings may be provided according to embodiments of the present invention) along the 24-hour timeline are also provided under the main chart. Below that information in this Report 610 are close-up charts for the overnight time period, as well as the meal time periods of breakfast, lunch, and dinner (although close-up charts for any other suitable time period may be analyzed, too, according to embodiments of the present invention).

Based on the blood glucose information obtained from these charts, systems and methods according to embodiments of the present invention analyze the data, much like what a doctor would do, and provide an "interpretation" of the raw data in an easy to read table, see, for example, on the upper right corner of the Interpretation Report 610. A quick glance of the interpretation table provides a medical professional a good snapshot of the important statistics in a patient's therapy. Basic information extracted from the raw data may include, for example, average glucose level and an estimated HbA1c value. The raw data may be interpreted, according to embodiments of the present invention, to report instances of hypoglycemic events (time periods of occurrence), instances of hyperglycemic patterns (time periods of occurrence), and instances of high variability in the patient. Key metrics of the patient's infusion device usage (e.g., insulin total daily dose (TDD), basal-bolus ratio, frequency of site/reservoir changes, basal duration, boluses made, and food-and-correction insulin) and the number of blood glucose readings taken each day may also be included in the interpretation table. Further recommendations based on the analyzed raw data may be provided by the Interpretation Report 610 under the Clinical Plan section (see lower right section of Report 610) according to embodiments of the present invention. The statistics provided in the interpretation table of the Report 610 are merely representative examples, and greater or lesser statistics may be provided according to embodiments of the present invention.

The Interpretation Report 610 of FIG. 6.2 according to embodiments of the present invention includes a pie chart section 620 in lieu of the close-up charts for the overnight time period and meal time periods as illustrated in FIG. 6.1. These pie charts 620 illustrate the occurrences of when the percentage of time the patient is "above", "in range", or "below" the target blood glucose levels during various time periods, e.g., Wake-up, Breakfast, Lunch, Dinner, Overnight (although any suitable time period may be analyzed in pie chart form other than the representative ones in FIG. 6.2). The Interpretation Reports of FIGS. 6.1 and 6.2 automatically analyze the raw data regarding a patient's therapy to generate and present the information in an easy to read format for the medical professional, patient, and the like.

FIG. 7.1 illustrates a Therapy Management Dashboard according to embodiments of the present invention, and FIG. 7.2 illustrates an Episode Summary according to embodiments of the present invention. The Therapy Management Dashboard 710 in FIG. 7.1 illustrates in the top chart 24-hour continuous glucose sensor readings from May 2, 2009 to May 29, 2009 of a representative patient. Any suitable time period other than 24-hours may be utilized, as well as any number of days. Below these readings is a second chart providing information with respect to basal rate and active insulin for the corresponding time periods in the 24-hour glucose sensor readings chart above. Below that information are close-up charts, similar to those in FIG. 6.1, for the Bedtime-to-Wake-up time period, as well as the meal time periods of breakfast, lunch, and dinner (although close-up charts for any other suitable time period may be analyzed, too). Information pertaining to therapy statistics (e.g., average blood glucose level, estimated HbA1c level, number of blood glucose readings taken per day, number of carbohydrates entered per day), hypoglycemic patterns (time periods of occurrence), hyperglycemic patterns (time periods of occurrence), infusion device usage (e.g., insulin total daily dose (TDD), basal/bolus ratio, units of manual boluses, Bolus Wizard (BZW) usage, pump suspend duration, low suspend events and duration, and reservoir/set changes), and sensor use (e.g., sensor blood glucose level, wear duration, low sensed glucose alarm occurrences, and high sensed glucose alarm occurrences), located on the right-hand side of the Dashboard 710, may be included as well. Any suitable statistics, greater or lesser than those illustrated in FIG. 7.1, may be provided according to embodiments of the present invention.

FIG. 7.2 illustrates an Episode Summary 720 of the patient information in the Dashboard 710 in FIG. 7.1 according to embodiments of the present invention. The Episode Summary 720 provides information regarding hypoglycemic and hyperglycemic episodes by preceding events, the most frequent events for each episode, and pie charts detailing the events ending in hypoglycemic and hyperglycemic events, respectively. The top bar graphs in the Episode Summary 720 in FIG. 7.2 show the frequency of episodes of hypoglycemia preceded by events such as, for example, making a manual bolus, making multiple manual boluses, nocturnal, hyperglycemia, and large basal rate increase; and for the frequency of episodes of hyperglycemia preceded by events such as delayed site change, overcorrection of a low sensor glucose reading, dawn phenomenon, and large basal rate decrease. Recommendations with respect to these most frequent events (which may include the percentage of total events) for both hypoglycemia and hyperglycemia are provided immediately below the bar graphs in the Episode Summary 720.

Pie charts may be provided to visually break down the number of hypoglycemic events and hyperglycemic events, respectively, that occurred based on the overall number of preceding events in total. Finally, the lower part of the Episode Summary 720 provides some Overall Observations regarding the patient's therapy and some recommendations to improving the therapy (e.g., not using the Bolus Wizard, infusion site misuse, sensor wear frequency, and meter reading frequency).

The features, functions, and embodiments described above may be implemented in the context of one or more software applications that generate reports, charts, and/or other information that can be reviewed and considered by a caregiver. In certain embodiments, the software applications generate screens formatted for display on an electronic display monitor, such as a computer monitor. In accordance with the techniques and methodologies presented above, the decision support software applications can be utilized to uncover important patient behaviors that might be associated with glycemic excursions.

The diagnostic application represents an intelligent analytical tool that can be used to improve glycemic control in insulin pump users by optimizing the insulin pump therapy parameters. The particular decision support algorithms provide feedback for behavior modification and improvement of insulin pump therapy as well as reduce the data fatigue associated with glucose and insulin infusion data. The decision support software may also include applications that analyze the insulin therapy parameters that enable the physician to fine tune certain settings of the insulin infusion device to improve the patient's glycemic outcome. Moreover, the software may be utilized to address event specific patient behavior modification by providing real time feedback to the users.

Diabetes management generates extensive amounts of data from monitoring of blood glucose, meals, activities, and insulin infusion information. Users of modern insulin infusion devices can upload their device and event data to an appropriate system, such as the CARELINK® network database. The database, which includes voluntary user uploads since 2004, contains an array of diabetes management related variables including continuous glucose sensor values, glucose meter readings, events markers, alarms, basal rates, bolus units and pump settings. Understanding the large array of data and determining the simple trends hidden within it can be difficult and time consuming A physician visit time is usually not enough to detect trends in the data; more time is spent detecting the patterns than discussing treatment. Developing automated tools to detect patterns in the historical data can help the physician observe the trends in the data with ease, spend less time on interpretation, and spend more time working on the solutions.

Evaluation of insulin therapy data reveals trends associated with the use of insulin pump settings that lead to successful glycemic outcomes. For example, an initial set of rules for insulin therapy parameters can be developed from insulin therapy data, e.g., basal rates, insulin sensitivity, carbohydrate-to-insulin ratio, carbohydrate counting, and insulin infusion time. These rules can be used to fine tune insulin dosing parameters for successful glycemic outcomes.

In addition to the insulin therapy optimization, glucose control can be improved by providing real time decision support feedback for the users, analyzing the user events in real time, and providing feedback for behavior modification. For real time user behavior modification, a mobile smart phone application can be developed. The phone application can log the user events including meals and exercises; receive diabetes data from a personal database; analyze trends associated with the events; and provide immediate feedback based on retrospective analysis of the glucose data associated with the events.

Accordingly, the decision support software presented here enables the user to analyze the diabetes data effectively and make guided therapy adjustments based on historical trends. Automating the process of detecting relevant glucose data patterns allows a physician to focus on providing the solution and makes it easier and faster to improve glycemic outcomes. As explained in more detail below, improvement in glycemic control can be achieved by optimizing insulin pump therapy and behavior modification associated with meals and therapy. Analysis of events leading to glycemic excursions can be used to provide feedback for behavior modification and prevent the excursion associated with the event going forward. Analysis of the glucose data associated with the bolus events and basal rates can be used to fine tune the insulin pump settings in order to achieve better a glucose outcome from the use of the insulin pump.

Users of insulin infusion devices can deliver insulin using a basal rate to support normal body activity, along with a number of boluses during the day to support meals and correct for hyperglycemia. As described above, an insulin infusion device may also include a bolus calculator feature that calculates bolus dosage amounts based on carbohydrate consumption and current glucose levels. Insulin therapy regimes associated with ideal glycemic outcomes were studied to compare the trends and provide feedback to users. Trends observed in overnight basal rates and bolus calculator values are summarized below.

An optimum basal rate setting for a user results in stable euglycemic glucose values. In accordance with one study, the trends in rate of change (ROC) of glucose during the night were analyzed in users with favorable glucose outcomes. This study revealed that such users have a mean absolute ROC of less than 0.5 mg/dL/min over a period of thirty minutes. Thus, a user detected to have an ROC of greater than 0.5 mg/dL/min at a consistent time over many days can benefit from increasing the basal rate before that time to correct the increase in the glucose values. Of course, the threshold ROC value may be adjusted as needed.

Bolus calculator estimates are influenced by a food component and a correction component. In certain implementations, the food component is defined as:

$$\text{Food Insulin} = \frac{Carbs}{Carb\ \text{Ratio}},$$

where the carb-to-insulin ratio is a user-specific setting that can be adjusted by the user. The correction component is defined as Correction Insulin−Active Insulin, wherein $$\text{Correction Insulin} = \frac{\text{Current } BG - \text{High } BG\ \text{Target}}{\text{Insulin Sensitivity}}.$$

The efficacy of the bolus calculator algorithms would be evaluated based on the distribution of sensor glucose at the insulin action time compared to either sensor glucose at bolus time (for food bolus) or Target BG (for correction bolus). Users with successful glucose outcome would be off the target at insulin action time. Users consistently deviating from the target could improve the glycemic outcome of the bolus by fine tuning the carbohydrate ratio and/or the inulin sensitivity setting based on the detected trends.

An extension of the techniques and technology presented here relates to a smart phone application to log user events, evaluate trends, and provide feedback to users to prevent excursions. Meals, carbohydrate intake, exercise, bolus size, and medication are some of the user behaviors associated with glucose control. Evaluating the trends associated with ideal glycemic control and providing feedback to the users can result in avoiding excursions and improving the glucose outcome. The mobile application reads the glucose data from a database (e.g., the CARELINK® database) or from the insulin infusion device itself. The user logs an event into the application to view the glucose patterns associated with the event. For example, if a user plans to eat pancakes for breakfast, the application would take that input from the user, and evaluate and present feedback on the glucose trend associated with the eating pancakes for breakfast.

The following sections of this disclosure relate to additional features, functions, and methodologies that may be implemented in the decision support software. At least some of the features presented below analyze patient glucose data to detect conditions that may be indicative of potentially correctable settings of the insulin infusion device. In response to the detection of such conditions, the software generates one or more recommendations for consideration by the patient, a caregiver, etc. The recommendations may include suggestions regarding how best to adjust one or more configurable settings of the insulin infusion device to prevent glycemic excursions and to achieve better glycemia. As set forth in more detail below, the decision support software may be suitably written and executed to: (1) monitor and recommend adjustments to the basal rate pattern of the user; (2) check and recommend adjustments to bolus calculator settings; and (3) process and render displays of glucose data in formats that are convenient and easy to interpret.

Referring again to FIG. 1, an electronic computing device 100 (e.g., a processor-based desktop, laptop, tablet, or handheld computer, a smart phone device, a specially configured medical device, or the like) can be utilized as the host platform that carries out the various decision support features and functionality described herein. The computing device 100 may include at least one processor device and at least one memory element associated with the processor device. The at least one memory element may be utilized to store processor-executable instructions that, when executed by the at least one processor device, perform the methods, functions, and processes described in more detail herein (such as the various methods of managing use of a patient's insulin infusion device). For example, and without limitation, the computing device 100 may include or cooperate with a tangible and non-transitory electronic storage medium that includes the processor-executable instructions, which in turn are responsible for carrying out the methods and processes described in detail herein.

The host computing device 100 is suitably configured to generate various reports, charts, graphs, display screens, and other output formats that convey information for consideration by a physician, the patient, a caregiver, or the like. Although not always required, the computing device 100 will typically generate a report that is suitably formatted for display on a display element coupled to or integrated into the computing device 100. Alternatively or additionally, the report may be generated as an electronic file that can be transmitted or otherwise communicated from the host computing device 100 to a destination device for rendering, display, presentation, playback, printing, etc. The particular format, configuration, arrangement of content, and other aspects of the various reports described here may vary from one system to another, may vary depending on user preferences, and may vary depending on the type of content being conveyed. Notably, the reports generated by the computing device 100 may include one or more recommendations or suggestions to adjust certain settings of the patient's insulin infusion device, to modify the patient's meal bolus timing, or the like.

Basal Pattern Management

The decision support software application described here preferably includes a feature that relates to the management of the patient's basal pattern. Although the techniques and methodologies described here can be applied to manage the basal pattern during any period of time (or continuously), in certain embodiments, the feature is particularly suitable for managing the patient's overnight basal pattern. The overnight basal pattern can be easier to manage due to the absence of meals.

Figure 8:
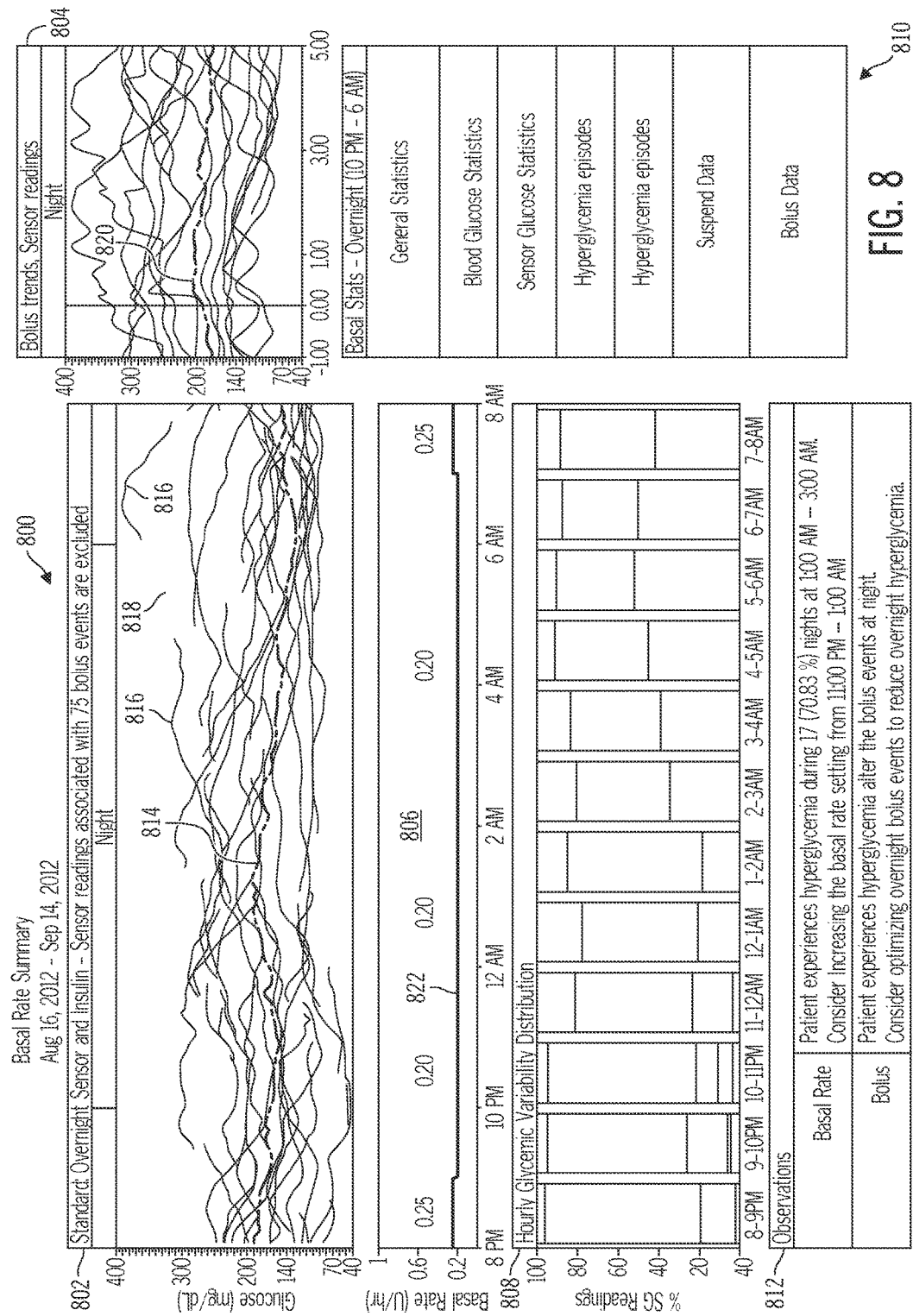
FIG. 8 illustrates a sample of a basal rate summary report, which may be generated in accordance with embodiments of the invention.

FIG. 8 depicts a sample of a basal rate summary report 800, which may be generated as an output display screen, a printed page, or in any desired format. The basal rate summary report 800 generally includes, without limitation: a sensor glucose region 802; a bolus trends region 804; a basal rate region 806; a glycemic variability distribution region 808; a basal statistics region 810; and an observations region 812. In some embodiments, all of these regions appear together on the basal rate summary report 800.

The sensor glucose region 802 includes a sensor glucose overlay report for the designated period (8:00 PM to 8:00 AM for this particular example). The sensor glucose overlay report contained in the sensor glucose region 802 is similar to the overlay report 200 described above with reference to FIG. 2A. Accordingly, the sensor glucose region 802 provides a visual representation of the received sensor glucose data for the user of the insulin infusion device, wherein the received sensor glucose data indicates blood glucose levels of the user for the designated period of time over a plurality of different days. Each individual plot represents the sensor glucose data for one period. In practice, the sensor glucose region 802 may visually convey the sensor glucose data for any number of days. In accordance with certain embodiments, however, recommendations are made based on the consideration of sensor glucose data collected for at least a minimum number of periods (e.g., at least five days) to ensure that the recommendations are based on actual observed trends rather than outlier data points.

The sensor glucose region 802 includes certain graphical elements that may assist in the interpretation of the data. For example, the sensor glucose region 802 includes a plot 814 (depicted as a dashed line) that represents the statistical average of the received sensor glucose data. Moreover, areas of the sensor glucose region 802 may be color-coded to indicate hyperglycemic excursions (e.g., yellow areas), hypoglycemic excursions (e.g., red areas), and/or glucose readings that are within range for the patient (e.g., gray or blue areas).

In certain situations, the sensor glucose region 802 will show "truncated" plots having some "missing" sensor glucose data. For example, the plot 816 in FIG. 8 has a discontinuity 818 that corresponds to removed sensor glucose data. This discontinuity 818 is a result of filtering that removes glucose data associated with a bolus delivery, temporary basal, or suspend event during the monitored period of time. As explained in more detail below, bolus events are disregarded for purposes of basal pattern analysis. For this particular example, the sensor glucose region 802 shows the sensor glucose data with 75 bolus events excluded.

The bolus trends region 804 includes a sensor glucose overlay report for at least some of the "removed" bolus event data. The bolus trends region 804 normalizes the bolus-related sensor glucose data relative to the time of bolus delivery (i.e., 0:00 time). The example shown in FIG. 8 shows an exemplary time window from one hour prior to bolus delivery (i.e., −1:00 time) to five hours after bolus delivery (i.e., 5:00 time). The actual time scale utilized by the bolus trends region 804 may be defined using any desired time window, and the range shown in FIG. 8 is not intended to be limiting or restricting in any way. The bolus trends region 804 may include a plot 820 that represents the average of the corresponding sensor glucose readings, and the bolus trends region 804 may be color-coded (as explained above for the sensor glucose region 802).

The basal rate region 806 includes a basal pattern plot 822 that indicates the basal rate (in Units/Hour) setting for the patient. In certain embodiments, the basal pattern plot 822 has a resolution that tracks the time resolution of the basal rate setting of the insulin infusion device. For example, if the insulin infusion device allows the user to designate a basal rate setting on an hour-by-hour basis, then the basal pattern plot 822 should accommodate hourly segments. As another example, if the patient's basal rate can be set in half-hour increments, then the basal pattern plot 822 should have a minimum resolution of 30 minutes. As explained in more detail below, the basal pattern management scheme provides suggestions related to the basal rate settings of the insulin infusion device. Thus, any portion of the basal pattern plot 822 could be subject to adjustment, at the time resolution supported by the insulin infusion device.

The glycemic variability distribution region 808 includes a graphical representation of the received sensor glucose data, broken down by certain time intervals. This example considers hourly intervals for the period of time, although other time intervals could be considered if so desired. The area corresponding to each hour is color-coded to indicate the percentage of the received sensor glucose readings that fall within certain designated categories, e.g., hyperglycemic, hypoglycemic, normal, or the like. Thus, the glycemic variability distribution region 808 allows a caregiver to quickly determine glycemic trends on an hour-by-hour basis, and across a plurality of different periods. The features and characteristics of the glycemic variability distribution region 808 are described in more detail below with reference to FIG. 33.

The basal statistics region 810 includes one or more fields for information related to the patient's basal pattern, glucose trends, bolus events, excursion events, and the like. Although not always required, the basal statistics region 810 may group the displayed information into various categories, such as (without limitation): General Statistics; Blood Glucose Statistics; Sensor Glucose Statistics; Hyperglycemia Episodes; Hyperglycemia Episodes; Suspend Data; and Bolus Data. The basal statistics region 810 may include any or all of the following information, data, or fields, without limitation: an active pattern designation; a maximum basal rate; an analysis duration; an average total basal dosage per night; an average blood glucose reading; a number, count, or percentage of glucose readings that are less than a low threshold value (e.g., 80 mg/dL); a number, count, or percentage of glucose readings that are greater than a high threshold value (e.g., 140 mg/dL); an average sensor glucose reading; an average hypoglycemia measurement; an average hyperglycemia measurement; statistics related to hyperglycemic episodes; statistics related to hypoglycemic episodes; suspend duration information; and bolus information. The number of fields, the amount of data included in the basal statistics region 810, the arrangement and formatting of the information, and/or other features and characteristics of the basal statistics region 810 may vary from that depicted in FIG. 8. Moreover, the fields and information shown in FIG. 8 are not intended to limit or otherwise restrict the scope or application of the subject matter described here.

The observations region 812 includes one or more fields that summarize the analyses and recommendations related to basal pattern management. For example, the observations region 812 may include a description of potentially troublesome events (hyperglycemia or hypoglycemia), detected glucose trends, bolus-related events, or the like. Moreover, the observations region 812 is utilized to provide recommendations that might be helpful to address one or more of the detected conditions. The recommendations that appear in the observations region 812 may include, without limitation: a recommendation to adjust (increase or decrease) the overnight basal rate setting of the insulin infusion device for one or more segments of time; a recommendation to adjust a bolus dosage for a meal bolus event; a recommendation to adjust a bolus dosage; a recommendation to adjust the timing of a bolus; or the like. The content of the observations region 812 may be considered to be an output of the decision support software, wherein the output can be reviewed and considered by a physician, the patient, or a caregiver for purposes of adjusting one or more settings of the insulin infusion device and/or for purposes of otherwise enhancing the insulin treatment plan.

Figure 9:
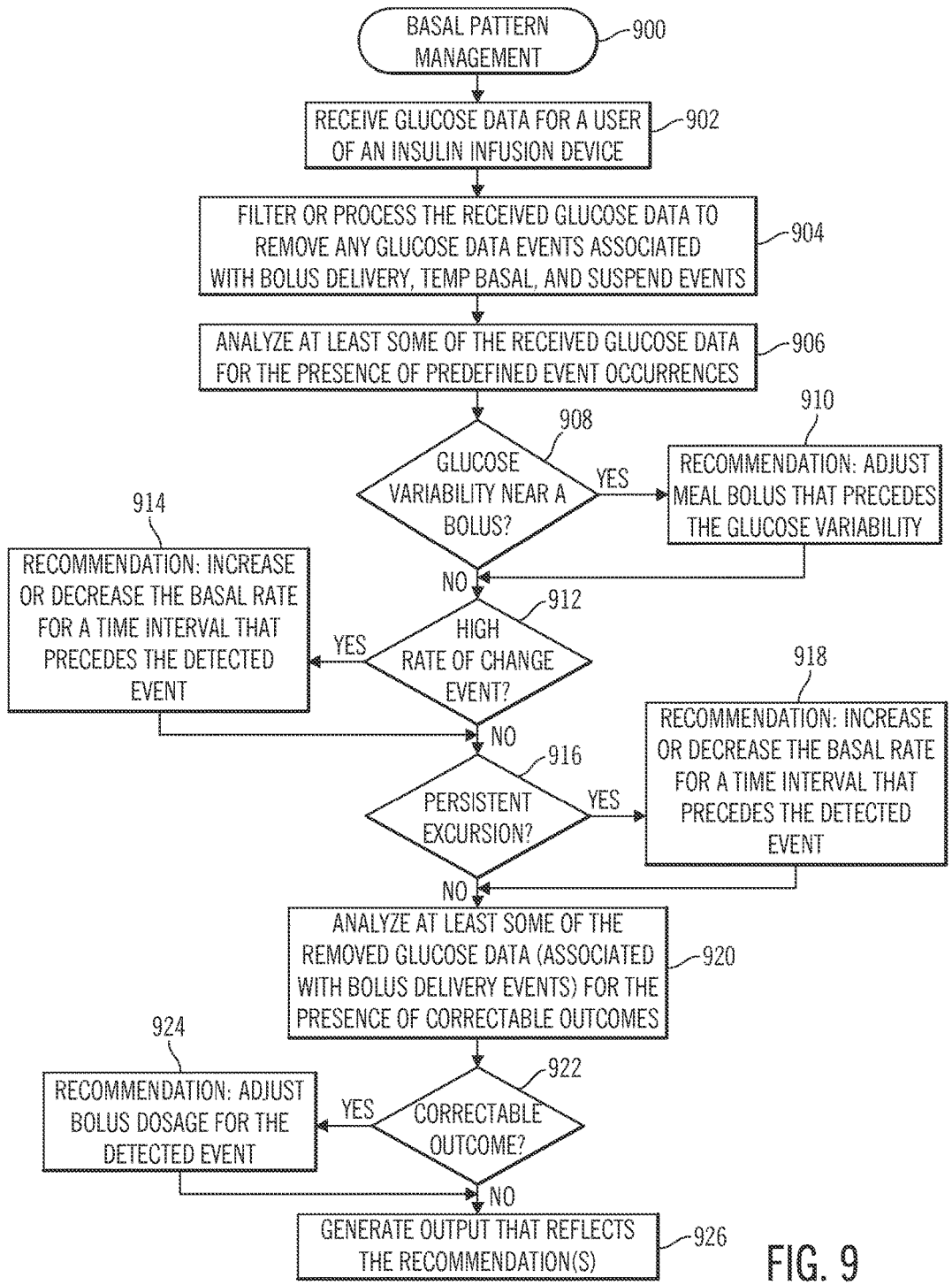
FIG. 9 is a flow chart that illustrates an embodiment of a basal pattern management process.

The output that appears in the observations region 812 varies from patient to patient, and from day to day. Moreover, the content of the observations region 812 could be provided at the request of the user and/or in accordance with certain user-specified preferences or settings. The observations and recommendations are generated and provided in response to the analysis and processing of the collected sensor glucose data. In this regard, FIG. 9 is a flow chart that illustrates an embodiment of a basal pattern management process 900, which may be performed by a computing device that executes the decision support software.

The illustrated embodiment of the process 900 receives glucose data for a user of the insulin infusion device (task 902). The glucose data may be sensor glucose (SG) data from a continuous glucose sensor, blood glucose (BG) data from a glucose meter, or another form of glucose information that indicates blood glucose levels of the user for a period of time during which the insulin infusion device is regulating delivery of insulin to the user. For the embodiment described here, the glucose data is SG data from a suitably configured glucose sensor, and the glucose data includes overnight data collected over a plurality of days (e.g., a month's worth of SG data). The SG data can be received or downloaded in real time or substantially real time, according to a designated data transfer schedule, on demand in a batch format, or the like.

The SG data received at task 902 may be considered to be unfiltered and unaltered original SG data, wherein such original SG data can be analyzed and processed as needed to support any of the features and functions described here. For example, the process 900 filters or otherwise processes the received SG data to remove any of the SG data that is associated with bolus delivery, temporary basal, and suspend events that occurred during the designated period of time (task 904). The filtered SG data can then be analyzed for trends that relate to the patient's basal rate without the presence of "noise" or interference that may otherwise be caused by bolus, temporary basal, and suspend events. Task 904 may be accomplished by searching the received SG data for flags, metadata, codes, or any type of identifier that marks a change from the basal rate infusion. For example, the received SG data may include time stamps that indicate the time corresponding to each bolus delivery event. The filtering at task 904 can then remove an appropriate "window" of the SG data surrounding the bolus event, based on the time stamp information. Referring back to FIG. 8, for example, each removed bolus event is defined from a time one hour before the delivery of the bolus to a time five hours after the delivery.

The SG data may also be filtered to remove data that may be indicative of an unregistered meal, a sensor artifact, a data transmission error, or the like. For example, the SG data may be filtered to remove data that indicates a SG rate of change that exceeds a threshold value (e.g., 2.0 mg/dL/min).

The process 900 continues by analyzing at least some of the remaining SG data for the presence of any of a plurality of event occurrences (task 906). At least some of the event occurrences are indicative of a correctable basal rate setting of the insulin infusion device, while other event occurrences are indicative of a correctable bolus dosage. Task 906 may leverage empirical data, the results of clinical studies, and/or historical data to detect certain detectable patterns, trends, or characteristics of the SG data. In practice, therefore, the decision support software can be written such that task 906 compares the SG data against any number of predefined conditions, which in turn correspond to a suboptimal, suspicious, or potentially troublesome basal pattern. Although the process 900 and the decision support software may check for the presence of any number of conditions, a number of non-limiting examples are provided here for ease of understanding.

In accordance with some embodiments, the process 900 checks for a high glucose variability event occurring at a time that is close to a bolus (query task 908). "Close to a bolus" or "near a bolus" in this context may refer to any designated period of time relative to the preceding bolus, such as the first five to six hours. Query task 908 analyzes the SG data in this time frame to determine how much the SG readings vary from one day to the next. For example, if ten days are under analysis and the SG data indicates early overnight hyperglycemia for five days and early overnight hypoglycemia for the other five days, then the process 900 might indicate that the basal rate cannot be accurately controlled to compensate for the variability. As another example, if the patient is consistently hypoglycemic two hours after the overnight time period begins, then the process 900 will recommend an adjustment to the patient's dinner bolus in an attempt at improving the overnight basal rate pattern.

The specific methodology that forms the basis of the determination made at query task 908 may vary from one implementation to another. In accordance with some embodiments, the SG data in the first two hours of the overnight period is analyzed to obtain a value corresponding to the 75th percentile and a value corresponding to the 25th percentile. The difference between these two percentile values is then compared to a predetermined threshold (e.g., 60 mg/dL); high variability is indicated when the difference exceeds this threshold.

For purposes of this description, and regardless of the context or goal of the particular analysis, the processing of the SG data may be handled in any suitable way to check for the presence of certain predefined event occurrences. In some situations it may be appropriate and convenient to simply analyze the characteristics of an average SG plot, a median SG plot, or the like. In other situations, determinations can be made based on a statistical review of the individual SG plots. For example, the determination could be based on whether the relevant decision criteria is satisfied for a simple majority of SG plots (e.g., hyperglycemia occurs in more than 50% of the SG plots during a stated period of time over 28 days). As another example, the standard deviation may be considered for purposes of analyzing the SG data. Alternatively, the determination could be based on whether the relevant decision criteria is satisfied for at least a threshold number of the SG plots (e.g., hyperglycemia must occur in more than 75% of the SG plots). In certain situations, it may be desirable to discard some "boundary" SG plots such that decisions are not based on outlier data. These and/or other number of data processing techniques could be utilized in the context of basal pattern management process 900, the bolus calculator settings management process 1200 (FIG. 17), and other processes described here.

Figure 10:
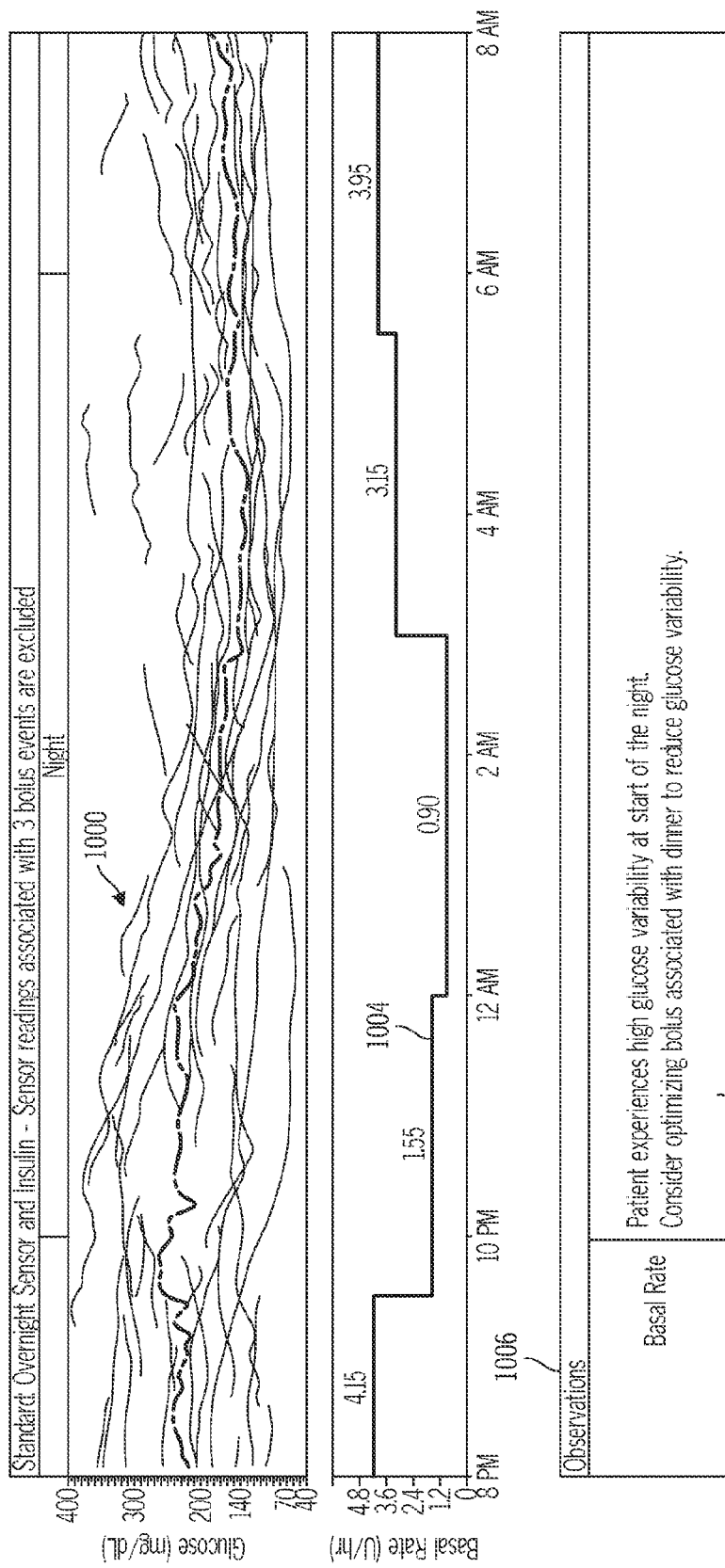
FIG. 10 depicts glucose data and a corresponding recommendation related to a high glucose variability event.

FIG. 10 depicts overnight glucose data 1000 and a corresponding recommendation 1002 related to a high glucose variability event. FIG. 10 shows how the glucose data 1000 between 8:00 PM and 10:00 PM exhibits high variability and "spread" along the vertical axis, even though the patient's basal rate pattern 1004 changes during the early two-hour period. For this particular example, the amount of early variability exceeds the designated threshold and, therefore, the decision support software detects this condition as an event occurrence for purposes of outputting an associated recommendation 1002. The observations region 1006 depicted in FIG. 10 includes a description of the detected event occurrence, along with the associated recommendation: "Patient experiences high glucose variability at start of the night. Consider optimizing bolus associated with dinner to reduce glucose variability."

Referring again to FIG. 9, if the process 900 detects high glucose variability occurring near a bolus (the "Yes" branch of query task 908), then a task 910 is performed to generate and output a recommendation that includes a suggestion to adjust the bolus dosage for a meal bolus (typically a dinner bolus) that precedes the glucose variability (task 910). The recommendation may also specify whether it is advisable to increase or decrease the meal bolus. In some embodiments, the recommendation may also suggest an amount by which to adjust the meal bolus.

Whether or not early glucose variability is detected at query task 908, the process also checks the SG data for the presence of a high rate of change event (query task 912). Query task 912 may check for a negative rate of change trend that corresponds to an uncorrected decrease in blood glucose level, and/or for a positive rate of change trend that corresponds to an uncorrected increase in blood glucose level. Alternatively or additionally, query task 912 may check for a large increase/decrease in the SG readings over a predefined window of time, such as two hours. It should be appreciated that the decision support software can utilize any desired formula or algorithm to define "high rate of change" or "large SG increase" or "large SG decrease" for purposes of the determination made at query task 912. Moreover, the specific methodology that forms the basis of the determination made at query task 912 may vary from one implementation to another.

Figure 11:
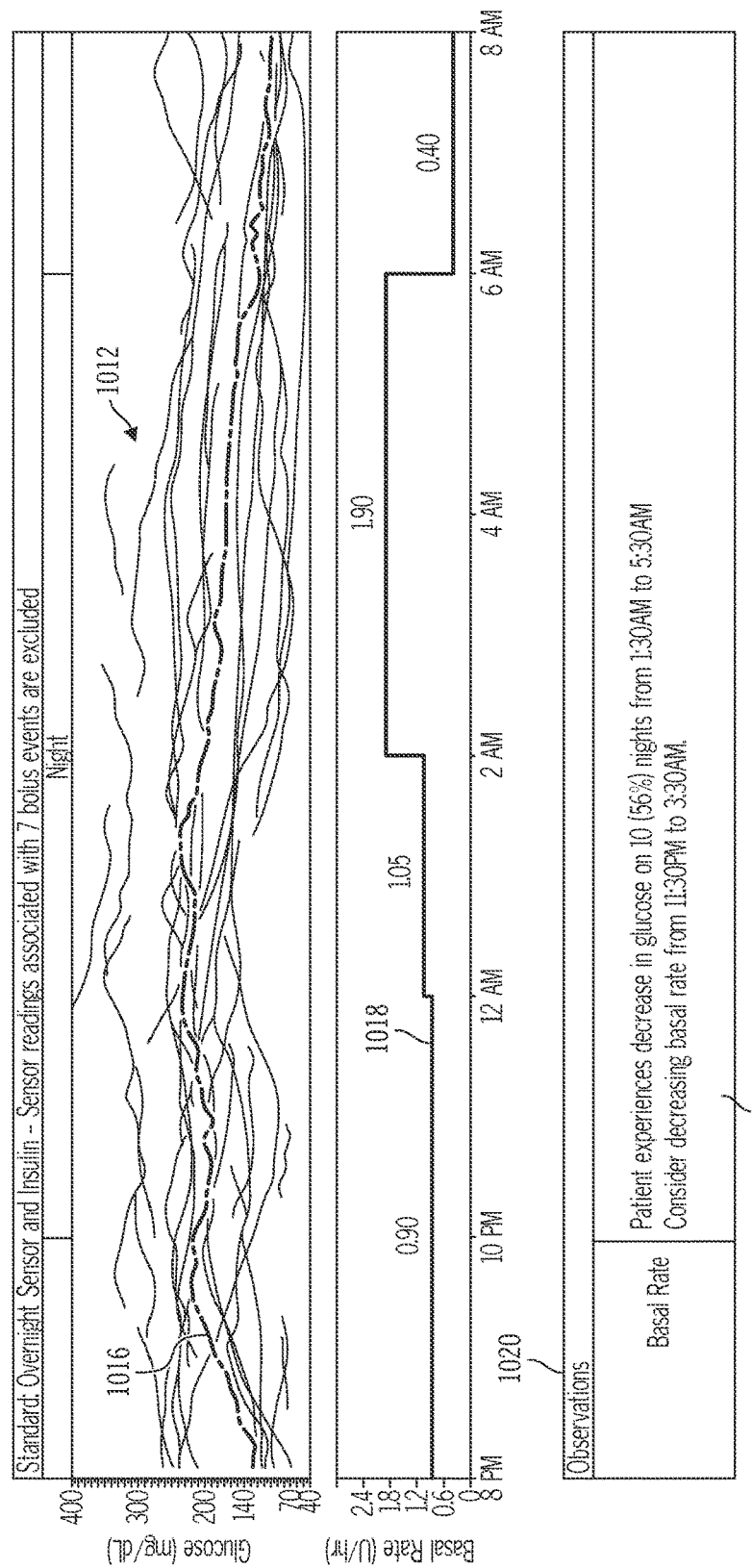
FIG. 11 depicts glucose data and a corresponding recommendation related to a decreasing glucose event.

FIG. 11 depicts overnight glucose data 1012 and a corresponding recommendation 1014 related to a decreasing glucose event. The average plot 1016 of the overnight glucose data 1012 visually indicates how the overnight glucose data 1012 between about 1:30 AM and about 5:30 AM exhibits a relatively high negative rate of change, even though the patient's basal rate pattern 1018 changes during the period. For this particular example, the amount of negative rate of change and plurality of events with negative rate of change exceeds a designated threshold and, therefore, the decision support software detects this condition as a triggering event occurrence for purposes of outputting the recommendation 1014. The observations region 1020 depicted in FIG. 11 includes a description of the detected event occurrence, along with the associated recommendation: "Patient experiences decrease in glucose on 10 (56%) nights from 1:30 AM to 5:30 AM. Consider decreasing basal rate from 11:30 PM to 3:30 AM."

Figure 12:
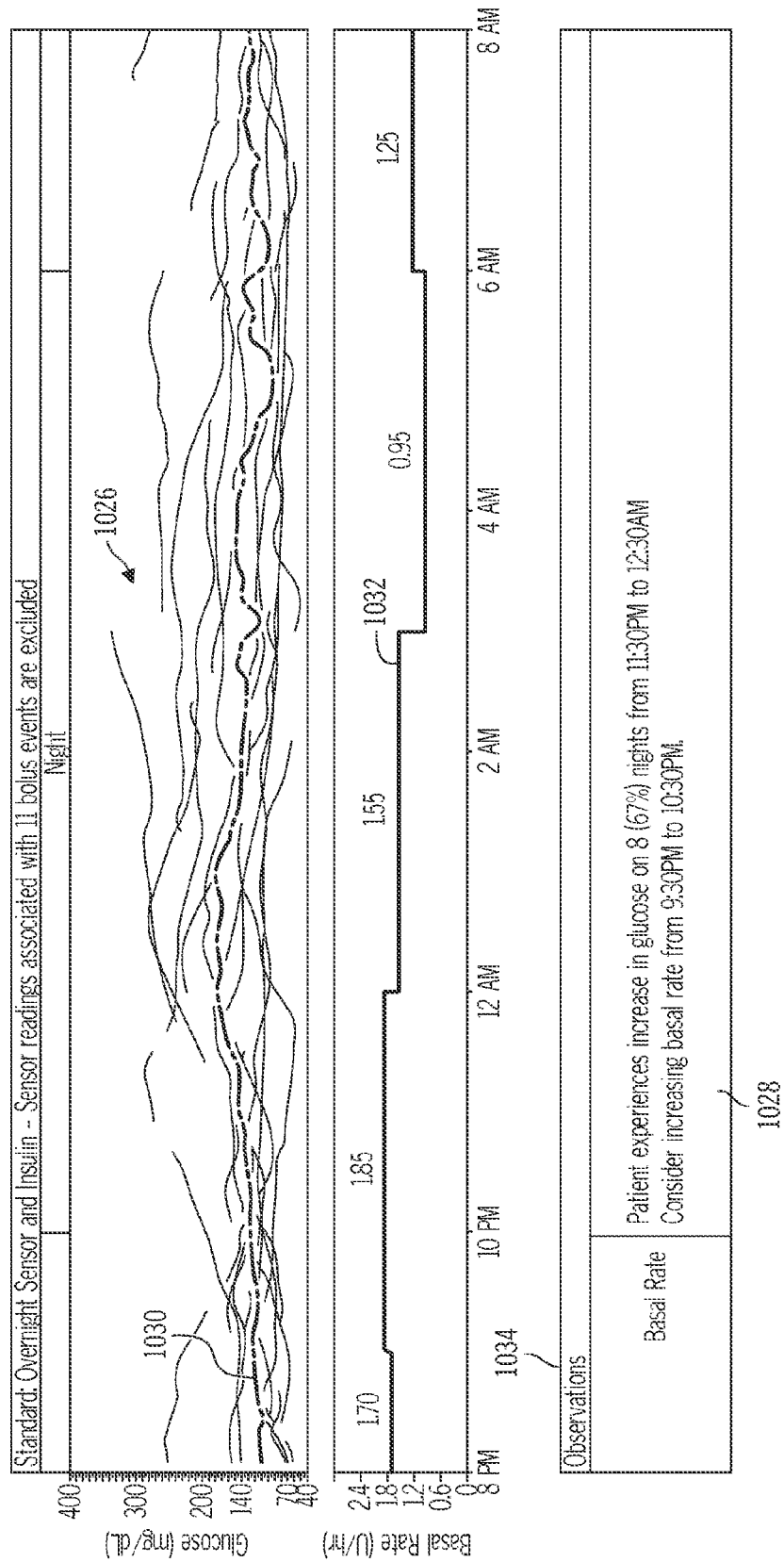
FIG. 12 depicts glucose data and a corresponding recommendation related to an increasing glucose event.

FIG. 12 depicts overnight glucose data 1026 and a corresponding recommendation 1028 related to an increasing glucose event. The average plot 1030 of the overnight glucose data 1026 visually indicates how the glucose data 1026 between about 11:30 PM and about 12:30 AM exhibits a relatively high positive rate of change, even though the patient's basal rate pattern 1032 changes during the overnight period. For this particular example, the amount of positive rate of change and plurality of events with positive rate of change during this period exceeds a designated threshold and, therefore, the decision support software detects this condition as a triggering event occurrence for purposes of outputting the recommendation 1028. The observations region 1034 depicted in FIG. 12 includes a description of the detected event occurrence, along with the associated recommendation: "Patient experiences increase in glucose on 8 (67%) nights from 11:30 PM to 12:30 AM. Consider increasing basal rate from 9:30 PM to 10:30 PM."

Referring back to FIG. 9, if the process 900 detects a high negative rate of change for a window of time within the period (the "Yes" branch of query task 912), then a task 914 is performed to generate and output a recommendation that includes a suggestion to decrease the basal rate setting of the patient for a time interval starting before the detected time interval (the window of time) of the rate of change event. Conversely, if the process 900 detects a high positive rate of change for a window of time within the period (the "Yes" branch of query task 912), then task 914 is performed to generate and output a recommendation that includes a suggestion to increase the basal rate setting of the patient for a time interval starting before the detected time interval (the window of time) of the rate of change event. The recommendation provided at task 914 may also suggest an amount to increase or decrease the basal rate for the given time segment(s), or suggest a range of adjustment values for consideration. For example, the recommendation may suggest a relatively low increase/decrease in the basal rate for one half-hour segment of the overall overnight basal pattern, a relatively moderate increase/decrease in the basal rate for the next three half-hour segments, and a relatively high increase/decrease in the basal rate for the last two half-hour segments.

Whether or not a high rate of change event occurrence is detected at query task 912, the process also checks the SG data for the presence of an uncorrected persistent excursion event (query task 916). Query task 916 may check for a consistent hypoglycemic period or a consistent hyperglycemic period that occurs during or throughout the overnight period of time. It should be appreciated that the decision support software can utilize any desired formula or algorithm to define "persistent hyperglycemia" or "persistent hypoglycemia" for purposes of the determination made at query task 916. For example, the determination could be made based on an average of the SG data, or the determination could be made based on whether or not the majority of the SG data indicates a hyperglycemic or a hypoglycemic trend over a threshold length of time during the overnight period. Moreover, the specific methodology that forms the basis of the determination made at query task 916 may vary from one implementation to another.

Figure 13:
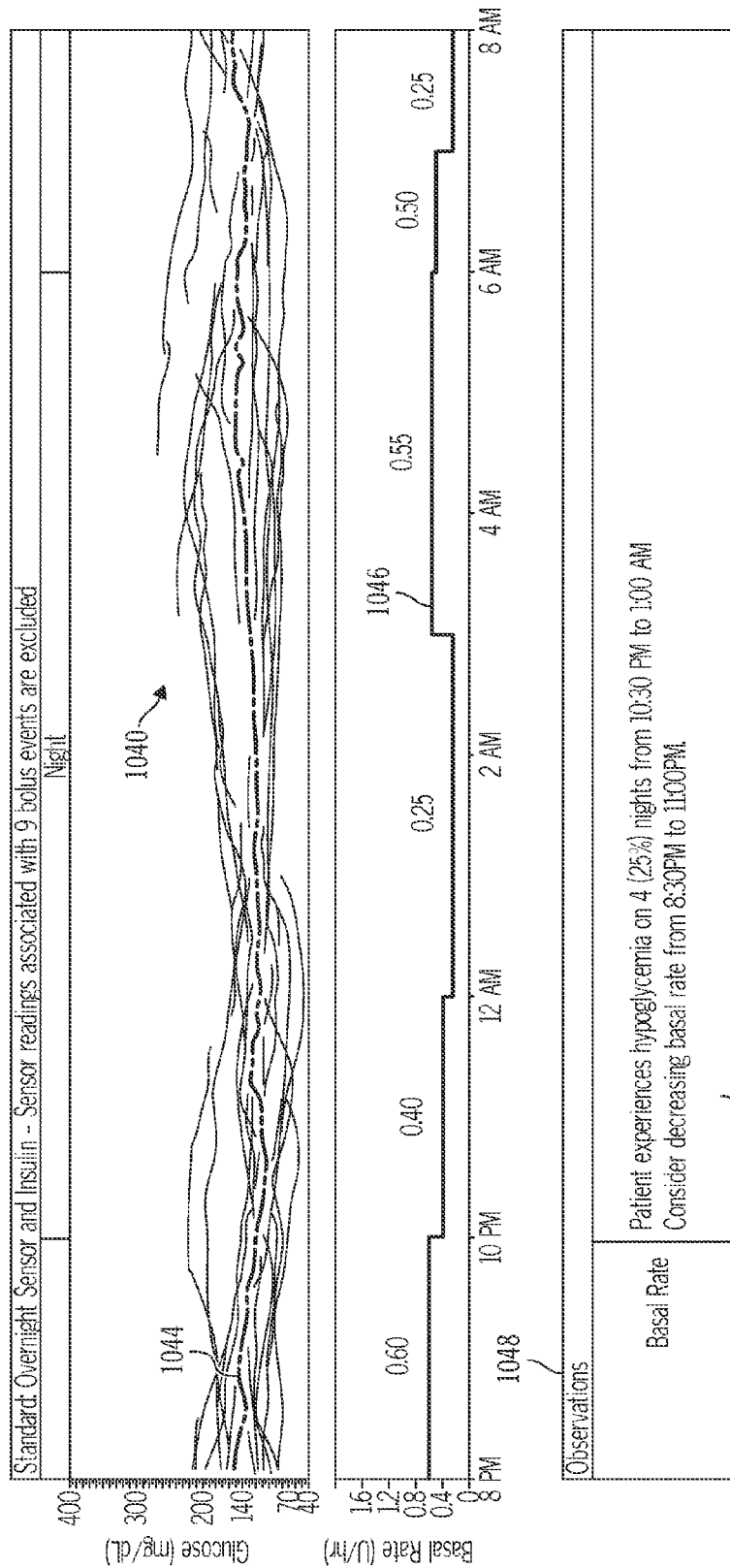
FIG. 13 depicts glucose data and a corresponding recommendation related to a persistent hypoglycemic event.

FIG. 13 depicts glucose data 1040 and a corresponding recommendation 1042 related to a persistent hypoglycemic event. Note that even though the average plot 1044 of the overnight glucose data 1040 appears to be relatively stable, there are several individual occurrences of hypoglycemia between about 10:30 PM and about 1:00 AM. These hypoglycemic excursions occur even though the patient's basal rate pattern 1046 changes during the period. For this particular example, at least a minimum number of SG plots exhibit hypoglycemic excursions within the same period of time (10:30 PM to 1:00 AM). Accordingly, the decision support software detects this condition as a triggering event occurrence for purposes of outputting the recommendation 1042. The observations region 1048 depicted in FIG. 13 includes a description of the detected event occurrence, along with the associated recommendation: "Patient experiences hypoglycemia on 4 (25%) nights from 10:30 PM to 1:00 AM. Consider decreasing basal rate from 8:30 PM to 11:00 PM."

Figure 14:
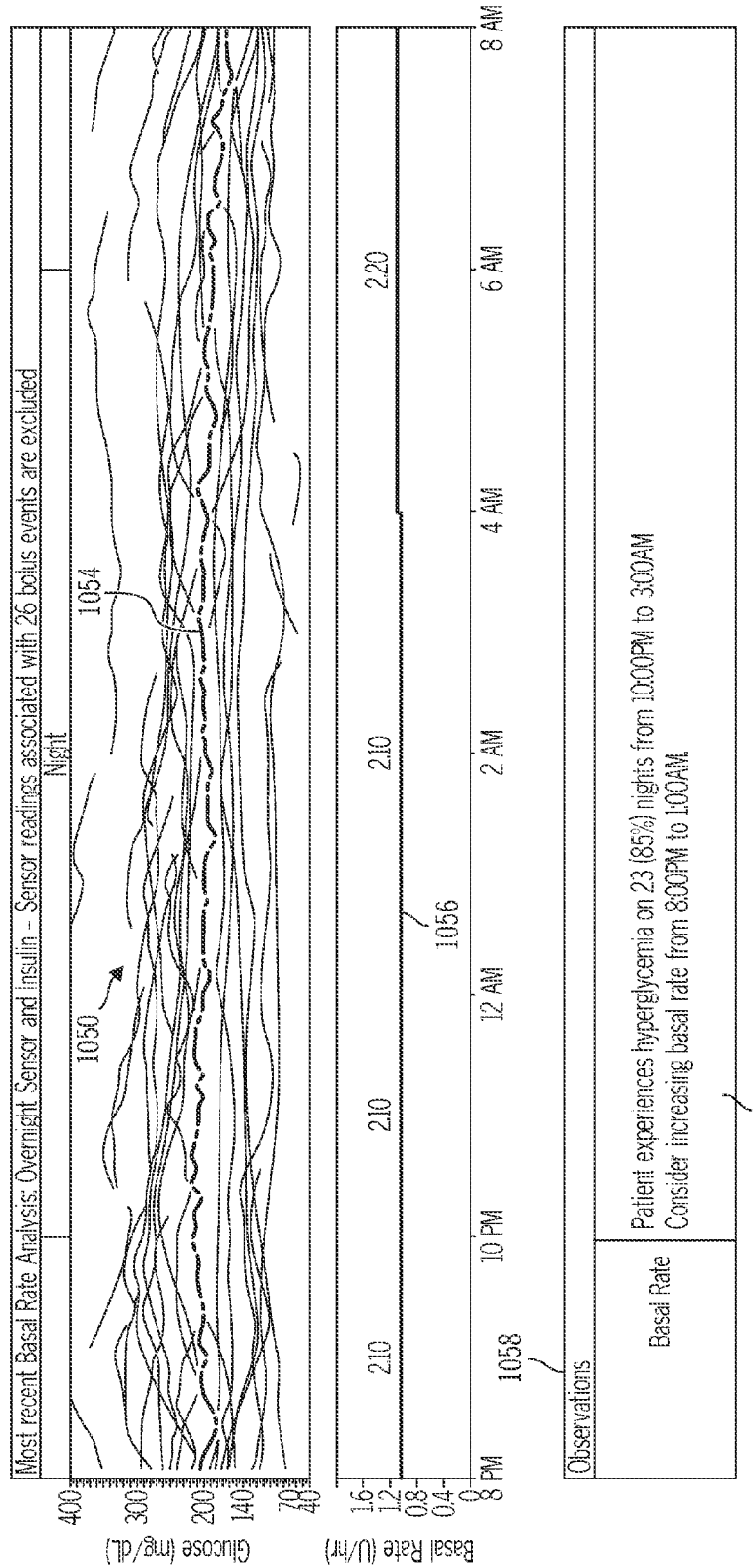
FIG. 14 depicts glucose data and a corresponding recommendation related to a persistent hyperglycemic event.

FIG. 14 depicts glucose data 1050 and a corresponding recommendation 1052 related to a persistent hyperglycemic event. The average plot 1054 of the glucose data 1050 visually indicates how the glucose data 1050 on average remains in the hyperglycemic range throughout the overnight period, even though the patient's basal rate pattern 1056 changes during the overnight period. Note that the majority of individual SG data plots indicate hyperglycemia between about 10:00 PM and about 3:00 AM. For this particular example, at least a minimum number of SG plots exhibit hyperglycemic excursions within the same period of time (10:00 PM to 3:00 AM). Accordingly, the decision support software detects this condition as a triggering event occurrence for purposes of outputting the recommendation 1052. The observations region 1058 depicted in FIG. 14 includes a description of the detected event occurrence, along with the associated recommendation: "Patient experiences hyperglycemia on 23 (85%) nights from 10:00 PM to 3:00 AM. Consider increasing basal rate from 8:00 PM to 1:00 AM."

Referring back to FIG. 9, if the process 900 detects an uncorrected persistent hypoglycemic event during the period of time (the "Yes" branch of query task 916), then a task 918 is performed to generate and output a recommendation that includes a suggestion to decrease the basal rate setting of the patient for a time interval (one or more defined segments of time) starting before the detected time interval (the window of time) of the persistent hypoglycemic event. Conversely, if the process 900 detects an uncorrected persistent hyperglycemic event during the period of time (the "Yes" branch of query task 916), then task 918 is performed to generate and output a recommendation that includes a suggestion to increase the basal rate setting of the patient for a time interval that starts before the detected time interval (the window of time) of the persistent hyperglycemic event. The recommendation provided at task 918 may also suggest an amount to increase or decrease the basal rate for the given time segment(s), or suggest a range of adjustment values for consideration.

As mentioned above with reference to the bolus trends region 804 (FIG. 8) and with reference to task 904, the received SG data is filtered to separate data that is associated with bolus delivery events during the period of time. In accordance with some embodiments, at least some of the removed glucose data that is associated with bolus delivery events (i.e., bolus event data) is processed and analyzed for the presence of correctable bolus outcomes (task 920). For example, the bolus event data may be checked for hypoglycemia or hyperglycemia following a nighttime bolus, and/or the bolus event data may be checked for other anomalies, suspicious trends, or other characteristics that might be indicative of a correctable bolus outcome. Thus, if the process 900 detects the presence of a potentially correctable outcome for a bolus delivery event (the "Yes" branch of query task 922), then a task 924 is performed to generate and output a bolus recommendation that includes a suggestion to adjust the bolus dosage corresponding to the respective bolus delivery event. The recommendation may also specify whether it is advisable to increase or decrease the overnight bolus dosage. In some embodiments, the recommendation may also suggest an amount by which to adjust the bolus.

The methodology outlined above can be utilized to detect one or more event occurrences, which in turn may influence the content of a recommendation (or multiple recommendations) presented to the user of the decision support software. Regardless of which event occurrences, if any, are detected, the process 900 may continue by generating an output that includes, conveys, or otherwise reflects the recommendations (task 926). In this regard, the recommendations are influenced by, and are associated with, the detected event occurrences. The output may be a report (see FIG. 8) suitable for display, printing, and/or transmission to a destination device, wherein the recommendations included on the report are intended to address the detected event occurrences. In certain embodiments, the process 900 generates and sends one or more commands to initiate the adjustment of the basal rate setting of the insulin infusion device in accordance with the recommendations. In other words, the process 900 may allow a caregiver to review and consider a recommended adjustment approach and then actually initiate an adjustment to be automatically carried out at the insulin infusion device.

It should be appreciated that the process 900 could be designed to monitor for any number of different predefined event occurrences, and that the particular detection algorithms, formulas, and relationships may vary from one embodiment to another. To summarize, some or all of the following event occurrences and conditions may be monitored: hypoglycemia or hyperglycemia observed during a majority of nights; a large difference between the upper and lower quartile ranges of the glucose levels; a high negative rate of change in glucose levels; a large decrease in glucose level over a short period of time (e.g., two hours); a high positive rate of change in glucose levels; a large increase in glucose level over a short period of time (e.g., two hours); hypoglycemia observed during some overnight periods (and where severe hyperglycemia is not detected during any overnight period); hyperglycemia observed during a majority of the overnight periods (and where hypoglycemia is not detected during any overnight period); hypoglycemia observed after bolus events at night; hyperglycemia observed after a majority of bolus events at night.

Moreover, different detection criteria could be used for different time slots during the period of time of interest. For example, checking for high glucose variability near the beginning of the overnight period may be based on one methodology, while checking for high glucose variability near the end of the overnight period may be based on another methodology. These and other variations are contemplated by this disclosure.

Bolus Calculator Management

The decision support software described here also includes a feature that relates to the management of the patient's bolus calculator settings. As mentioned above, the insulin infusion device may include a bolus calculator that functions to estimate and calculate a bolus dosage recommendation in accordance with the following relationships:

$$\text{Total Bolus} = \text{Food Insulin} + (\text{Correction Insulin} - \text{Active Insulin}) \quad \text{(Eq. 1)}$$

$$\text{Food Insulin} = \frac{Carbs}{Carb \text{ Ratio}} \quad \text{(Eq. 2)}$$

$$\text{Correction Insulin} = \frac{\text{Current } BG - \text{High } BG \text{ Target}}{\text{Insulin Sensitivity}} \quad \text{(Eq. 3)}$$

Here, Carbs refers to a user-entered carbohydrate consumption value, which is dictated by the amount and type of food to be eaten. The Current BG is a user-entered blood glucose value, which is typically obtained using a blood glucose meter, such as a finger stick device. The Carb Ratio value is a user-specific adjustable bolus calculator setting, expressed in grams of carbohydrates per unit of insulin (g/U). The Insulin Sensitivity value is another user-specific adjustable bolus calculator setting, expressed in the concentration of glucose per unit of insulin (mg/dL/U). Accordingly, the bolus calculator output may be influenced by a food component and/or a correction component. Inspection of the above relationships reveals that an analysis of bolus calculator events having only the food component can be useful for purposes of adjusting the carbohydrate ratio setting. Conversely, an analysis of bolus calculator events having only the correction component can be useful for purposes of adjusting the insulin sensitivity setting. Adjustment of these bolus calculator settings is desirable to improve the accuracy of the bolus estimations and to prevent glucose excursions that may be associated with miscalculated boluses.

Figure 15A:
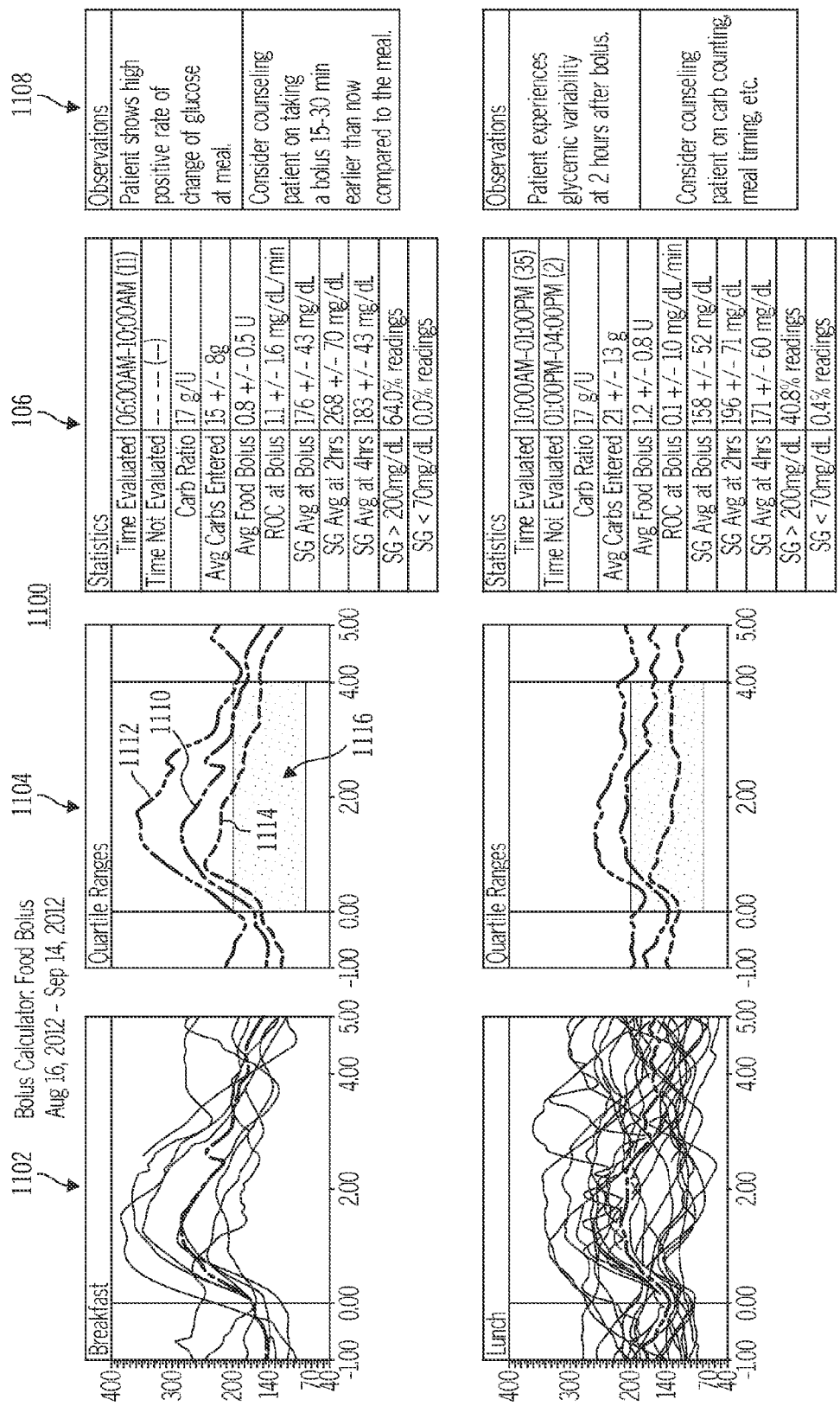
FIGS. 15A and 15B illustrate a sample of a bolus calculator summary report for food bolus events, which may be generated in accordance with embodiments of the invention.
Figure 15B:
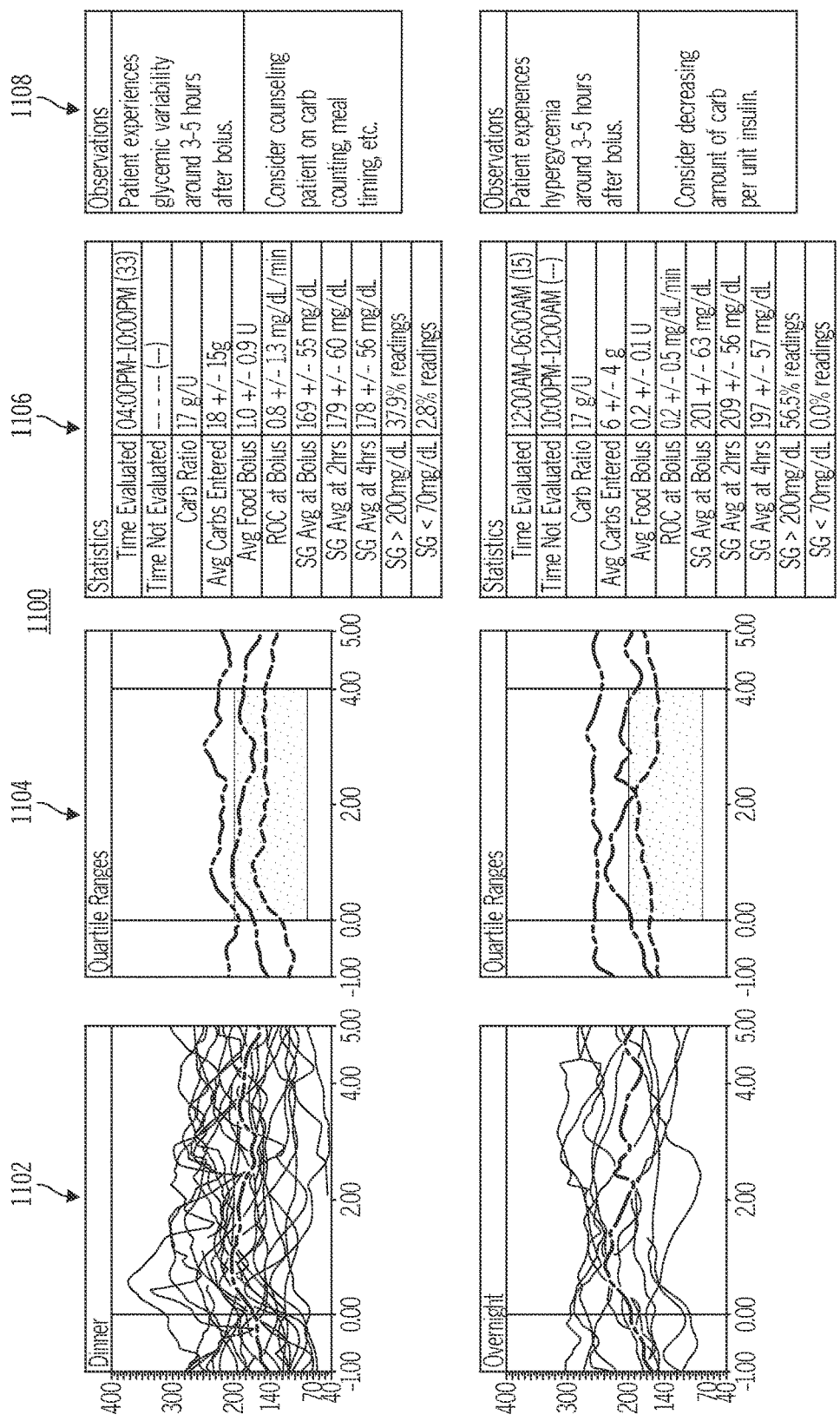

FIG. 15 illustrates a sample of a bolus calculator summary report 1100 for food bolus events, which may be generated as an output display screen, a printed page, or in any desired format. Due to space limitations, FIG. 15 spans two drawing sheets; the top portion of the report 1100 appears as FIG. 15A, and the bottom portion of the report appears as FIG. 15B. In certain embodiments, the bolus calculator summary report 1100 summarizes information that relates to a subset of bolus calculator events. More specifically, the bolus calculator summary report 1100 summarizes bolus calculator events where it is assumed that each calculated bolus dosage only contains a food component (and a minimal, if any, correction component).

The bolus calculator summary report 1100 shown in FIG. 15 includes four entries (depicted in a horizontal arrangement), although the decision support software may provide for any number of entries, which may span any number of screens or pages. The four entries correspond to breakfast, lunch, and dinner meals, and one overnight food bolus event. Other entries could be generated to track other meals, snacks, etc. Each entry of the bolus calculator summary report 1100 generally includes, without limitation: a glucose data region 1102; a quartile ranges region 1104; a statistics region 1106; and an observations region 1108. In some embodiments, all of these regions appear together on the bolus calculator summary report 1100.

Each glucose data region 1102 includes a sensor glucose overlay report for the respective food bolus event. The glucose data regions 1102 share certain characteristics and display characteristics with the bolus trends region 804 described above with reference to FIG. 8. In this regard, the overlay data depicted in each glucose data region 1102 is normalized relative to the time of bolus delivery (i.e., 0:00 time), and along a horizontal scale that spans one hour before 0:00 time and five hours after 0:00 time, although any desired time range could be used. Each glucose data region 1102 also includes an average plot (shown in dashed lines) that represents the average of the corresponding sensor glucose readings. Moreover, the glucose data regions 1102 may be color-coded (as explained above for the sensor glucose region 802).

Each quartile ranges region 1104 includes at least three plots: a median plot 1110; a 75th percentile plot 1112; and a 25th percentile plot 1114 (as indicated for the breakfast bolus entry at the top of FIG. 15). These plots may be color-coded or otherwise generated using visually distinguishable characteristics to make them easy to detect and distinguish from one another. The 75th percentile plot 1112 may represent an actual SG data plot taken from the received SG data (where the plot is at or near the 75th percentile relative to the other plots under consideration), or it may represent a plot that is calculated from the received SG data as the actual 75th percentile. Similarly, the 25th percentile plot 1114 may represent an actual SG data plot taken from the received SG data (where the plot is at or near the 25th percentile relative to the other plots under consideration), or it may represent a plot that is calculated from the received SG data as the actual 25th percentile. Although not always required, each quartile ranges region 1104 may include a visually distinguishable target zone 1116 that corresponds to the patient's target glucose zone for the graphically displayed time period.

Each statistics region 1106 includes one or more fields for information related to the respective food bolus. Each statistics region 1106 may include any or all of the following information, data, or fields, without limitation: a time evaluated period; a time not evaluated period; a carbohydrate ratio value; a carbs entered value; an average food bolus value; a glucose rate of change value for the time of the bolus; an average SG value for the time of the bolus; an average SG value at two hours after the bolus; an average SG value at four hours after the bolus; a number, count, or percentage of SG readings that are greater than a high threshold value (e.g., 200 mg/dL); and a number, count, or percentage of SG readings that are less than a low threshold value (e.g., 70 mg/dL). The number of fields, the amount of data included in the statistics region 1106, the arrangement and formatting of the information, and/or other features and characteristic of the statistics region 1106 may vary from that depicted in FIG. 15. Moreover, the fields and information shown in FIG. 15 are not intended to limit or otherwise restrict the scope or application of the subject matter described here.

The observations region 1108 for each bolus entry includes one or more fields that summarize the analyses and recommendations related to bolus calculator management. For example, the observations region 1108 may include a description of potentially troublesome events (hyperglycemia or hypoglycemia), detected glucose trends, or the like. Moreover, each observations region 1108 is utilized to provide recommendations that might be helpful to address one or more of the detected conditions. The recommendations that appear in the observations regions 1108 may include, without limitation: a recommendation to adjust (increase or decrease) the carbohydrate ratio setting for the patient; a recommendation to adjust a bolus dosage for a meal bolus event; a recommendation to adjust the timing of a bolus; a recommendation to counsel the patient regarding carbohydrate counting, meal timing, and/or other dietary habits; or the like. The content of each observations region 1108 may be considered to be an output of the decision support software, wherein the output can be reviewed and considered by a physician, the patient, or a caregiver for purposes of adjusting one or more settings of the insulin infusion device (in particular, the bolus calculator settings) and/or for purposes of otherwise enhancing the insulin treatment plan.

Figure 16A:
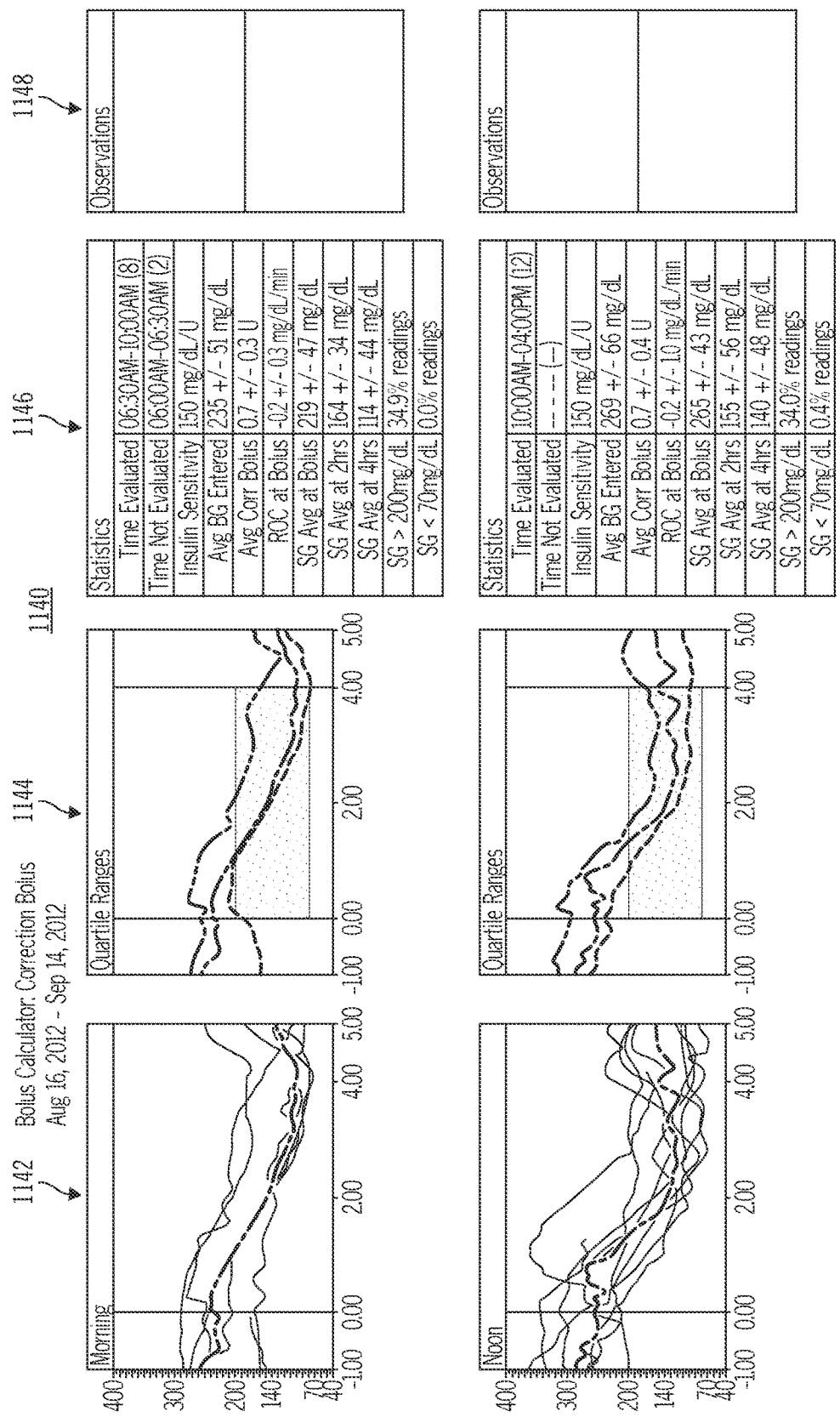
FIGS. 16A and 16B illustrate a sample of a bolus calculator summary report for correction bolus events, which may be generated in accordance with embodiments of the invention.
Figure 16B:
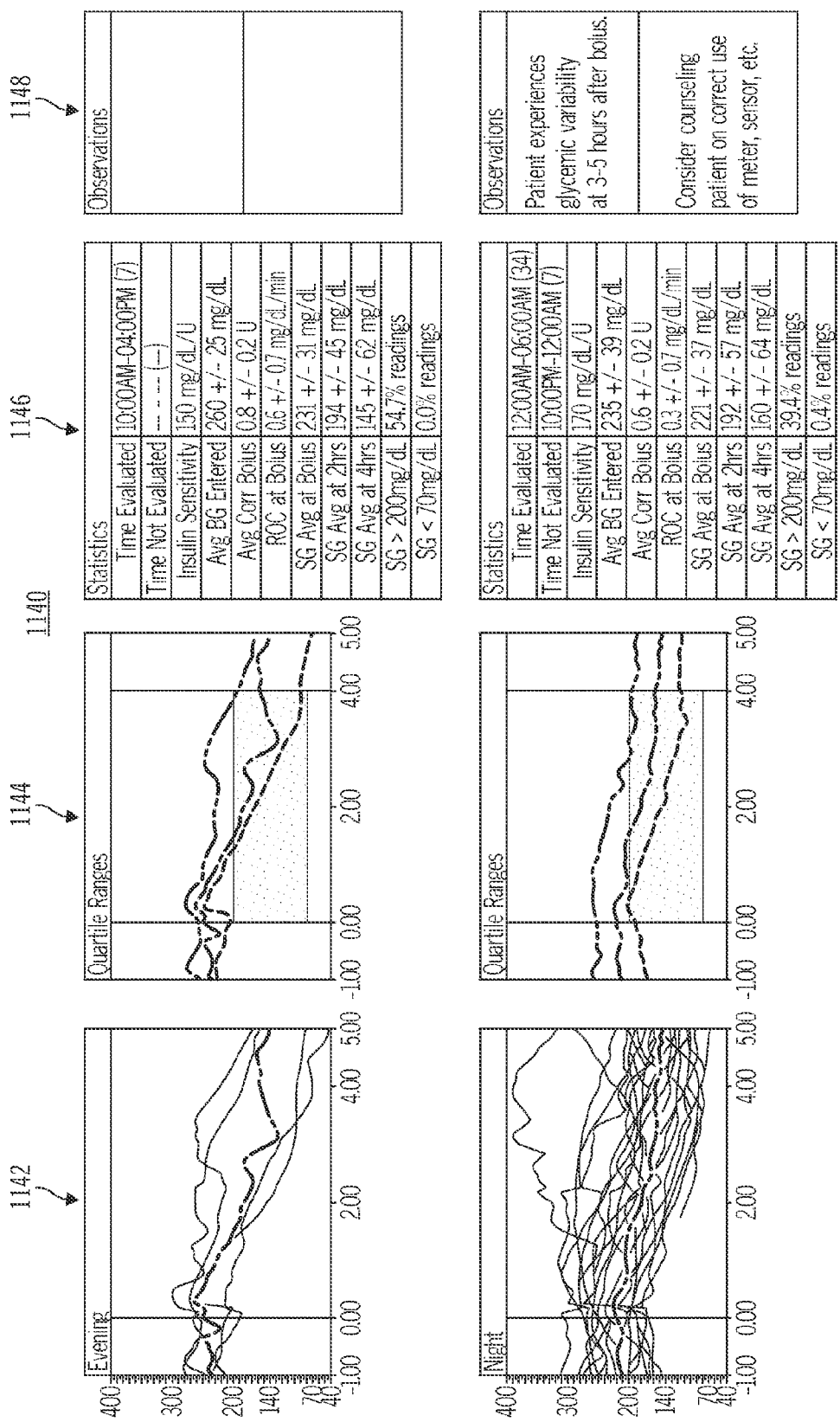

FIG. 16 illustrates a sample of a bolus calculator summary report 1140 for correction bolus events, which may be generated as an output display screen, a printed page, or in any desired format. Due to space limitations, FIG. 16 spans two drawing sheets; the top portion of the report 1140 appears as FIG. 16A, and the bottom portion of the report 1140 appears as FIG. 16B. In certain embodiments, the bolus calculator summary report 1140 summarizes information that relates to a subset of bolus calculator events. More specifically, the bolus calculator summary report 1140 summarizes bolus calculator events where it is assumed that each calculated bolus dosage only contains a correction component (and a minimal, if any, food component).

The bolus calculator summary report 1140 may include any number of entries (depicted in a horizontal arrangement), which may span any number of screens or pages. The four entries correspond to morning, noon, evening, and night bolus events. Each entry of the bolus calculator summary report 1140 generally includes, without limitation: a glucose data region 1142; a quartile ranges region 1144; a statistics region 1146; and an observations region 1148. In some embodiments, all of these regions appear together on the bolus calculator summary report 1140. The bolus calculator summary report 1140 shown in FIG. 16 is similar to the bolus calculator summary report 1100 (FIG. 15) in arrangement, content, and configuration. For the sake of brevity, therefore, similar or equivalent features of the bolus calculator summary report 1140 will not be redundantly described here.

Each statistics region 1146 includes one or more fields for information related to the respective correction bolus. Each statistics region 1146 may include any or all of the following information, data, or fields, without limitation: a time evaluated period; a time not evaluated period; an insulin sensitivity value; an average blood glucose entered value; an average correction bolus value; a glucose rate of change value for the time of the bolus; an average SG value for the time of the bolus; an average SG value at two hours after the bolus; an average SG value at four hours after the bolus; a number, count, or percentage of SG readings that are greater than a high threshold value (e.g., 200 mg/dL); and a number, count, or percentage of SG readings that are less than a low threshold value (e.g., 70 mg/dL). The number of fields, the amount of data included in the statistics region 1146, the arrangement and formatting of the information, and/or other features and characteristic of the statistics region 1146 may vary from that depicted in FIG. 16. Moreover, the fields and information shown in FIG. 16 are not intended to limit or otherwise restrict the scope or application of the subject matter described here.

The observations region 1148 for each bolus entry includes one or more fields that summarize the analyses and recommendations related to bolus calculator management. For example, the observations region 1148 may include a description of potentially troublesome events (hyperglycemia, hypoglycemia, glucose variability), detected glucose trends, or the like. Moreover, each observations region 1148 is utilized to provide recommendations that might be helpful to address one or more of the detected conditions. The recommendations that appear in the observations regions 1148 may include, without limitation: a recommendation to adjust (increase or decrease) the insulin sensitivity setting for the patient; a recommendation to adjust a bolus dosage for a correction bolus event; a recommendation to adjust the timing of a correction bolus; a recommendation to counsel the patient regarding proper use of the blood glucose meter, the glucose sensor, and/or the insulin infusion device; or the like. The content of each observations region 1148 may be considered to be an output of the decision support software, wherein the output can be reviewed and considered by a physician, the patient, or a caregiver for purposes of adjusting one or more settings of the insulin infusion device (in particular, the bolus calculator settings) and/or for purposes of otherwise enhancing the insulin treatment plan.

Figure 17:
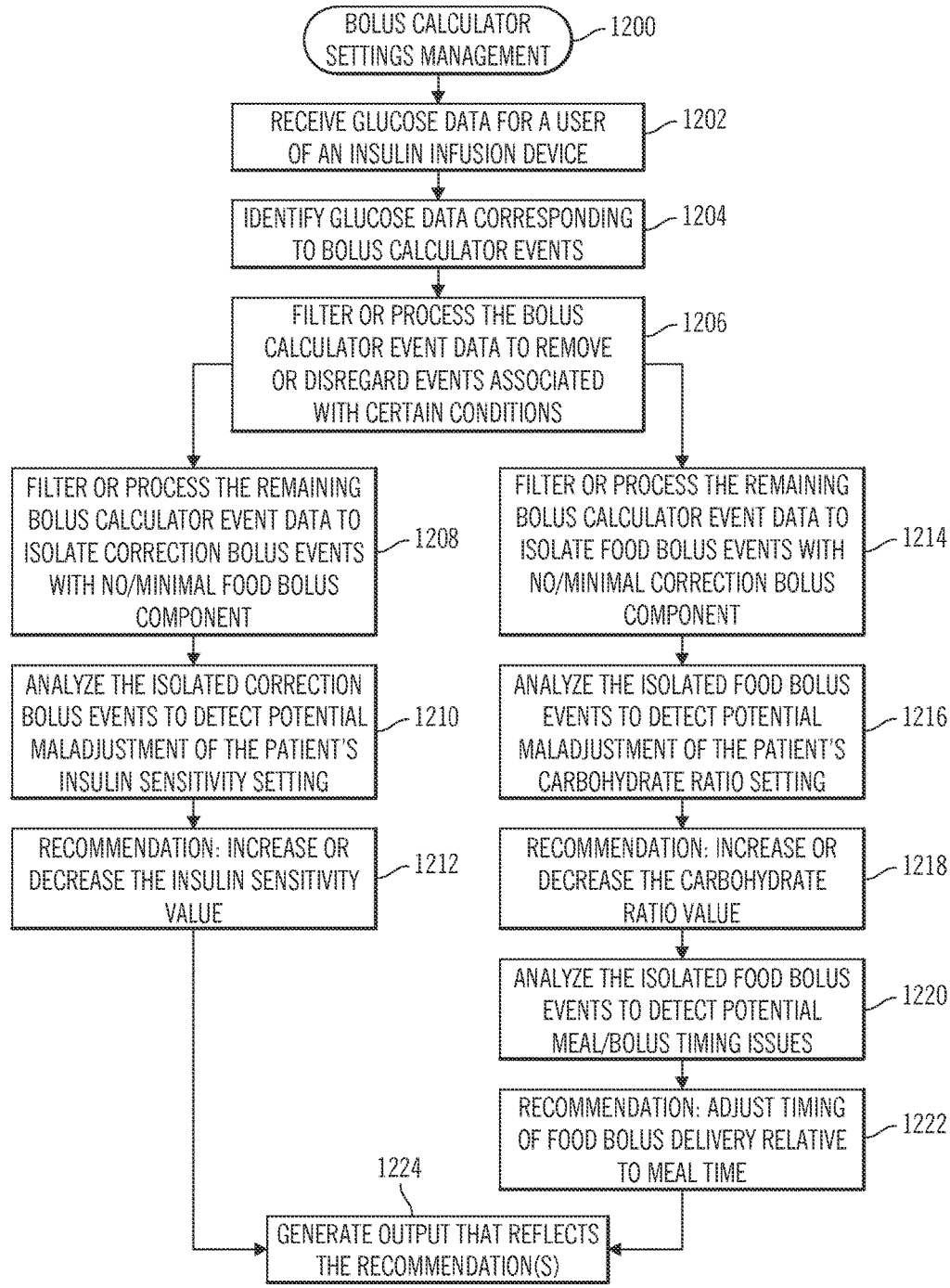
FIG. 17 is a flow chart that illustrates an embodiment of a bolus calculator settings management process.

The output that appears in the observations regions 1108, 1148 varies from patient to patient, and from day to day. Moreover, the content of the observations regions 1108, 1148 could be provided at the request of the user and/or in accordance with certain user-specified preferences or settings. The observations and recommendations are generated and provided in response to the analysis and processing of the collected sensor glucose data. In this regard, FIG. 17 is a flow chart that illustrates an embodiment of a bolus calculator settings management process 1200, which may be performed by a computing device that executes the decision support software.

The illustrated embodiment of the process 1200 receives glucose data for a user of the insulin infusion device (task 1202), as described above for task 902 of the basal pattern management process 900. The SG data received at task 1202 may be considered to be unfiltered and unaltered original SG data, wherein such original SG data can be analyzed and processed as needed to support any of the features and functions described here. That said, the process 1200 reviews the received SG data to identify bolus calculator event data corresponding to use of the bolus calculator of the insulin infusion device (task 1204). In addition, the process 1200 filters or otherwise processes the bolus calculator event data (or the received SG data) to remove or disregard bolus calculator events that are associated with certain conditions and/or to remove or disregard bolus calculator events that satisfy certain criteria (task 1206). In this regard, the bolus calculator event data may be filtered to remove glucose data associated with any of the following, without limitation: an override of a bolus dosage recommendation provided by the bolus calculator; an active insulin condition; or a back-to-back bolus condition. Of course, other flagged or observable conditions or criteria could be considered for purposes of the filtering at task 1206. The filtered bolus calculator event data can then be analyzed for trends that relate to the patient's bolus calculator settings without the presence of "noise" or interference that may otherwise be caused by certain conditions or events.

Tasks 1204, 1206 may be accomplished by searching the received SG data for flags, metadata, codes, or any type of identifier that marks a bolus calculator event or otherwise includes information that can be used to determine whether or not the filtering criteria has been satisfied. For example, the received SG data may include time stamps or metadata that indicate each time the bolus calculator was used to generate a recommended bolus dosage. The SG data may also include metadata or other information that indicates whether or not each recommended bolus was actually administered, ignored, or altered before delivery (wherein disregarding a recommended bolus or changing the calculated bolus dosage is considered to be an "override" condition). The received data may also indicate whether or not any active insulin is present in the body of the patient, where active insulin represents an estimated or projected amount of insulin that currently remains from a previous bolus. The process 1200 disregards bolus calculator events that include active insulin as a factor so that the insulin sensitivity setting can be accurately analyzed in an isolated manner (see Equations 1-3 described above). Task 1206 may also disregard a bolus calculator event that results in a back-to-back bolus condition. For example, if an additional bolus is administered within a designated period of time (e.g., two hours) following the delivery of a bolus dosage calculated by the bolus calculator, then the bolus calculator event for the initial bolus dosage is disregarded. Removal of such back-to-back bolus events ensures that the process 1200 accurately analyzes bolus calculator events on an individualized basis in the absence of potentially "overlapping" bolus time periods.

The bolus calculator settings management process 1200 analyzes bolus calculator events having only a correction insulin component separately from bolus calculator events having only a food insulin component. Accordingly, FIG. 17 depicts two parallel branches of the process 1200, which may be executed concurrently, sequentially, simultaneously, or the like. Referring to the "correction component" branch (which appears on the left), the process 1200 filters or otherwise processes the remaining bolus calculator event data to isolate correction bolus events having no food bolus component, or a minimal food bolus component (task 1208). When Carbs=0, Equation 2 is simplified to Food Insulin=0 and, therefore, Equation 1 reduces to Total Bolus=Correction Insulin−Active Insulin. Likewise, Equation 1 reduces to Total Bolus=Correction Insulin−Active Insulin when Food Insulin is substantially less than Correction Insulin. However, at this point the process 1200 assumes that no active insulin is present. Accordingly, $$\text{Total Bolus} = \text{Correction Insulin} = \frac{\text{Current } BG - \text{High } BG \text{ Target}}{\text{Insulin Sensitivity}}.$$

This allows the process 1200 to analyze the isolated correction bolus events to detect potential maladjustment of the patient's insulin sensitivity value (task 1210), which is one of the adjustable user-specified bolus calculator settings.

Task 1210 analyzes the SG data for at least some of the isolated correction bolus events for the presence of any of a plurality of event occurrences that are indicative of a potentially correctable insulin sensitivity setting. Task 1210 may leverage empirical data, the results of clinical studies, and/or historical data to discover certain detectable patterns, trends, or characteristics of the SG data. In practice, therefore, the decision support software can be written such that task 1210 compares the relevant SG data against any number of predefined conditions, which in turn correspond to a suboptimal, suspicious, or potentially troublesome insulin sensitivity setting.

In response to the detection of one or more relevant event occurrences, the process 1200 generates and outputs an appropriate recommendation (task 1212). The recommendation includes a suggestion or instruction to adjust the insulin sensitivity setting in an appropriate manner to address the detected condition(s). More specifically, task 1212 provides a recommendation to increase or decrease the insulin sensitivity value. In certain embodiments, task 1212 may also suggest an amount to increase or decrease the insulin sensitivity, or suggest a range of adjustment values for consideration. Although the process 1200 and the decision support software may check for the presence of any number of conditions and provide a variety of different adjustment recommendations, a number of non-limiting examples are provided here for ease of understanding.

In accordance with some embodiments, task 1210 of the process 1200 checks for a long term hypoglycemic event or condition occurring after a correction bolus event. "Long term" in this context may refer to any designated time and/or period of time relative to the time when the correction bolus dosage was administered (e.g., the 0:00 time). "Long term" is used here to specify an end of insulin action time. In this regard, most of the commercially available fast acting insulin analogs have an action time of three to five hours. At the end of the insulin action time, the user should see the appropriate correction of glucose. An excessive dose can lead to hypoglycemia when all of the insulin has acted in the body, while an insufficient dose can lead to hyperglycemia.

Figure 18:
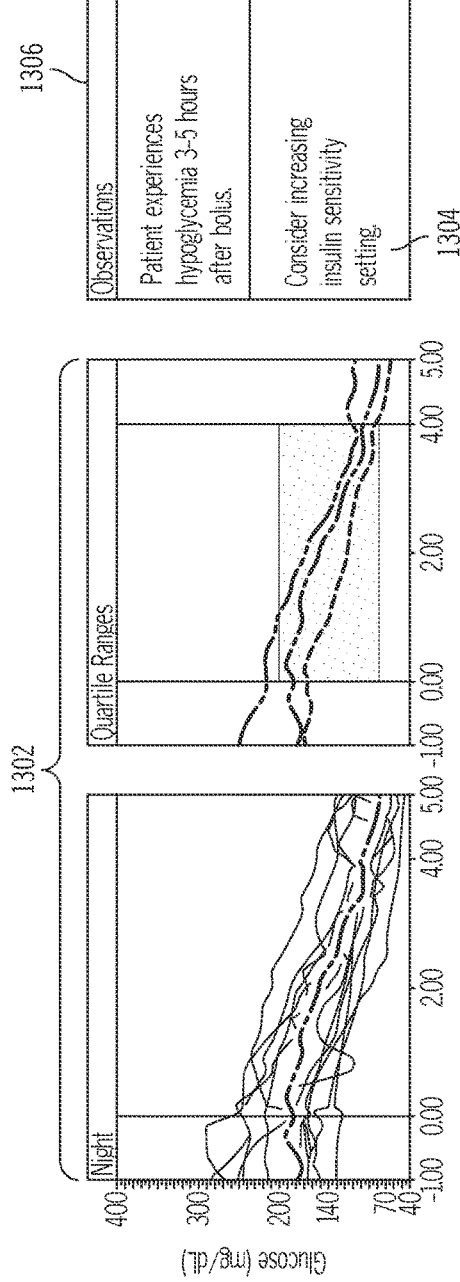
FIG. 18 depicts glucose data for a correction bolus event and a corresponding recommendation related to a hypoglycemic condition.

FIG. 18 depicts glucose data 1302 for a correction bolus event and a corresponding recommendation 1304 related to a long term hypoglycemic condition. FIG. 18 shows how the glucose data 1302 between 3:00 hours and 5:00 hours (post-bolus) indicates hypoglycemia, e.g., SG levels below 70 mg/dL. For this particular example, the detected amount, severity, and/or frequency of hypoglycemia satisfies the designated reporting criteria and, therefore, the decision support software detects this condition as an event occurrence for purposes of outputting the associated recommendation 1304. The observations region 1306 depicted in FIG. 18 includes a description of the detected event occurrence, along with the associated recommendation: "Patient experiences hypoglycemia 3-5 hours after bolus. Consider increasing insulin sensitivity setting." Accordingly, when task 1210 detects a long term hypoglycemic event occurring after a correction bolus event, the recommendation at task 1212 includes a suggestion to increase the patient's insulin sensitivity value.

Task 1210 of the process 1200 may also check for long term glycemic variability occurring after a correction bolus event, e.g., three to five hours after delivery of the correction bolus. Glycemic variability refers to a wide distribution of SG readings at or near the time period under analysis. A determination of glycemic variability may be based on the difference between maximum and minimum SG readings, the difference between quartile ranges, or the like. The specific manner in which glycemic variability is determined may vary from one embodiment to another.

Figure 19:
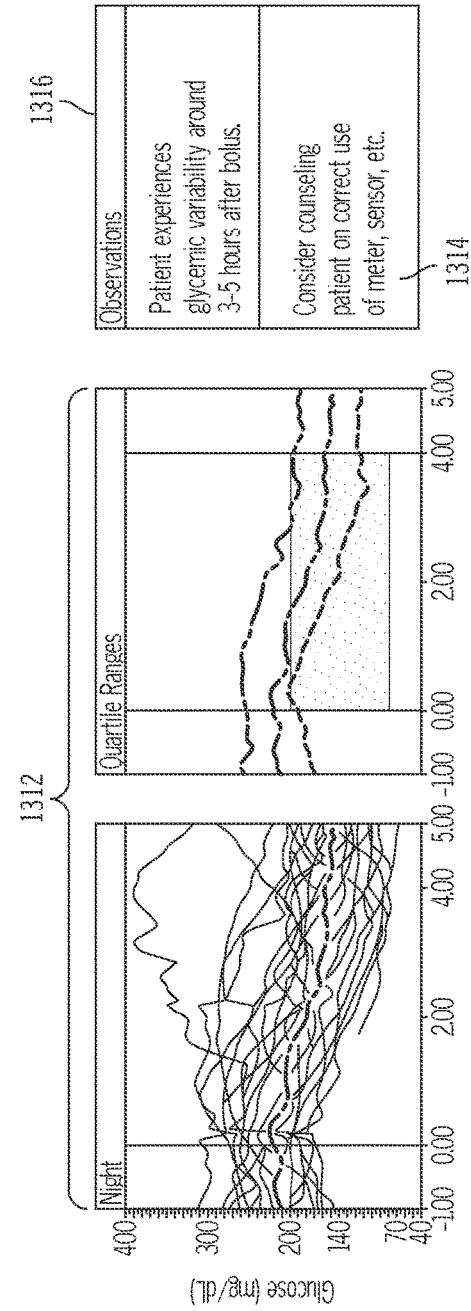
FIG. 19 depicts glucose data for a correction bolus event and a corresponding recommendation related to a glycemic variability condition.

FIG. 19 depicts glucose data 1312 for a correction bolus event and a corresponding recommendation 1314 related to a long term glycemic variability condition. FIG. 19 shows how the glucose data 1312 between 3:00 hours and 5:00 hours (post-bolus) varies by a noticeable margin. For this particular example, the detected variation or distribution of SG readings within the three-to-five hour time window satisfies the designated reporting criteria and, therefore, the decision support software detects this condition as an event occurrence for purposes of outputting the associated recommendation 1314. The observations region 1316 depicted in FIG. 19 includes a description of the detected event occurrence, along with the associated recommendation: "Patient experiences glycemic variability around 3-5 hours after bolus. Consider counseling patient on correct use of meter, sensor, etc." Accordingly, when task 1210 detects long term glycemic variability occurring after a correction bolus event, the recommendation at task 1212 includes a suggestion to counsel, educate, or train the patient in an appropriate manner with respect to the use of the blood glucose meter, the glucose sensor, the insulin infusion device, or the like.

Figure 20:
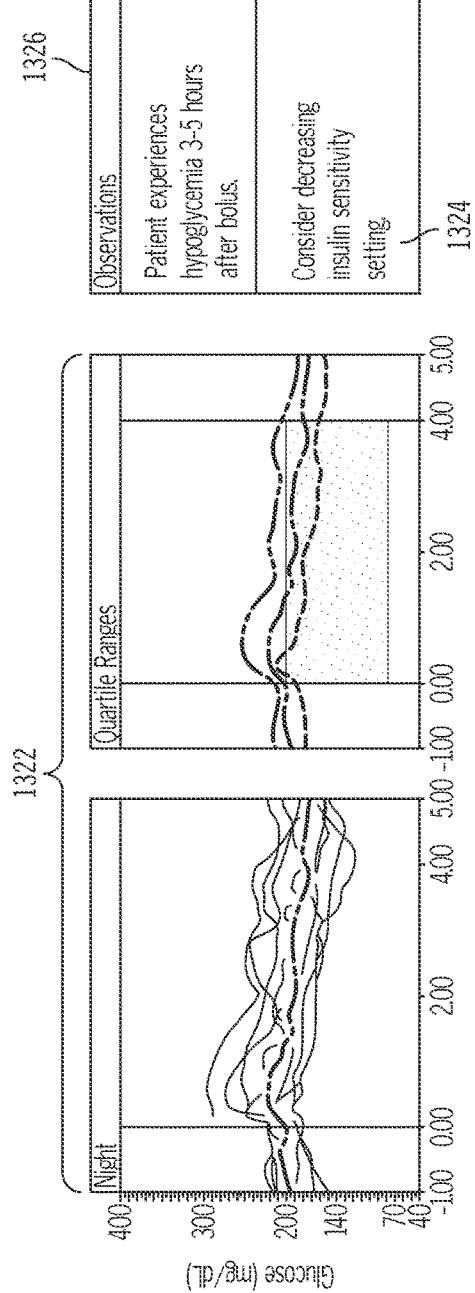
FIG. 20 depicts glucose data for a correction bolus event and a corresponding recommendation related to a hyperglycemic condition.

Task 1210 of the process 1200 may also check for a long term hyperglycemic event or condition occurring after a correction bolus event, e.g., three to five hours after the correction bolus. In this regard, FIG. 20 depicts glucose data 1322 for a correction bolus event and a corresponding recommendation 1324 related to a long term hyperglycemic condition. FIG. 20 shows how the glucose data 1322 between 3:00 hours and 5:00 hours (post-bolus) indicates hyperglycemia, e.g., SG levels above 200 mg/dL. For this particular example, the detected amount, severity, and/or frequency of hyperglycemia satisfies the designated reporting criteria and, therefore, the decision support software detects this condition as an event occurrence for purposes of outputting the associated recommendation 1324. The observations region 1326 depicted in FIG. 20 includes a description of the detected event occurrence, along with the associated recommendation: "Patient experiences hyperglycemia 3-5 hours after bolus. Consider decreasing insulin sensitivity setting." Accordingly, when task 1210 detects a long term hyperglycemic event occurring after a correction bolus event, the recommendation at task 1212 includes a suggestion to decrease the patient's insulin sensitivity value.

Task 1210 of the process 1200 may also check for a rapid decrease in blood glucose level occurring in a short time after a correction bolus event. As used here, "a short time" refers to a typical peak of insulin action time. Commercially available rapid acting insulin typically has a peak time of action at about 90 minutes to three hours. During this time, the patient's blood glucose level should be in close proximity to the blood glucose level that is half way toward their target glucose. In this context, the process 1200 may analyze certain characteristics or trends at or near a designated time (e.g., at two hours post-bolus, during a thirty minute window that includes the two hour post-bolus time, or the like). Alternatively or additionally, the process 1200 may analyze certain characteristics or trends leading up to a designated time.

Figure 21:
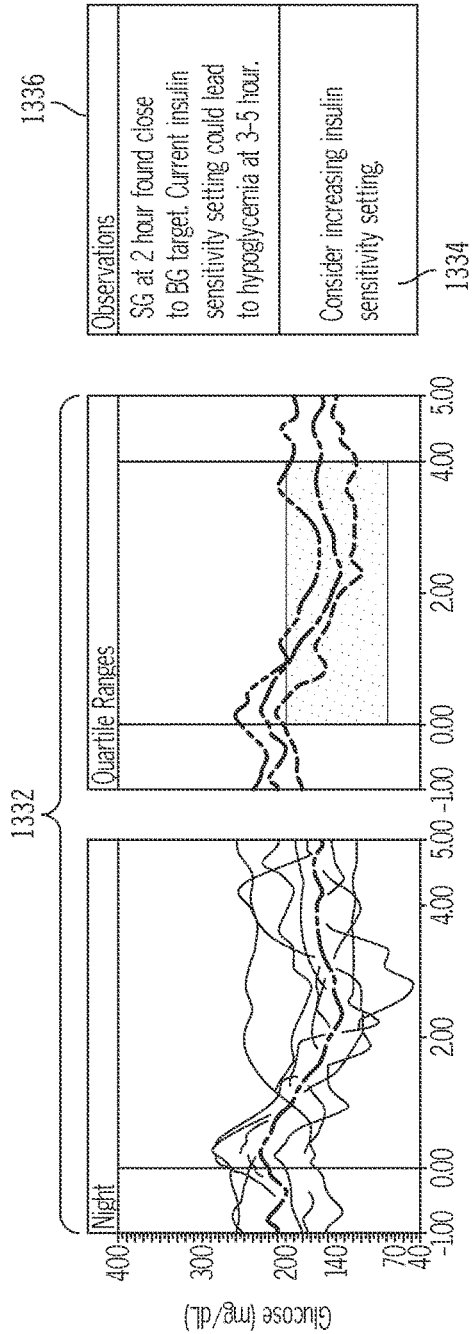
FIG. 21 depicts glucose data for a correction bolus event and a corresponding recommendation related to a rapidly decreasing glucose condition.

FIG. 21 depicts glucose data 1332 for a correction bolus event and a corresponding recommendation 1334 related to rapidly decreasing glucose condition. FIG. 21 shows how the glucose data 1332 immediately preceding 2:00 hours (post-bolus) exhibits a sharp decline that approaches the patient's target glucose range. For this particular example, the detected rapid decrease in SG readings leading to the 2:00 hour mark satisfies the designated reporting criteria and, therefore, the decision support software detects this condition as an event occurrence for purposes of outputting the associated recommendation 1334. The observations region 1336 depicted in FIG. 21 includes a description of the detected event occurrence, along with the associated recommendation: "SG at 2 hour found close to BG target. Current insulin sensitivity setting could lead to hypoglycemia at 3-5 hour. Consider increasing insulin sensitivity setting." Accordingly, when task 1210 detects an event occurrence that is indicative of a rapid decrease in blood glucose level at or near the designated "short time" mark, the recommendation at task 1212 includes a suggestion to increase the insulin sensitivity value of the bolus calculator. In practice, the decision support software may be designed to check for a rapidly declining trend in the SG data, and to check the SG readings at the designated time (e.g., the two hour mark) to determine whether the SG readings are close the BG target.

Task 1210 of the process 1200 may also check for short term glycemic variability occurring after a correction bolus event, e.g., at or near two hours after delivery of the correction bolus. The determination of short term glycemic variability may be based on the difference between maximum and minimum SG readings, the difference between quartile ranges, or the like. The specific manner in which short term glycemic variability is determined may vary from one embodiment to another.

FIG. 22 depicts glucose data 1342 for a correction bolus event and a corresponding recommendation 1344 related to a short term glycemic variability condition. FIG. 22 shows how the glucose data 1342 at or near the 2:00 hour mark (post-bolus) varies by a noticeable margin. For this particular example, the detected variation or distribution of SG readings at two hours post-bolus satisfies the designated reporting criteria and, therefore, the decision support software detects this condition as an event occurrence for purposes of outputting the associated recommendation 1344. The observations region 1346 depicted in FIG. 22 includes a description of the detected event occurrence, along with the associated recommendation: "Patient experiences glycemic variability at 2 hours after bolus. Consider counseling patient on carb counting, meal timing, etc." Accordingly, when task 1210 detects short term glycemic variability occurring after a correction bolus event, the recommendation at task 1212 includes a suggestion to counsel, educate, or train the patient in an appropriate manner with respect to meal/bolus timing, dietary habits, accurately estimating carbohydrate consumption, or the like.

Task 1210 of the process 1200 may also check for a limited decrease in blood glucose level occurring a short time after a correction bolus event, such as the two hour (post-bolus) time. In this regard, FIG. 23 depicts glucose data 1352 for a correction bolus event and a corresponding recommendation 1354 related to a condition associated with limited decrease in glucose level. FIG. 23 shows how the glucose data 1352 immediately preceding 2:00 hours (post-bolus) remains close to the level at the 0:00 hour mark. In other words, it appears as though the correction bolus has had little to no impact at the 2:00 hour mark. For this particular example, the detected limited decrease in SG reading at the 2:00 hour mark, relative to the 0:00 hour mark, satisfies the designated reporting criteria and, therefore, the decision support software detects this condition as an event occurrence for purposes of outputting the associated recommendation 1354. The observations region 1356 depicted in FIG. 23 includes a description of the detected event occurrence, along with the associated recommendation: "SG at 2 hour found much higher than BG target. Consider decreasing insulin sensitivity setting." Accordingly, when task 1210 detects an event occurrence that is indicative of a limited decrease in blood glucose level at or near the designated "short time" mark, the recommendation at task 1212 includes a suggestion to decrease the insulin sensitivity value of the bolus calculator. In certain embodiments, the decision support software is designed to check and compare the SG values at the zero hour mark and the two hour mark, and to compare the SG readings at the two hour mark to the BG target. For example, the decision support software may compare the SG readings at the two hour mark to the value that is halfway to the target BG. If the SG readings are over 60 mg/dL above the halfway point, then a recommendation is provided.

Task 1210 can be utilized to detect one or more event occurrences, which in turn may influence the content of the recommendation(s) generated at task 1212. Regardless of which event occurrences, if any, are detected, the process 1200 may continue by generating an output that includes, conveys, or otherwise reflects the recommendations (task 1224). In this regard, the recommendations are influenced by, and are associated with, the detected event occurrences. The output may be a report (see FIG. 16) suitable for display, printing, and/or transmission to a destination device, wherein the recommendations included on the report are intended to address the detected event occurrences. In certain embodiments, the process 1200 generates and sends one or more commands to initiate the adjustment of the insulin sensitivity setting of the bolus calculator in accordance with the recommendations. In other words, the process 1200 may allow a caregiver to review and consider a recommended adjustment approach and then actually initiate an adjustment to be automatically carried out at the insulin infusion device.

It should be appreciated that the process 1200 could be designed to monitor for any number of different predefined event occurrences related to the delivery of correction boluses, and that the particular detection algorithms, formulas, and relationships may vary from one embodiment to another. Such variations are contemplated by this disclosure.

As mentioned previously, the process 1200 also analyzes bolus calculator events having only a food insulin component. The "food component" branch of the process 1200 appears on the right of FIG. 17. In this regard, the decision support software filters or otherwise processes the bolus calculator event data to isolate food bolus events having a minimal, if any, correction bolus component (task 1214). In practice, the process 1200 may perform task 1214 by identifying bolus calculator events where either a value of zero (or its equivalent) was entered for the current blood glucose measurement or the patient's blood glucose measurement was very close to the target (the Current BG value in Equation 3). When Current BG=0 or Current BG≅High BG Target, the process 1200 disregards the correction insulin term (Equation 3). Accordingly, Equation 1 reduces to Total Bolus=Food Insulin. Also at this point the process 1200 assumes that no active insulin is present. Accordingly, $$\text{Total Bolus} = \text{Food Insulin} = \frac{Carbs}{Carb\ Ratio}.$$

This allows the process 1200 to analyze the isolated food bolus events to detect potential maladjustment of the patient's carbohydrate ratio value (task 1216), which is one of the adjustable user-specified bolus calculator settings.

Task 1216 analyzes the SG data corresponding to at least some of the isolated food bolus events to detect the presence of any of a plurality of event occurrences that are indicative of a potentially correctable carbohydrate ratio setting. Task 1216 may leverage empirical data, the results of clinical studies, and/or historical data to discover certain detectable patterns, trends, or characteristics of the SG data. In practice, therefore, the decision support software can be written such that task 1216 compares the relevant SG data against any number of predefined conditions, which in turn correspond to a suboptimal, suspicious, or potentially troublesome carbohydrate ratio setting.

In response to the detection of one or more relevant event occurrences, the process 1200 generates and outputs an appropriate recommendation (task 1218). The recommendation includes a suggestion or instruction to adjust the carbohydrate ratio setting in an appropriate manner to address the detected condition(s). More specifically, task 1218 provides a recommendation to increase or decrease the carbohydrate ratio value. In certain embodiments, task 1218 may also suggest an amount to increase or decrease the carbohydrate ratio value, or suggest a range of adjustment values for consideration. Although the process 1200 and the decision support software may check for the presence of any number of conditions and provide a variety of different adjustment recommendations, a number of non-limiting examples are provided here for ease of understanding.

Figure 24:
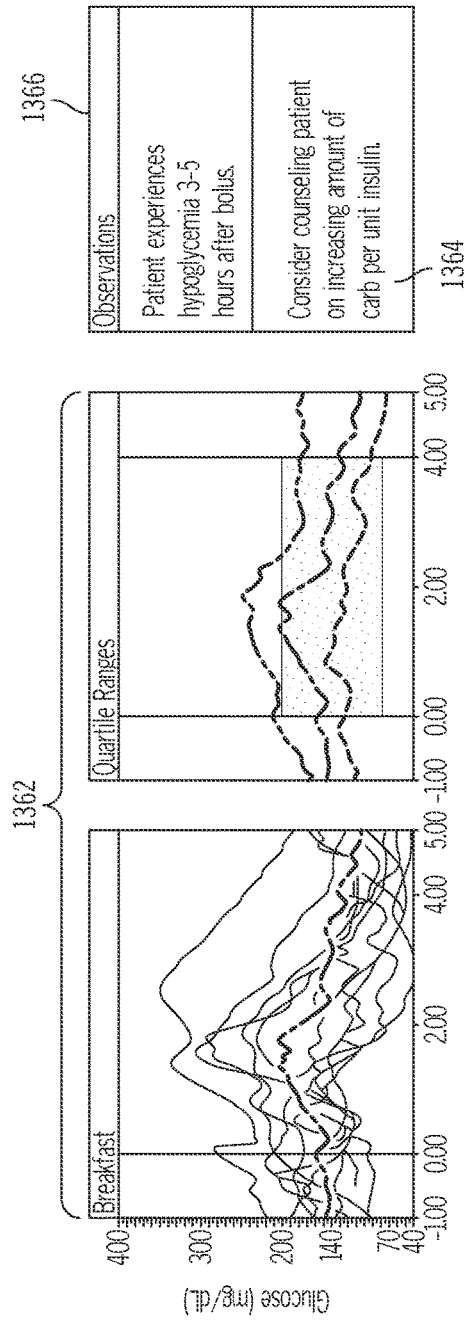
FIG. 24 depicts glucose data for a food bolus event and a corresponding recommendation related to a hypoglycemic condition.

In accordance with some embodiments, task 1216 of the process 1200 checks for a long term hypoglycemic event or condition occurring after a food bolus event, e.g., three to five hours after delivery of the food bolus. In this regard, FIG. 24 depicts glucose data 1362 for a food bolus event and a corresponding recommendation 1364 related to a long term hypoglycemic condition. FIG. 24 illustrates how the glucose data 1362 between 3:00 hours and 5:00 hours (post-bolus) indicates hypoglycemia, e.g., SG levels below 70 mg/dL. For this particular example, the detected amount, severity, and/or frequency of hypoglycemia satisfies the designated reporting criteria and, therefore, the decision support software detects this condition as an event occurrence for purposes of outputting the associated recommendation 1364. The observations region 1366 depicted in FIG. 24 includes a description of the detected event occurrence, along with the associated recommendation: "Patient experiences hypoglycemia 3-5 hours after bolus. Consider counseling patient on increasing amount of carb per unit insulin." Accordingly, when task 1216 detects a long term hypoglycemic event occurring after a food bolus event, the recommendation at task 1218 includes a suggestion to increase the patient's carbohydrate ratio value.

Figure 25:
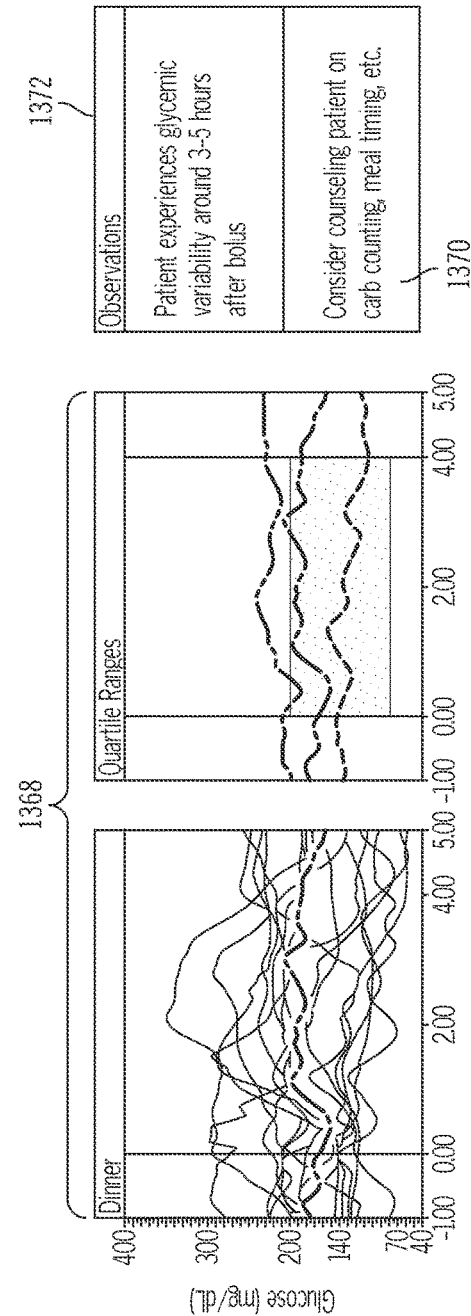
FIG. 25 depicts glucose data for a food bolus event and a corresponding recommendation related to a glycemic variability condition.

Task 1216 of the process 1200 may also check for long term glycemic variability occurring after a food bolus event, e.g., three to five hours after delivery of the food bolus. In this context, FIG. 25 depicts glucose data 1368 for a food bolus event and a corresponding recommendation 1370 related to a glycemic variability condition detected well after the food bolus event. FIG. 25 shows how the glucose data 1368 between 3:00 hours and 5:00 hours (post-bolus) varies by a noticeable margin. For this particular example, the detected variation or distribution of SG readings within the three-to-five hour time window satisfies the designated reporting criteria and, therefore, the decision support software detects this condition as an event occurrence for purposes of outputting the associated recommendation 1370. The observations region 1372 depicted in FIG. 25 includes a description of the detected event occurrence, along with the associated recommendation: "Patient experiences glycemic variability around 3-5 hours after bolus. Consider counseling patient on carb counting, meal timing, etc." Accordingly, when task 1216 detects long term glycemic variability occurring after a food bolus event, the recommendation at task 1218 includes a suggestion to counsel, educate, or train the patient in an appropriate manner with respect to meal/bolus timing, dietary habits, accurately estimating carbohydrate consumption, or the like.

Task 1216 of the process 1200 may also check for a long term hyperglycemic event or condition occurring after a food bolus event, e.g., three to five hours after the food bolus. In this regard, FIG. 26 depicts glucose data 1374 for a food bolus event and a corresponding recommendation 1376 related to a long term hyperglycemic condition. FIG. 26 shows how the glucose data 1374 between 3:00 hours and 5:00 hours (post-bolus) indicates hyperglycemia, e.g., SG levels above 200 mg/dL. For this particular example, the detected amount, severity, and/or frequency of hyperglycemia satisfies the designated reporting criteria and, therefore, the decision support software detects this condition as an event occurrence for purposes of outputting the associated recommendation 1376. The observations region 1378 depicted in FIG. 26 includes a description of the detected event occurrence, along with the associated recommendation: "Patient experiences hyperglycemia 3-5 hours after bolus. Consider counseling patient on decreasing amount of carb per unit insulin." Accordingly, when task 1216 detects a long term hyperglycemic event occurring after a food bolus event, the recommendation at task 1218 includes a suggestion to decrease the patient's carbohydrate ratio value.

Task 1216 of the process 1200 may also check for limited or no increase in blood glucose level occurring in a short time after a food bolus event, such as the two hour (post-bolus) time. In this regard, FIG. 27 depicts glucose data 1380 for a food bolus event and a corresponding recommendation 1382 related to a condition associated with limited increase in glucose level. FIG. 27 shows how the glucose reading at or near the 2:00 hour mark (post-bolus) remains close to the level at the 0:00 hour mark. In other words, it appears as though the food has had little to no impact at the 2:00 hour mark. For this particular example, the detected limited increase in the glucose data 1380 at the 2:00 hour mark, relative to the 0:00 hour mark, satisfies the designated reporting criteria and, therefore, the decision support software detects this condition as an event occurrence for purposes of outputting the associated recommendation 1382. The observations region 1384 depicted in FIG. 27 includes a description of the detected event occurrence, along with the associated recommendation: "SG at 2 hour found less than 30 mg/dL from SG at bolus. Consider counseling patient on increasing amount of carb per unit insulin." This example considers a difference threshold of 30 mg/dL. In other embodiments, however, the difference threshold may be more or less than 30 mg/dL, and the threshold could vary depending upon various factors such as the time of day, the day of the month, the season, etc. Regardless of the criteria used, when task 1216 detects an event occurrence that is indicative of a limited increase in blood glucose level occurring at or near the designated "short time" mark, the recommendation at task 1218 includes a suggestion to increase the carbohydrate ratio value of the bolus calculator.

Task 1216 of the process 1200 may also check for short term glycemic variability occurring after a food bolus event, e.g., at or near two hours after delivery of the food bolus. In this regard, FIG. 28 depicts glucose data 1386 for a food bolus event and a corresponding recommendation 1388 related to a short term glycemic variability condition. FIG. 28 shows how the glucose data 1386 at or near the 2:00 hour mark (post-bolus) varies by a noticeable margin. For this particular example, the detected variation or distribution of SG readings at two hours post-bolus satisfies the designated reporting criteria and, therefore, the decision support software detects this condition as an event occurrence for purposes of outputting the associated recommendation 1388. The observations region 1390 depicted in FIG. 28 includes a description of the detected event occurrence, along with the associated recommendation: "Patient experiences glycemic variability at 2 hours after bolus. Consider counseling patient on carb counting, meal timing, etc." Accordingly, when task 1216 detects short term glycemic variability occurring after a food bolus event, the recommendation at task 1218 includes a suggestion to counsel, educate, or train the patient in an appropriate manner with respect to meal/bolus timing, dietary habits, accurately estimating carbohydrate consumption, or the like.

Task 1216 of the process 1200 may also check for a high increase in blood glucose level occurring a short time after a food bolus event, e.g., at or near the 2:00 hour (post-bolus) time. In this context, FIG. 29 depicts glucose data 1392 for a food bolus event and a corresponding recommendation 1394 related to a high glucose increase condition. FIG. 29 shows how the glucose reading at or near the 2:00 hour mark (post-bolus) is substantially higher than the glucose reading at the 0:00 hour. For this particular example, the large increase in the glucose data 1392 at the 2:00 hour mark, relative to the 0:00 hour mark, satisfies the designated reporting criteria and, therefore, the decision support software detects this condition as an event occurrence for purposes of outputting the associated recommendation 1394. The observations region 1396 depicted in FIG. 29 includes a description of the detected event occurrence, along with the associated recommendation: "SG at 2 hour found more than 60 mg/dL from SG at bolus. Consider counseling patient on decreasing amount of carb per unit insulin." This example considers a difference threshold of 60 mg/dL. In other embodiments, however, the difference threshold may be more or less than 60 mg/dL, and the threshold could vary depending upon various factors such as the time of day, the day of the month, the season, etc. Regardless of the criteria used, when task 1216 detects an event occurrence that is indicative of a substantial or rapid increase in blood glucose level occurring at or near the designated "short time" mark, the recommendation at task 1218 includes a suggestion to decrease the carbohydrate ratio value of the bolus calculator.

The "food component" branch of the process 1200 may also analyze the isolated food bolus events to detect potential meal/bolus timing issues (task 1220) and, if so, to generate one or more recommendations (task 1222) to adjust the timing of food boluses relative to meal consumption times. In certain embodiments, task 1220 checks for excursions and/or high glucose rate of change trends for a time period immediately following a food bolus.

Figure 30:
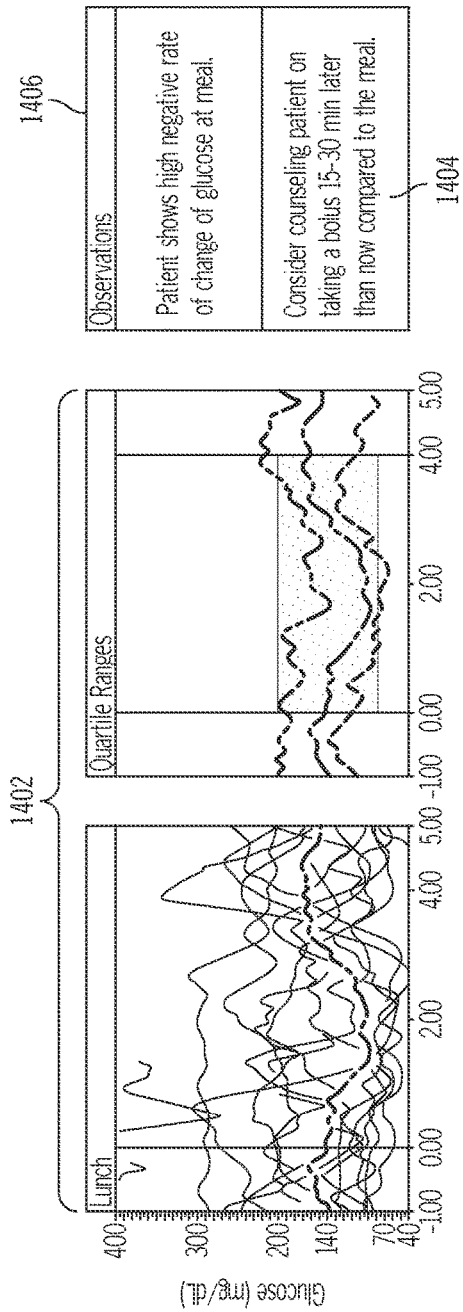
FIG. 30 depicts glucose data for a food bolus event and a corresponding recommendation related to a high negative rate of change condition.

As one example, task 1220 checks for: (1) a limited increase in glucose level and/or hypoglycemia from the 0:00 hour mark (corresponding to the time of the food bolus) to some designated time thereafter, such as the 2:00 hour mark; and (2) a high negative rate of change at the 0:00 mark. In this regard, FIG. 30 depicts glucose data 1402 for a food bolus event and a corresponding recommendation 1404 related to a combination of these two conditions. FIG. 30 shows how the glucose reading at or near the 2:00 hour mark (post-bolus) has not increased relative to the glucose reading at the 0:00 hour. In fact, the glucose level has dropped slightly going from the 0:00 hour to the 2:00 hour. Accordingly, the first of the two conditions mentioned above will be detected. Moreover, the glucose data 1402 exhibits a relatively high negative rate of change at the 0:00 hour mark, i.e., at or close to the patient's meal time. Thus, the second of the two conditions will also be detected. Consequently, the decision support software considers the corresponding event occurrence for purposes of outputting the associated recommendation 1404. The observations region 1406 depicted in FIG. 30 includes a description of the detected event occurrence, along with the associated recommendation: "Patient shows high negative rate of change of glucose at meal. Consider counseling patient on taking a bolus 15-30 minutes later than now compared to the meal."

The threshold for determining whether or not there has been a "limited increase" in glucose level, and the threshold for determining whether or not the negative rate of change is high enough to trigger the recommendation, may vary from one embodiment to another. Moreover, one or both of these thresholds could vary depending upon various factors such as the time of day, the day of the month, the season, etc. Regardless of the criteria used, when task 1220 detects an event occurrence that is indicative of both a limited increase in short term glucose levels and a high negative rate of change at the time of the food bolus, the recommendation at task 1222 includes a suggestion to take the food bolus later in time.

Figure 31:
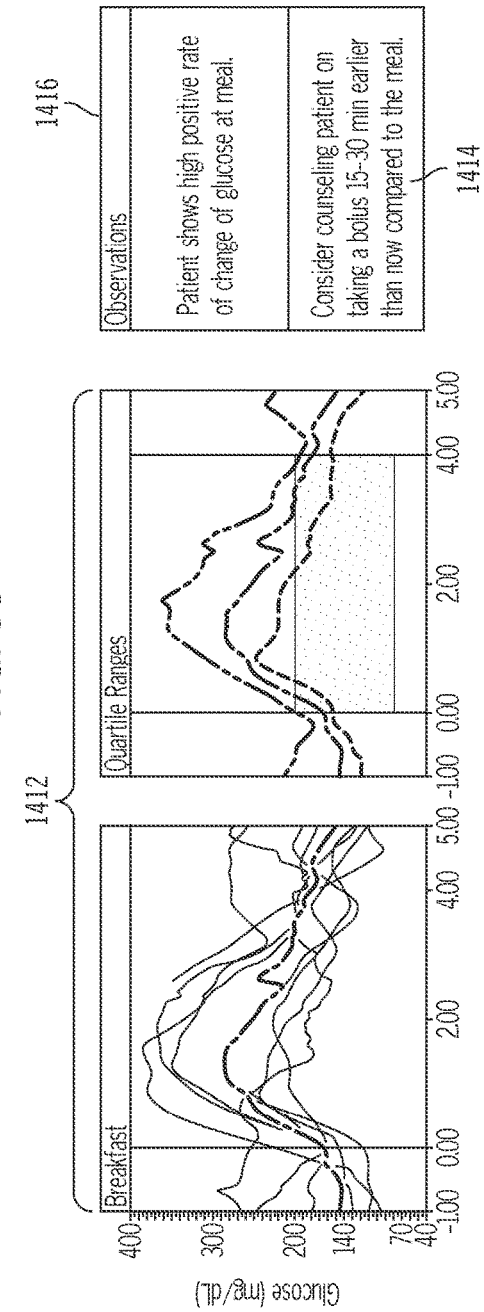
FIG. 31 depicts glucose data for a food bolus event and a corresponding recommendation related to a high positive rate of change.

As another example, task 1220 may check for: (1) a substantial increase in glucose level from the 0:00 hour mark to some designated time thereafter, such as the 2:00 hour mark; and (2) a high positive rate of change at the 0:00 mark. In this regard, FIG. 31 depicts glucose data 1412 for a food bolus event and a corresponding recommendation 1414 related to a combination of these two conditions. FIG. 31 shows how the glucose reading at or near the 2:00 hour mark (post-bolus) has increased by a large margin relative to the glucose reading at the 0:00 hour. Accordingly, the first of the two conditions mentioned above will be detected. Moreover, the glucose data 1412 exhibits a relatively high positive rate of change at the 0:00 hour mark, i.e., the glucose data 1412 is trending upwards at the 0:00 hour. Thus, the second of the two conditions will also be detected. Consequently, the decision support software flags this corresponding event occurrence for purposes of outputting the associated recommendation 1414. The observations region 1416 depicted in FIG. 31 includes a description of the detected event occurrence, along with the associated recommendation: "Patient shows high positive rate of change of glucose at meal. Consider counseling patient on taking a bolus 15-30 minutes earlier than now compared to the meal."

The threshold for determining whether or not there has been a "substantial increase" in glucose level, and the threshold for determining whether or not the positive rate of change is high enough to trigger the recommendation, may vary from one embodiment to another. Moreover, one or both of these thresholds could vary depending upon various factors such as the time of day, the day of the month, the season, etc. Regardless of the criteria used, when task 1220 detects an event occurrence that is indicative of both a large increase in short term glucose levels and a high positive rate of change at the time of the food bolus, the recommendation at task 1222 includes a suggestion to take the food bolus earlier in time.

As described above, tasks 1216, 1220 can be utilized to detect one or more event occurrences, which in turn may influence the content of the recommendation(s) generated at task 1222. Regardless of which event occurrences, if any, are detected, the process 1200 may continue to task 1224 for purposes of generating an appropriate output that conveys the recommendations. The output may be a report (see FIG. 15) suitable for display, printing, and/or transmission to a destination device, wherein the recommendations included on the report are intended to address the detected event occurrences. In certain embodiments, the process 1200 generates and sends one or more commands to initiate the adjustment of the carbohydrate ration setting of the bolus calculator in accordance with the recommendations. In other words, the process 1200 may allow a caregiver to review and consider a recommended adjustment approach and then actually initiate an adjustment to be automatically carried out at the insulin infusion device.

In practice, the process 1200 may utilize a prioritization scheme and/or a "conflict resolution" approach to ensure that counter-recommendations are not provided. For example, the decision support software should not concurrently generate a first recommendation to increase the insulin sensitivity value and a second recommendation to decrease the insulin sensitivity value. In certain embodiments, the decision support software handles potentially conflicting food bolus instructions using an ordered analysis scheme. More specifically, the process 1200 checks for certain event occurrences in a predetermined sequence and only makes one recommendation at a time. In other words, if the process 1200 determines that a recommendation needs to be made, it need not continue checking for other event occurrences (at least until the next analysis session).

For this particular example, the ordered analysis is as follows: (1) check for long term hypoglycemia (during the 3:00 hour to 5:00 hour post-bolus period); (2) check for short term hypoglycemia (occurring at or near 2:00 hours post-bolus); (3) check for long term high glycemic variability; (4) check for short term high glycemic variability; (5) check for long term hyperglycemia; and (6) check for short term hyperglycemia. Thus, if long term hypoglycemia is detected, the appropriate adjustment recommendation is generated as an output, and the other checks are not made. As another example, assume that the first three checks are completed without triggering any recommendations. Thereafter, short term high glycemic variability is detected. At that point, the appropriate adjustment recommendation is generated as an output, and the remaining two checks are not performed. The ordering of the checks may be adjusted or altered based on the detected intensity of the hypoglycemic or hyperglycemic condition. In addition, meal timing suggestions could be provided in conjunction with any of the recommendations. The above ordering is merely exemplary, and is not intended to restrict the scope or application of the subject matter described here.

It should be appreciated that the process 1200 could be designed to monitor for any number of different predefined event occurrences related to the delivery of food boluses, and that the particular detection algorithms, formulas, and relationships may vary from one embodiment to another. Such variations and options are contemplated by this disclosure.

Glucose Trend Summary Report

Figure 32:
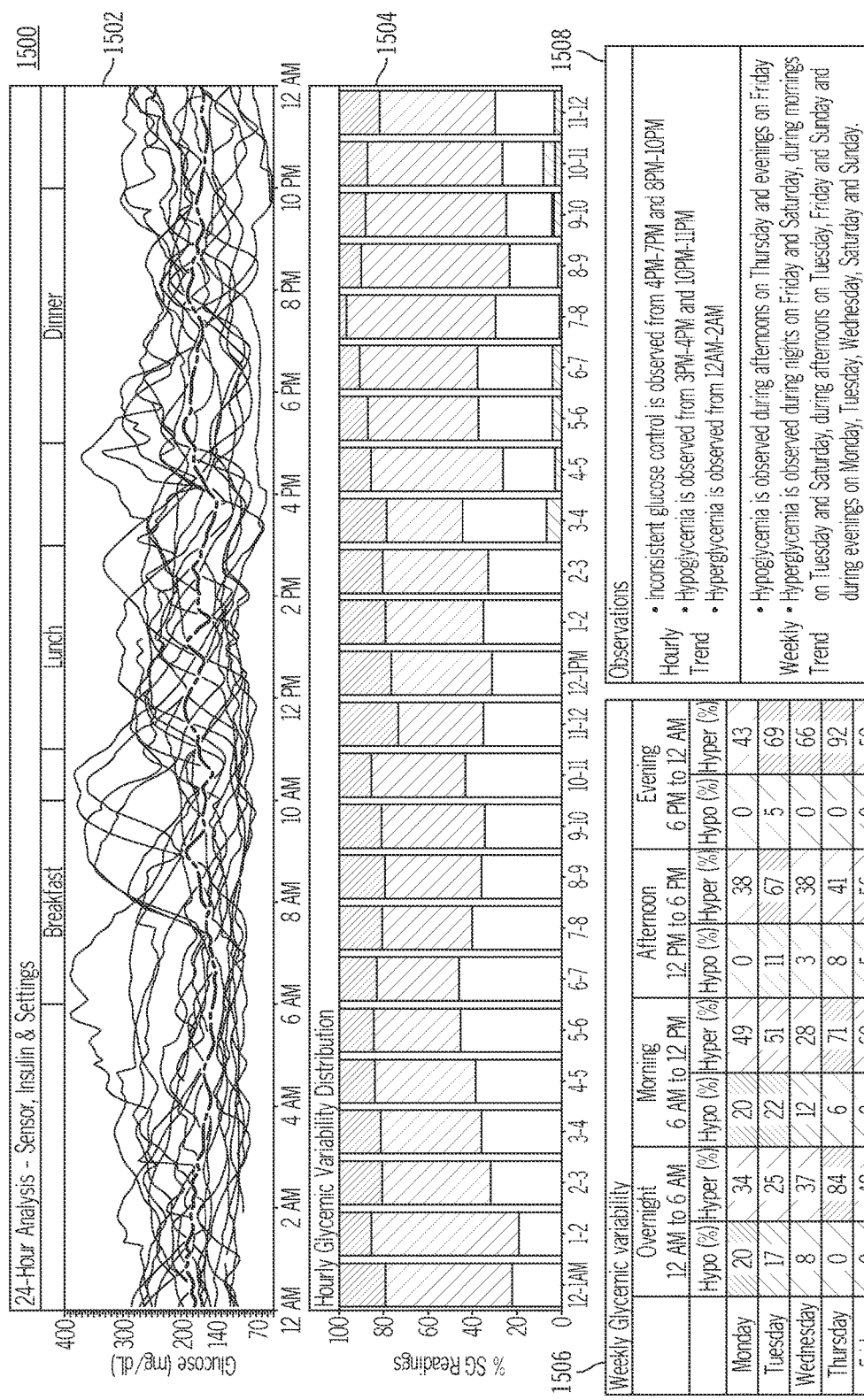
FIG. 32 illustrates a sample of a glucose trend summary report, which may be generated in accordance with embodiments of the invention.

The decision support software described here also supports a variety of reporting and display features related to the presentation of collected glucose data. Some of these reporting and display features are shown in FIG. 8, FIG. 15, and FIG. 16. In addition, FIG. 32 illustrates a sample of a glucose trend summary report 1500, which may be generated by the decision support software in response to an appropriate user request or instruction. The glucose trend summary report 1500 can be generated as an output display screen, a printed page, or in any desired format. The glucose trend summary report 1500 presents the received glucose data in different graphical formats. This particular embodiment of the glucose trend summary report 1500 generally includes, without limitation: a sensor glucose overlay report 1502; a glycemic variability distribution report 1504; a weekly glycemic variability report 1506; and an observations report 1508. In certain embodiments, all of these reports appear together on the same page or display screen, as depicted in FIG. 32.

The sensor glucose overlay report 1502 and the glycemic variability distribution report 1504 are separately shown in FIG. 33, and are described in more detail below. Characteristics and features of the weekly glycemic variability report 1506 are discussed below with reference to FIG. 34, which illustrates another weekly glycemic variability report of the type that may be found in the glucose trend summary report 1500. The observations report 1508 contains one or more descriptions of certain event occurrences, detected trends, detected conditions, or the like. In this context, the observations report 1508 provides additional guidance and focus to the user to highlight important, critical, or urgent issues that might involve the treatment or therapy plan for the patient.

Figure 33:
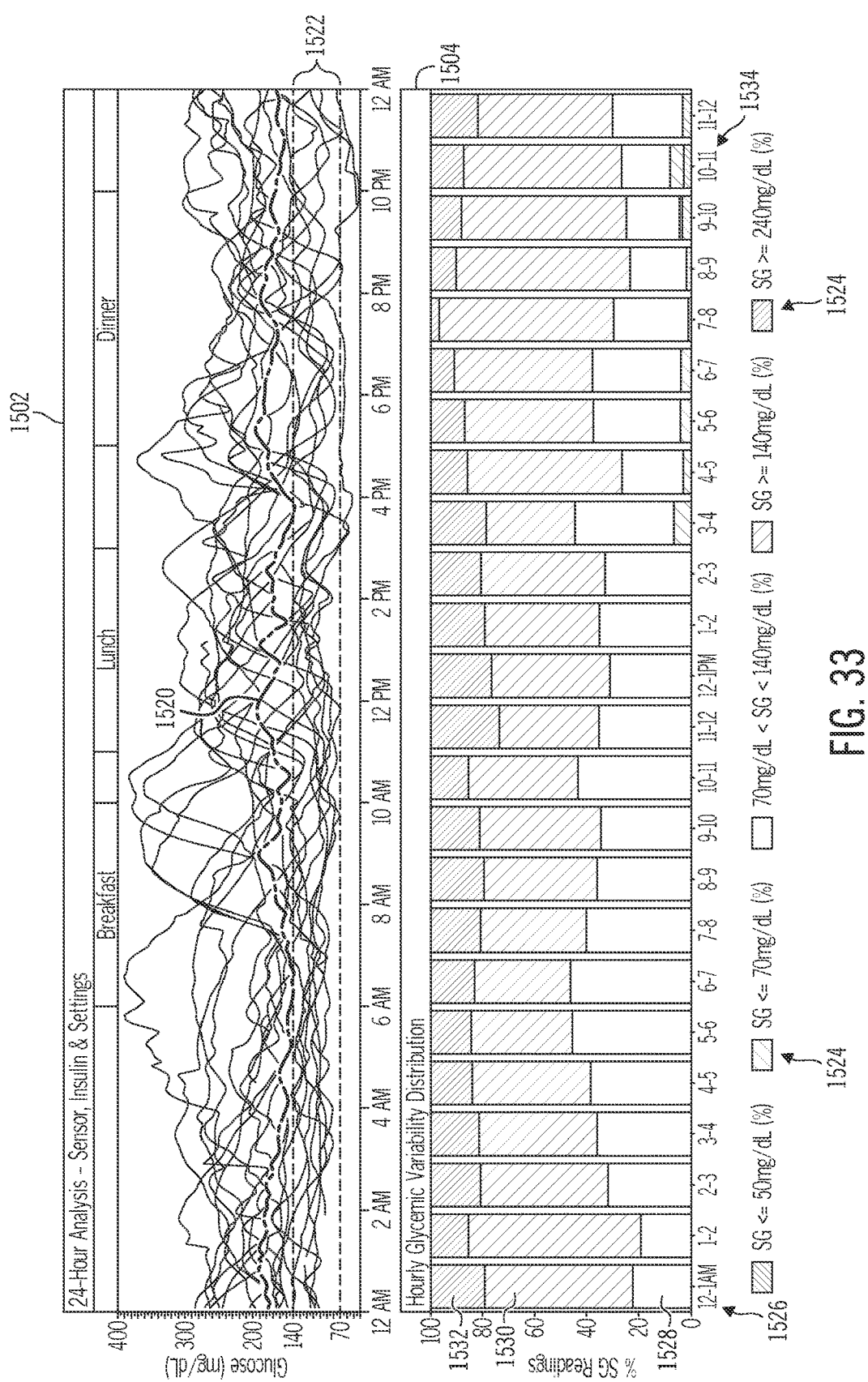
FIG. 33 illustrates a portion of the glucose trend summary report in greater detail.

Referring now to FIG. 33, the sensor glucose overlay report 1502 is similar to the overlay report corresponding to the overnight sensor glucose region 802 described above with reference to FIG. 8, and is similar to the overlay report 200 described above with reference to FIG. 2A. The report 1502 represents a collection of 24-hour sensor glucose data plots, e.g., for 28 days, for one month, for one week, or for any number of 24-hour periods. The report 1502 includes an average glucose plot 1520 (shown in dashed lines) that is superimposed over the actual sensor glucose data plots. The report 1502 may include a visually distinguishable (shaded, color-coded, or highlighted) target glucose zone 1522 that indicates sensor glucose values that are within the target range for the patient. For this example, the target glucose zone 1522 is defined between 70 mg/dL and 140 mg/dL. The report 1502 may also be rendered with visually distinguishable characteristics to distinguish sensor glucose values that fall within the target glucose zone 1522 from hypoglycemic and hyperglycemic values. For example, hyperglycemic sensor glucose values and/or areas bounded by their plots may be colored yellow, and hypoglycemic sensor glucose values and/or areas bounded by their plots may be colored red.

With continued reference to FIG. 33, the glycemic variability distribution report 1504 breaks down the 24-hour period into one-hour segments, which are shown along the horizontal axis. Each segment is rendered as distinguishable section or area, e.g., a vertically oriented bar. The vertical axis represents the percentage of sensor glucose readings (for each respective one-hour segment) that fall within a defined range of values. The different ranges are represented by a color-coding, shading, or other visually distinguishable scheme. This example uses the following color-coding scheme to visually represent five different ranges: dark red (to indicate severe hypoglycemic values of SG≤50 mg/dL); pink (to indicate hypoglycemic values, where SG≤70 mg/dL); green (to indicate target zone or normal values, where 70 mg/dL<SG<140 mg/dL); light yellow (to indicate hyperglycemic values, where SG≥140 mg/dL); and dark yellow (to indicate severe hyperglycemic values, where SG≥240 mg/dL). FIG. 33 employs different shading and cross-hatching to represent these colors. The glycemic variability distribution report 1504 includes or is otherwise associated with a legend 1524 that identifies this particular color-coding scheme. It should be appreciated that more or less than five different ranges could be utilized to generate the glycemic variability distribution report 1504, and that the specific SG values used to define the range thresholds may vary from that described above.

Within any given one-hour segment, the height, size, and area of each displayed color corresponds to the distribution percentage for the respective SG values. For example, the 12:00 AM to 1:00 AM segment 1526 includes three color-coded areas: a green area 1528; a light yellow area 1530 overlying the green area 1528; and a dark yellow area 1532 overlying the light yellow area 1530. The size of the green area 1528 indicates that roughly 20% of the SG data collected between 12:00 AM and 1:00 AM falls within the patient's target glucose range. The size of the dark yellow area 1532 indicates that roughly 20% of the SG data collected between 12:00 AM and 1:00 AM falls within the patient's severe hyperglycemic range. The size of the light yellow area 1530 indicates that roughly 60% of the SG data collected between 12:00 AM and 1:00 AM falls within the patient's hyperglycemic range. Accordingly, the user of the decision support software can view the glycemic variability distribution report 1504 to quickly determine that the patient typically does not become hypoglycemic between 12:00 AM and 1:00 AM.

Referring to the 10:00 PM to 11:00 PM segment 1534, the SG data exhibits a wider distribution of values. In this regard, the segment 1534 includes areas corresponding to all five of the possible glycemic ranges. Notably, the different color-coded areas are preferably arranged in an intuitive manner that corresponds to the range values. Thus, the dark red (severe hypoglycemic range) appears at the bottom of the segment 1534, the dark yellow (severe hyperglycemic range) appears at the top of the segment 1534, and the other colored areas are similarly ordered from the bottom to the top of the segment 1534.

FIG. 34 illustrates a sample of a weekly glycemic variability report 1550 of the type that may be found in the glucose trend summary report 1500 (FIG. 32). The weekly glycemic variability report 1550 breaks down the received SG data according to the seven days of the week. Accordingly, the report 1550 includes seven rows corresponding to the days of the week. The report 1550 is divided into four time periods, which are arranged as columns: overnight (12:00 AM to 6:00 AM); morning (6:00 AM to 12:00 PM); afternoon (12:00 PM to 6:00 PM); and evening (6:00 PM to 12:00 AM). It should be appreciated that a given weekly glycemic variability report may include more or less than four time periods. Moreover, although each time period in the report 1550 spans six hours, a given weekly glycemic variability report could use unequal time periods if so desired. For this example, each time period column is divided into two sub-columns: a hypoglycemic percentage column; and a hyperglycemic percentage column. Accordingly, the illustrated example includes eight sub-columns for each day of the week, which results in a total of 56 "percentage boxes" available on the report 1550.

The weekly glycemic variability report 1550 employs color-coding (or some other visually distinguishable scheme) to indicate the percentage of sensor glucose readings for each combination of day and time period. In contrast with the color-coding utilized for the glycemic variability distribution report 1504 (where different colors indicate different ranges of SG values), the color-coding scheme employed by the weekly glycemic variability report 1550 indicates different percentage thresholds. For example, the report 1550 may utilize six (or any desired number) different color intensity levels to indicate increasing percentages related to hypoglycemic SG data values, and six (or any desired number) different color intensity levels to indicate increasing percentages related to hyperglycemic SG data values. In this regard, the report 1550 may use the following color intensity scheme to indicate percentages of hypoglycemic values: white (indicating a low percentage); pink; dark pink; light red; red; and dark red (indicating a high percentage). Similarly, the report 1550 may use the following color intensity scheme to indicate percentages of hyperglycemic values: white (indicating a low percentage); faint yellow; light yellow; yellow; bright yellow; and intense dark yellow (indicating a high percentage).

Although the specific percentage thresholds may vary from one embodiment to another, the example presented here uses the following thresholds for hypoglycemic SG levels: 6, 10, 14, 18, 22, and 26 percent, wherein higher percentages are indicated using increasingly higher "red" shaded intensity levels. Moreover, the example described here uses the following thresholds for hyperglycemic SG levels: 45, 50, 55, 60, 65, and 70 percent, wherein higher percentages are indicated using increasingly higher "yellow" shaded intensity levels.

Referring to FIG. 34, the SG data indicates that the patient rarely if ever goes hypoglycemic during the overnight period on Saturdays. Accordingly, the box 1552 is rendered using the lowest intensity color assigned to hypoglycemic conditions (e.g., white). In contrast, the SG data also indicates that the patient goes hypoglycemic 20% of the time during the overnight period on Mondays. Thus, the box 1554 is rendered using one of the higher intensity colors assigned to hypoglycemic conditions (e.g., red). As another example, the SG data indicates that the patient goes hyperglycemic 51% of the time during the morning period on Tuesdays. Accordingly, the box 1556 is rendered using one of the lower intensity colors assigned to hyperglycemic conditions (e.g., faint yellow). As yet another example, the SG data indicates that the patient only goes hyperglycemic 25% of the time during the afternoon period on Sundays. For this reason, the box 1558 is rendered using the lowest intensity color assigned to hyperglycemic conditions (e.g., white).

Referring back to FIG. 32, the different components of the glucose trend summary report 1500 provide different views of the collected SG data such that the user can quickly visualize the glycemic profile of the patient and detect any potential problems or issues. Although the source SG data is the same, the components of the report 1500 represent the SG data in different formats to provide an intuitive graphical view that is easy to interpret.

The foregoing detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the foregoing technical field, background, brief summary or the following detailed Description.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. It should be appreciated that the various block components shown in the figures may be realized by any number of hardware, software, and/or firmware components configured to perform the specified functions. When implemented in software or firmware, various elements of the systems described herein are essentially the code segments or instructions that perform the various tasks. The program or code segments can be stored in a processor-readable medium, which may include any medium that can store or transfer information. Examples of a processor-readable medium include an electronic circuit, a semiconductor memory device, a ROM, a flash memory, an erasable ROM (EROM), a floppy diskette, a CD-ROM, an optical disk, a hard disk, or the like.

The various tasks performed in connection with a process described herein may be performed by software, hardware, firmware, or any combination thereof. It should be appreciated that a process described herein may include any number of additional or alternative tasks, the tasks shown in the figures need not be performed in the illustrated order, and a described process may be incorporated into a more comprehensive procedure or process having additional functionality not described in detail herein. Moreover, one or more of the tasks shown in the figures could be omitted from an embodiment of a described process as long as the intended overall functionality remains intact.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. An insulin infusion system comprising:
an insulin infusion device; and
an electronic device comprising:
  a processor device; and
  at least one memory element associated with the processor device, the at least one memory element storing processor-executable instructions that, when executed by the processor device, perform a method of managing use of the insulin infusion device, the method comprising:
    receiving glucose data for a user of the insulin infusion device, the glucose data indicating blood glucose levels of the user for a plurality of days and for periods of time during which the insulin infusion device is regulating delivery of insulin to the user;
    reviewing the received glucose data to identify bolus calculator event data corresponding to use of a bolus calculator of the insulin infusion device, wherein the reviewing uses a pattern recognition technique on the received glucose data, wherein the bolus calculator calculates each bolus dosage recommendation based on a respective user-entered carbohydrate consumption value, a respective user-entered current blood glucose value, a user-specific insulin sensitivity value, and a user-specific carbohydrate ratio value;
    filtering the identified bolus calculator event data to isolate correction bolus events having no food bolus component or a minimal food bolus component, wherein the filtering uses a pattern recognition technique on the identified bolus calculator event data;
    filtering the identified bolus calculator event data to isolate food bolus events having no correction bolus component or a minimal correction bolus component, wherein the filtering uses a pattern recognition technique on the identified bolus calculator event data;
    analyzing the isolated correction bolus events to check for event occurrences that are indicative of potential maladjustment of the insulin sensitivity value;
    analyzing the isolated food bolus events to check for event occurrences that are indicative of potential maladjustment of the carbohydrate ratio value;
    wherein event occurrences are checked in a predetermined sequence, utilizing a prioritization scheme to ensure that conflicting recommendations are not provided and to make only one recommendation at a time;
    determining, based on the analyzing and the prioritization scheme, that a particular recommendation corresponding to a detected event occurrence is needed;
    outputting a first recommendation and one or more commands to the insulin infusion device to adjust the insulin sensitivity value in response to the determining, and in response to detection of an event occurrence indicative of potential maladjustment of the insulin sensitivity value; and
    outputting a second recommendation and one or more commands to the insulin infusion device to adjust the carbohydrate ratio value in response to the determining, and in response to detection of an event occurrence indicative of potential maladjustment of the carbohydrate ratio value;
  wherein the insulin infusion device automatically adjusts the insulin sensitivity value in accordance with the one or more commands for the first recommendation, or automatically adjusts the carbohydrate ratio value in accordance with the one or more commands for the second recommendation, and
  wherein the predetermined sequence includes checks performed in the following order:
    (1) check for long term hypoglycemia, post-bolus;
    (2) check for short term hypoglycemia, post-bolus;

(3) check for long term high glycemic variability;
(4) check for short term high glycemic variability;
(5) check for long term hyperglycemia; and
(6) check for short term hyperglycemia.

2. The insulin infusion system of claim 1, wherein the received glucose data comprises sensor glucose data obtained from a continuous glucose monitor sensor.

3. The insulin infusion system of claim 1, wherein the outputting comprises:
generating a report that includes the recommendation.

4. The insulin infusion system of claim 1, wherein the method performed by the processor-executable instructions further comprises:
filtering the identified bolus calculator event data to remove glucose data associated with an override of a bolus dosage recommendation, an active insulin condition, or a back-to-back bolus condition, resulting in filtered bolus calculator event data;
wherein the analyzing step analyzes the filtered bolus calculator event data.

5. The insulin infusion system of claim 1, wherein:
the detected event occurrence comprises a long term hypoglycemic event occurring after a food bolus event; and
the recommendation comprises a suggestion to increase the carbohydrate ratio value.

6. The insulin infusion system of claim 1, wherein:
the detected event occurrence comprises a long term hyperglycemic event occurring after a food bolus event; and
the recommendation comprises a suggestion to decrease the carbohydrate ratio value.

7. The insulin infusion system of claim 1, wherein:
the detected event occurrence comprises a limited increase or decrease in blood glucose level occurring at a designated time after a food bolus event; and
the recommendation comprises a suggestion to increase the carbohydrate ratio value.

8. The insulin infusion system of claim 1, wherein:
the detected event occurrence comprises a large increase in blood glucose level occurring at a designated time after a food bolus event; and
the recommendation comprises a suggestion to decrease the carbohydrate ratio value.

9. The insulin infusion system of claim 1, wherein:
the detected event occurrence comprises a long term hypoglycemic event occurring after a correction bolus event; and
the recommendation comprises a suggestion to increase the insulin sensitivity value.

10. The insulin infusion system of claim 1, wherein:
the detected event occurrence comprises a long term hyperglycemic event occurring after a correction bolus event; and
the recommendation comprises a suggestion to decrease the insulin sensitivity value.

11. The insulin infusion system of claim 1, wherein:
the detected event occurrence comprises a rapid decrease in blood glucose level occurring at a designated time after a correction bolus event; and
the recommendation comprises a suggestion to increase the insulin sensitivity value.

12. The insulin infusion system of claim 1, wherein:
the detected event occurrence comprises a limited decrease or increase in blood glucose level occurring at a designated time after a correction bolus event; and
the recommendation comprises a suggestion to decrease the insulin sensitivity value.

13. The insulin infusion system of claim 1, wherein:
the detected event occurrence comprises a long term high glucose variability event occurring after a food bolus event; and
the recommendation comprises a suggestion related to dietary habits of the user.

14. The insulin infusion system of claim 1, wherein:
the detected event occurrence comprises a high glucose variability event occurring at a designated time after a food bolus event; and
the recommendation comprises a suggestion related to dietary habits of the user.

15. The insulin infusion system of claim 1, wherein:
the detected event occurrence comprises a high negative rate of change event occurring at a food bolus event; and
the recommendation comprises a suggestion to consume a meal earlier, relative to a corresponding food bolus infusion time.

16. The insulin infusion system of claim 1, wherein:
the detected event occurrence comprises a high positive rate of change event occurring at a food bolus event; and
the recommendation comprises a suggestion to consume a meal later, relative to a corresponding food bolus infusion time.

17. The insulin infusion system of claim 1, wherein:
the detected event occurrence comprises a long term high glucose variability event occurring after a correction bolus event; and
the recommendation comprises a suggestion related to use of a glucose meter and a glucose sensor.

18. A method of managing use of an insulin infusion device, the method comprising:
identifying bolus calculator event data from glucose data for a user of the insulin infusion device, the identified bolus calculator event data corresponding to use of a bolus calculator of the insulin infusion device over a plurality of days, wherein the identifying uses a pattern recognition technique on the glucose data, wherein the bolus calculator calculates each bolus dosage recommendation based on a respective user-entered carbohydrate consumption value, a respective user-entered current blood glucose value, a user-specific carbohydrate ratio value, and a user-specific insulin sensitivity value;
filtering the identified bolus calculator event data to remove glucose data associated with an override of a bolus dosage recommendation, an active insulin condition, or a back-to-back bolus condition, resulting in filtered bolus calculator event data, and to isolate correction bolus events having no food bolus component or a minimal food bolus component, and to isolate food bolus events having no correction bolus component or a minimal correction bolus component, wherein the filtering uses a pattern recognition technique on the identified bolus calculator event data;
analyzing the filtered bolus calculator event data to check for event occurrences that are indicative of potential maladjustment of the user-specific carbohydrate ratio value or the user-specific insulin sensitivity value, wherein event occurrences are checked in a predetermined sequence, utilizing a prioritization scheme to ensure that conflicting recommendations are not provided and to make only one recommendation at a time;

determining, based on the analyzing and the prioritization scheme, that a particular recommendation corresponding to a detected event occurrence is needed;

outputting the particular recommendation and one or more commands to the insulin infusion device to adjust the user-specific carbohydrate ratio value or the user-specific insulin sensitivity value, based on characteristics of the detected event occurrence; and automatically adjusting the carbohydrate ratio value or the insulin sensitivity value at the insulin infusion device, in accordance with the one or more commands;

wherein the predetermined sequence includes checks performed in the following order:
(1) check for long term hypoglycemia, post-bolus;
(2) check for short term hypoglycemia, post-bolus;
(3) check for long term high glycemic variability;
(4) check for short term high glycemic variability;
(5) check for long term hyperglycemia; and
(6) check for short term hyperglycemia.

19. The insulin infusion system of claim 1, wherein:
the detected event occurrence comprises a high glucose variability event occurring at a designated time after a correction bolus event; and
the recommendation comprises a suggestion related to use of a glucose meter and a glucose sensor.

20. The method of claim 18, wherein the outputting comprises:
generating a report that includes the particular recommendation.

21. The method of claim 18, wherein:
the detected event occurrence comprises a long term hypoglycemic event occurring after a food bolus event; and
the particular recommendation comprises a suggestion to increase the carbohydrate ratio value.

22. The method of claim 18, wherein:
the detected event occurrence comprises a long term hyperglycemic event occurring after a food bolus event; and
the particular recommendation comprises a suggestion to decrease the carbohydrate ratio value.

23. The method of claim 18, wherein:
the detected event occurrence comprises a limited increase or decrease in blood glucose level occurring at a designated time after a food bolus event; and
the particular recommendation comprises a suggestion to increase the carbohydrate ratio value.

24. The method of claim 18, wherein:
the detected event occurrence comprises a large increase in blood glucose level occurring at a designated time after a food bolus event; and
the particular recommendation comprises a suggestion to decrease the carbohydrate ratio value.

25. The method of claim 18, wherein:
the detected event occurrence comprises a high glucose variability event occurring after a food bolus event; and
the particular recommendation comprises a suggestion related to dietary habits of the user.

26. The method of claim 18, wherein:
the detected event occurrence comprises a long term hypoglycemic event occurring after a correction bolus event; and
the particular recommendation comprises a suggestion to increase the insulin sensitivity value.

27. The method of claim 18, wherein:
the detected event occurrence comprises a long term hyperglycemic event occurring after a correction bolus event; and
the particular recommendation comprises a suggestion to decrease the insulin sensitivity value.

28. The method of claim 18, wherein:
the detected event occurrence comprises a rapid decrease in blood glucose level occurring at a designated time after a correction bolus event; and
the particular recommendation comprises a suggestion to increase the insulin sensitivity value.

29. The method of claim 18, wherein:
the detected event occurrence comprises a limited decrease or increase in blood glucose level occurring at a designated time after a correction bolus event; and
the particular recommendation comprises a suggestion to decrease the insulin sensitivity value.

30. The method of claim 18, wherein:
the detected event occurrence comprises a high glucose variability event occurring at a designated time after a food bolus event; and
the particular recommendation comprises a suggestion related to dietary habits of the user.

31. The method of claim 18, wherein:
the detected event occurrence comprises high negative rate of change event occurring at a food bolus event; and
the particular recommendation comprises a suggestion to consume a meal earlier, relative to a corresponding bolus infusion time.

32. The method of claim 18, wherein:
the detected event occurrence comprises a high positive rate of change event occurring at a food bolus event; and
the particular recommendation comprises a suggestion to consume a meal later, relative to a bolus infusion time.

33. The method of claim 18, wherein:
the detected event occurrence comprises a long term high glucose variability event occurring after a correction bolus event; and
the particular recommendation comprises a suggestion related to use of a glucose meter and a glucose sensor.

34. The method of claim 18, wherein:
the detected event occurrence comprises a high glucose variability event occurring at a designated time after a correction bolus event; and
the particular recommendation comprises a suggestion related to use of a glucose meter and a glucose sensor.

* * * * *